(12) United States Patent
Altmann et al.

(10) Patent No.: US 6,353,017 B1
(45) Date of Patent: Mar. 5, 2002

(54) DIPEPTIDE NITRILES

(75) Inventors: Eva Altmann, Reinach (CH); Claudia Betschart, Takarazuka (JP); Keigo Gohda; Miyuki Horiuchi, both of Hyogo (JP); Rene Lattmann, Binningen; Martin Missbach, Gipf-Oberfrick, both of (CH); Junichi Sakaki, Hyogo (JP); Michihiro Takai, Ibaraki (JP); Naoki Teno, Hyogo (JP); Scott Douglas Cowen, Branchburg, NJ (US); Paul David Greenspan, New Providence, NJ (US); Leslie Wighton McQuire, Warren, NJ (US); Ruben Alberto Tommasi, Whitehouse Station, NJ (US); John Henry van Duzer, Asbury, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/643,639

(22) Filed: Aug. 22, 2000

Related U.S. Application Data

(63) Continuation of application No. 09/186,223, filed on Nov. 4, 1998, now abandoned.
(60) Provisional application No. 60/108,160, filed on Dec. 5, 1997.

(30) Foreign Application Priority Data

Nov. 5, 1997 (GB) ................................. 9723407

(51) Int. Cl.$^7$ ....................... A61K 31/40; C07D 207/30
(52) U.S. Cl. ....................................... 514/428; 548/561
(58) Field of Search ........................... 548/561; 514/428

(56) References Cited

U.S. PATENT DOCUMENTS

| | | | |
|---|---|---|---|
| 3,467,691 A | | 9/1969 | Irikura et al. |
| 3,697,577 A | | 10/1972 | Irikura et al. |
| 5,574,064 A | | 11/1996 | Shibata et al. |
| 5,780,498 A | | 7/1998 | Saika et al. |
| 5,977,075 A | | 11/1999 | Ksander et al. |
| 5,990,083 A | * | 11/1999 | Iqbal et al. ............... 514/9 |
| 6,015,879 A | * | 1/2000 | McDonald ............... 530/331 |
| 6,287,840 B1 | * | 9/2001 | Palmer et al. ............... 435/219 |
| 6,297,277 B1 | * | 10/2001 | Zimmerman ............... 514/534 |

FOREIGN PATENT DOCUMENTS

| | | |
|---|---|---|
| BE | 662788 | 8/1965 |
| EP | 506 008 A1 | 9/1992 |
| EP | 547 699 A1 | 6/1993 |
| EP | 587 110 A2 | 3/1994 |
| EP | 611 756 A2 | 8/1994 |
| WO | WO 95 12611 | 5/1995 |
| WO | WO 95 24382 | 9/1995 |
| WO | WO 96 20949 | 7/1996 |
| WO | WO 96 33170 | 10/1996 |
| WO | WO 97/27200 | 7/1997 |
| WO | WO 98 01133 | 1/1998 |
| WO | WO 98/22433 | 5/1998 |
| WO | WO 00/51998 | 9/2000 |
| WO | WO 00/55125 | 9/2000 |
| WO | WO 00/55126 | 9/2000 |

OTHER PUBLICATIONS

Lowe et al., Biochem.J., vol. 124, No. 1, pp. 107–115 (1971).
Buttle et al., Biochem. J., vol. 261, No. 2, pp. 469–476 (1989).
Baker et al., Biochimica Biophysica Acta, vol. 616, pp. 30–34 (1980).
Liu et al., Biochimica Biophysica Acta, vol. 1250, pp. 43–48 (1995).
Stevenson et al., Biotechnology & Bioengineering, vol. 37, pp, 519–527 (1991).
Grzegorzewska et al., Bull.Acad.Pol.Sci., Ser.Sci.Chim., vol. 22, No. 8, pp. 679–683 (1974).
Varughese et al., Can.J.Chem., vol. 64, No. 8, pp. 1668–1673 (1986).
Gour–Salin et al.,Can.J.Chem., vol. 69, No. 8, pp. 1288–1297 (1991).
Suzue et al., Chem.Pharm.Bull., vol. 16, No. 8, pp. 1417–1432 (1968).
Gour–Salin et al.,Enzyme Microb.Technol., vol. 13, pp. 408–411 (1991).
Von Heinz Moser et al., Helvetica Chimica Acta, vol. 69, pp. 1224–1262 (1986).

(List continued on next page.)

*Primary Examiner*—Deborah C. Lambkin
(74) *Attorney, Agent, or Firm*—Norbert Gruenfeld

(57) ABSTRACT

N-terminal substituted dipeptide nitriles as defined are useful as inhibitors of cysteine cathepsins, e.g. cathepsins B, K, L and S, and can be used for the treatment of cysteine cathepsin dependent diseases and conditions, including inflammation, rheumatoid arthritis, osteoarthritis, osteoporosis, tumors (especially tumor invasion and tumor metastasis), coronary disease, atherosclerosis (including atherosclerotic plaque rupture and destabilization). Particular dipeptide nitriles are compounds of formula I, or physiologically-acceptable and -cleavable esters or a salts thereof

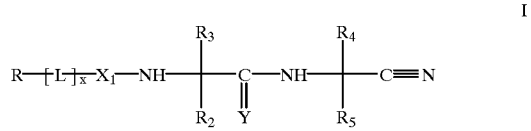

wherein: the symbols are as defined.

In particular it has been found that by appropriate choice of groups R, $R_2$, $R_3$, $R_4$, $R_5$, $X_1$, Y and L, the relative selectivity of the compounds as inhibitors of the various cysteine cathepsin types, e.g. cathepsins B, K, L and S may be altered, e.g. to obtain inhibitors which selectively inhibit a particular cathepsin type or combination of cathepsin types.

22 Claims, No Drawings

OTHER PUBLICATIONS

Lipshutz et al., Israel Jour. of Chemistry, vol. 27, pp. 49–55 (1986).
Carey et al., Journal of Biological Chemistry, vol. 259, No. 23, pp. 14357–14360 (1984).
Elmore et al., J.Chem.Soc.Perkin Trans., vol. 1, pp. 1051–1055 (1988).
Campbell et al., J.Am.Chem.Soc., vol. 104, pp. 5221–5226 (1982).
Lipshutz et al., J.Am.Chem.Soc., vol. 105, pp. 7703–7713 (1983).
Moon et al., J.Am.Chem.Soc., vol. 108, pp. 1350–1351 (1986).
Katritzky et al., Organic Prep.Proced.Int., vol. 24, No. 2, pp. 121–126 (1992).
Eugen Vargha, Stud.Univ.Babes–Bolyai.Ser.Chem., vol. 13, No. 2, pp. 31–35 (1968).
Balog et al., Stud.Univ.Babes–Bolyai.Ser.Chem., vol. 14, No. 2, pp. 137–143 (1969).
Claremon et al., Tetrahedron Letters, vol. 29, No. 18, pp. 2155–2158 (1988).
Jones et al., Tetrahedron Letters, vol. 29, No. 31, pp. 3853–3856 (1988).
Imoto et al., Bull.Chem.Soc.Japan, vol. 59, pp. 3207–3212 (1986).
Hanzlik et al., Biochimica et Biophysica Acta, vol. 1035, pp. 62–70 (1990).
Liu et al., Biochimica et Biophysica Acta, vol. 1158, pp. 264–272 (1993).
Pickin et al., Biochemical Soc. Transactions, vol. 18, pp. 316 (1990).
Thompson et al., J.Med.Chem., vol. 29, pp. 104–111 (1986).
Dufour et al., Biochemistry, vol. 34, No. 28, pp. 9136–9143 (1995).
Brisson et al., J.Biol.Chem., vol. 261, No. 20, pp. 9087–9089 (1986).
Khalid et al., Drugs Exptl.Clin.Res., Suppl. 1, XIII, pp. 57–60 (1987).
Liang et al., Arch. Biochemistry and Biophysics, vol. 252, No. 2, pp. 626–634 (1987).
Asboth et al., Biochemistry, vol. 24, pp. 606–609 (1985).
Chemical Abstract of JP 67010206, (2000).
Derwent Abstract of JP 67010206. (2000).
Chemical Abstract of JP 68010619, (2000).
Derwent Abstract of JP 68010619, (2000).
Chemical Abstract of JP 67009133, (2000).
Derwent Abstract of JP 67000133, (2000).
Chemical Abstract of JP 70015013, (2000).
Derwent Abstract of JP 70015013, (2000).
Chemical Abstract of JP 63301868, (2000).
Derwent Abstract of JP 63310868, (2000).
Chemical Abstract of PL–93135, (2000).
North et al., Tetrahedron, vol. 46, No. 24, pp. 8267–8290 (1990).
Harada et al., Institution of Molecular and Cellular Evolution, pp. 157–168 (1972).
Yoshida et al., CA 110;213341, 1989.

* cited by examiner

DIPEPTIDE NITRILES

This application is a continuation of application Ser. No. 09/186,223 filed Nov. 4, 1998, abandoned, which claims the benefit of provisional application No. 60/108,160 filed Dec. 5, 1997 (converted from application Ser. No. 08/985,973), all of which are incorporated herein by reference.

This invention relates to inhibitors of cysteine proteases, in particular to dipeptide nitrile cathepsin inhibitors and to their pharmaceutical use for the treatment or prophylaxis of diseases or medical conditions in which cathepsins are implicated.

The cysteine cathepsins, e.g. cathepsins B, K, L and S, are a class of lysosomal enzymes which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases, infectious diseases and immunologically mediated diseases (including transplant rejection).

In accordance with the invention it has been found that dipeptide nitrites are particularly useful as cysteine cathepsin inhibitors and can be used for the treatment of the above-cited cysteine cathepsin dependent conditions.

Accordingly the present invention provides an N-terminal-substituted dipeptide nitrile, i.e. a dipeptide in which the C-terminal carboxy group of the dipeptide is replaced by a nitrile group (—C≡N) and in which the N-terminal nitrogen atom is substituted via a peptide or pseudopeptide linkage which optionally additionally comprises a -methylene-hetero atom-linker or an additional hetero atom, directly by aryl, lower alkyl, lower alkenyl, lower alkynyl or heterocyclyl, or a physiologically-acceptable and -cleavable ester or a salt thereof, for use as a pharmaceutical.

The invention further provides a pharmaceutical composition comprising an N-terminal-substituted dipeptide nitrile as defined above as an active ingredient.

The invention also provides a method of treating a patient suffering from or susceptible to a disease or medical condition in which a cathepsin is implicated, comprising administering an effective amount of an N-terminal-substituted dipeptide nitrite as defined above to the patient.

The invention further includes the use of an N-terminal-substituted dipeptide nitrite as defined above for the preparation of a medicament for therapeutic or prophylactic treatment of a disease or medical condition in which a cathepsin is implicated.

The dipeptide nitrile of the invention conveniently comprises α-amino acid residues, including both natural and unnatural α-amino acid residues. Herein the "natural α-amino acid residues" denote the 20 amino acids obtainable by translation of RNA according to the genetic code or the corresponding nitrites thereof, as appropriate. "Unnatural α-amino acid residues" are α-amino acids which have α-substituents other than those found in "natural α-amino acid residues". Preferred α-amino acid residues, as the C-terminal amino acid residue of the dipeptide nitrite, are the nitrites of tryptophan, 2-benzyloxymethyl-2-amino-acetic acid, 2,2-dimethyl-2-amino-acetic acid, 2-butyl-2-amino-acetic acid, methionine, leucine, lysine, alanine, phenylalanine, and glycine and derivatives thereof, e.g. as hereinafter described. Preferred amino acid residues as the N-terminal amino acid residue of the dipeptide nitrite are 1-amino-cyclohexanecarboxylic acid, 1-amino-cycloheptanecarboxylic acid, phenylalanine, histidine, tryptophan and leucine and derivatives thereof, e.g. as hereinafter described.

The aryl, lower alkyl, lower alkenyl, lower alkynyl or heterocyclyl substituent (hereinafter referred to as R) is attached to the the N-terminal nitrogen atom of the dipeptide via a peptide linkage, i.e. as R—C(O)—NH—, or via a pseudopeptide linkage. Suitable pseudopeptide linkages include sulphur in place of oxygen and sulphur and phosporous in place of carbon, e.g. as R—C(S)—NH—, R—S(O)—NH—, R—S(O)$_2$—NH— or R—P(O)$_2$—NH and analogues thereof. Additionally the peptide or pseudopeptide linkage between the R substituent and the N-terminal nitrogen atom may comprise an additional hetero atom, e.g. as R—Het—C(O)—NH—, or a -methylene-hetero atom-linker, e.g. as R—Het—CH$_2$—C(O)—NH— or R—CH$_2$—Het—C(O)—NH—, wherein Het is a hetero atom selected from O, N or S, and pseudopeptide containing alternatives thereof, e.g. as defined above. When the linkage between the aryl substituent and the N-terminal nitrogen atom comprises a -methylene-hetero atom-linker, the methylene group and the hetero atom may be optionally further substituted, e.g. as hereinafter described.

The R substituent may be further substituted, e.g. by up to 3 substituents selected from halogen, hydroxy, amino, nitro, optionally substituted $C_{1-4}$alkyl (e.g. alkyl substituted by hydroxy, alkyloxy, amino, optionally substituted alkylamino, optionally substituted dialkylamino, aryl or heterocyclyl), $C_{1-4}$alkoxy, $C_{2-6}$alkenyl, CN, trifluoromethyl, trifluoromethoxy, aryl, (e.g. phenyl or phenyl substituted by CN, CF$_3$, halogen, OCH$_3$), aryloxy, (e.g. phenoxy or phenoxy substituted by CN, CF$_3$, halogen, OCH$_3$), benzyloxy or a heterocyclic residue.

Accordingly in preferred embodiments the invention provides a compound of formula I, or a physiologically-acceptable and -cleavable ester or a salt thereof

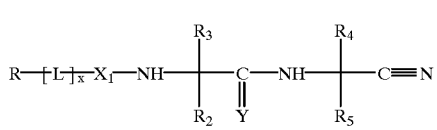

I wherein:
R is optionally substituted (aryl, lower alkyl, lower alkenyl, lower alkynyl, or heterocyclyl);

$R_2$ and $R_3$ are independently hydrogen, or optionally substitued [lower alkyl, cycloalkyl, bicycloalkyl, or (aryl, biaryl, cycloalkyl or bicycloalkyl)-lower alkyl]; or $R_2$ and $R_3$ together represent lower alkylene, optionally interrupted by O, S or NR$_6$, so as to form a ring with the carbon atom to which they are attached wherein R$_6$ is hydrogen, lower alkyl or aryl-lower alkyl; or either $R_2$ or $R_3$ are linked by lower alkylene to the adjacent nitrogen to form a ring;

$R_4$ and $R_5$ are independently H, or optionally substituted (lower alkyl, aryl-lower alkyl), —C(O)OR$_7$, or —C(O)NR$_7$R$_8$,
wherein
$R_7$ is optionally substituted (lower alkyl, aryl, aryl-lower alkyl, cycloalkyl, bicycloalkyl or heterocyclyl), and
$R_8$ is H, or optionally substituted (lower alkyl, aryl, aryl-lower alkyl, cycloalkyl, bicycloalkyl or heterocyclyl), or $R_4$ and $R_5$ together represent lower alkylene, optionally interrupted by O, S or $NR_6$, so as to form a ring with the carbon atom to which they are attached wherein $R_6$ is hydrogen, lower alkyl or aryl-lower alkyl, or $R_4$ is H or optionally substituted lower alkyl and $R_5$ is a substituent of formula —$X_2$—$(Y_1)_n$—$(Ar)_p$—Q—Z wherein
$Y_1$ is O, S, SO, $SO_2$, $N(R_6)SO_2$, N—$R_6$, $SO_2NR_6$, $CONR_6$ or $NR_6CO$;
n is zero or one;

p is zero or one;

$X_2$ is lower alkylene; or when n is zero, $X_2$ is also $C_2$–$C_7$-alkylene interrupted by O, S, SO, $SO_2$, $NR_6$, $SO_2NR_6$, $CONR_6$ or $NR_6CO$;
wherein $R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl;

Q is a direct bond, lower alkylene, $Y_1$-lower alkylene or $C_2$–$C_7$-alkylene interrupted by $Y_1$;

$X_1$ is —C(O)—, —C(S)—, —S(O)—, —S(O)$_2$—, —P(O)(OR$_6$)— wherein $R_6$ is as defined above;

Y is oxygen or sulphur;

L is optionally substituted —Het—, —Het—$CH_2$— or —$CH_2$—Het—, wherein Het is a hetero atom selected from O, N or S, and x is zero or one;

and aryl in the above definitions represents carbocyclic or heterocyclic aryl, for use as a pharmaceutical;

a pharmaceutical composition comprising a compound of formula I as defined above as an active ingredient;

a method of treating a patient suffering from or susceptible to a disease or medical condition in which a cathepsin is implicated, comprising administering an effective amount of a compound of formula I as defined above to the patient; and use of a compound of formula I as defined above for the preparation of a medicament for therapeutic or prophylactic treatment of a disease or medical condition in which a cathepsin is implicated.

The invention also provides novel dipeptide nitriles.

Accordingly the invention further provides a compound of formula I as defined above provided that when R is lower alkyl not substituted by aryl,
one of $R_4$ or $R_5$ is a substituent of formula —$X_2$—$(Y_1)_n$—$(Ar)_p$—Q—Z, provided that when x is one, L is —O—, or —$CH_2$—O— and $X_1$ is —C(O)—,
either one of $R_4$ or $R_5$ is a substituent of formula —$X_2$—$(Y_1)_n$—$(Ar)_p$—Q—Z, or R is not unsubstituted phenyl, provided that when $R_2$=$R_4$=$R_5$=H, x is zero and $X_1$ is —C(O)—,
$R_3$ is not H, —$CH_3$, —$CH(CH_3)_2$, —$CH_2$—CH—$(CH_3)_2$, —$CH_2$—COOH, or —$CH_2$—COO—$CH_2$—$CH_3$, when R is unsubstituted phenyl,
$R_3$ is not H, —$CH(CH_3)_2$, or —$CH_2$—CH—$(CH_3)_2$, when R is 4-aminophenyl or 4-nitrophenyl, $R_3$ is not H when R is 3-aminophenyl, 3-nitrophenyl 2-chloropyridin-4-yl, or vinyl or
$R_3$ is not —$CH_2$—$CH_2$—S—$CH_3$ when R is pyridin-3-yl or 2-chloropyridin4-yl, provided that when $R_2$=$R_3$=$R_4$=H, x is zero and $X_1$ is —C(O)— and R is phenyl,
$R_5$ is not —$CH(CH_3)_2$, provided that when $R_3$=$R_4$=H, $R_5$ is —$CH_2$—$CH_2$—COOH, x is zero and $X_1$ is —C(O)—,
$R_2$ does not form a heterocyclic ring with the adjacent nitrogen atom, and provided that when $R_2$=$R_3$=$R_4$=$R_5$=H, x is zero and $X_1$ is —$SO_2$—,
R is not 4-methylphenyl.

In formula I R, $R_2$, $R_3$, $R_4$, $R_5$ and L may be further substituted by one or more, e.g. up to 3, substituents independently selected from lower alkyl, aryl, aryl-lower alkyl, cycloalkyl, heterocyclyl, —CN, -halogen, —OH, —$NO_2$, —$NR_9R_{10}$, —$X_3$—$R_7$, lower alkyl-$X_3$—$R_8$, halo-substituted lower alkyl, wherein $R_7$ and $R_8$ are as defined above, $X_3$ is —O—, —S—, —$NR_8$—, —C(O)—, —C(S)—, —S(O)—, —S(O)$_2$—, —C(O)O—, —C(S)O—, —C(O)$NR_8$—,
wherein $R_8$ is as defined above, $R_9$ and $R_{10}$ are independently as defined above for $R_8$, or —$X_4$—$R_8$,
wherein $X_4$ is —C(O)—, —C(S)—, —S(O)—, —S(O)$_2$—, —C(O)O—, —C(S)O—, —C(O)$NR_6$—
wherein $R_6$ and $R_7$ are as defined above, or $R_8$ and $R_{10}$ together with N form a heteroaryl group or a saturated or unsaturated heterocycloalkyl group, optionally containing one or more additional heteroatoms selected from O, N or S.

Compounds of formula I exhibit valuable pharmacological properties in mammals, in particular as cysteine cathepsin inhibitors. In accordance with the present invention it has been found that by appropriate choice of groups R, $R_2$, $R_3$, $R_4$, $R_5$, $X_1$, Y and L, the relative selectivity of the compounds as inhibitors of the various cysteine cathepsin types, e.g. cathepsins B, K, L and S may be altered, e.g. to obtain inhibitors which selectively inhibit a particular cathepsin type or combination of cathepsin types.

In a first aspect the invention provides a compound of formula II, or a physiologically-acceptable and -cleavable ester or a salt thereof

II

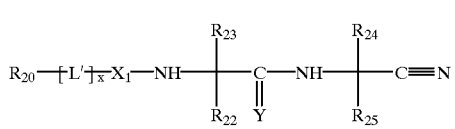

wherein:
$R_{20}$ is optionally substituted (aryl, aryl-lower alkyl, lower alkenyl, lower alkynyl, heterocyclyl, or heterocyclyl-lower alkyl);

$R_{22}$ is H, or optionally substitued lower alkyl, and $R_{23}$ is optionally substituted (lower alkyl, aryl-lower alkyl, or cyloalkyl-lower alkyl) or $R_{22}$ and $R_{23}$ together with the carbon atom to which they are attached form an optionally substituted (cycloalkyl group or heterocycloalkyl group);

$R_{24}$ and $R_{25}$ are independently H, or optionally substituted (lower alkyl, or aryl-lower alkyl), —C(O)O$R_7$, or —C(O)$NR_7R_8$ wherein $R_7$ and $R_8$ are as defined above, or
$R_{24}$ and $R_{25}$, together with the carbon atom to which they are attached form an optionally substituted (cycloalkyl group or heterocycloalkyl group);
$X_1$ is as defined above;
Y is oxygen or sulphur;
L' is optionally substituted (—Het—$CH_2$— or —$CH_2$—Het—),
wherein Het is a a hetero atom selected from O, N or S, and
x is 1 or 0,
provided that when x is one, L is —$CH_2$—O— and $X_1$ is —C(O)—,
$R_{20}$ is not unsubstituted phenyl,
provided that when $R_{22}=R_{24}=R_{25}$=H, x is zero and $X_1$ is —C(O)—,
$R_{23}$ is not H, —$CH_3$, —$CH(CH_3)_2$, —$CH_2$—CH—$(CH_3)_2$, —$CH_2$—COOH, or —$CH_2$—COO—$CH_2$—$CH_3$, when $R_{20}$ is unsubstituted phenyl,
$R_{23}$ is not H, —$CH(CH_3)_2$, or —$CH_2$—CH—$(CH_3)_2$, when $R_{20}$ is 4-aminophenyl or 4-nitrophenyl,
$R_{23}$ is not H when $R_{20}$ is 3-amninophenyl, 3-nitrophenyl 2-chloropyridin-4-yl, or vinyl, or
$R_{23}$ is not —$CH_2$—$CH_2$—S—$CH_3$ when $R_{20}$ is pyridin-3-yl or 2-chloropyridin-4-yl,
provided that when $R_{22}=R_{23}=R_{24}$=H, x is zero and $X_1$ is —C(O)— and $R_{20}$ is phenyl,
$R_{25}$ is not —$CH(CH_3)_2$,
provided that when $R_{23}=R_{24}$=H, $R_{25}$ is —$CH_2$—$CH_2$—COOH, x is zero and $X_1$ is —C(O)—,
$R_{22}$ does not form a heterocyclic ring with the adjacent nitrogen atom, and
provided that when $R_{22}=R_{23}=R_{24}=R_{25}$=H, x is zero and $X_1$ is —$SO_2$—,
$R_{20}$ is not 4-methylphenyl.

Compounds of formula II are typically inhibitors of cathepsins K, L or S, especially selective inhibitors of catepsin K or cathepsin L or cathepsin S, or in some case inhibitors of, e.g. cathepsins L and S.

The substituents of the compounds of formula II have the following preferred significances. Preferred compounds of formula II comprise compounds having preferred substituents, singly or in any combination.

Preferably when $R_{20}$ comprises aryl, the aryl is optionally substituted (phenyl, naphthylenyl, phenanthrenyl, thiophenyl, furanyl, pyrrolyl, pyrazolyl, thiazolyl, pyridinyl, indolyl, quinolinyl, isoquinolinyl, benzothienyl and benzofuranyl).

Preferably $R_{22}$ is hydrogen.

Preferably $R_{23}$ is optionally substituted (lower alkyl, aryl-lower alkyl or cycloalkyl-lower alkyl), or $R_{23}$ and $R_{22}$ together with the carbon atom to which they are attached form a $C_{5-C8}$, especially a $C_6$ or $C_7$, cycloalkylgroup. More preferably $R_{23}$ is —$CH_2$—$CH(CH_3)_2$, or optionally substituted benzyl, cyclohexylmethyl, naphthalenylmethyl, indolylmethyl, benzothienylmethyl or benzofuranylmethyl, or $R_{23}$ and $R_{22}$ together with the carbon atom to which they are attached form a cyclohexane ring.

Preferred significances for $R_{24}$ and $R_{25}$ are:
$R_{24}$ and $R_{25}$ are both H or —$CH_3$, or
$R_{24}$ is H and $R_{25}$ is aryl-lower alkyl, lower alkyl, both optionally substitued by up to 3 substituents selected from amino, halogen (e.g. fluorine or preferably chlorine) or S—$CH_3$, or
$R_{24}$ and $R_{25}$ together with the carbon atom to which they are attached form a $C_3$–$C_7$ cycloalkyl ring.

More preferably $R_{24}$ is H and $R_{25}$ is optionally substituted (—$CH_2$-phenyl, —$CH_2$-indolyl, —$(CH_2)_2$—S—$CH_3$, —$CH_2$—$CH(CH_3)_2$, —$(CH_2)_4$—$NH_2$ or —$(CH_2)_3$—$CH_3$), or yet more preferably $R_4$ and $R_5$ are both —$CH_3$, or especially $R_4$ and $R_5$ are both H.

Preferably —$X_1$— is —C(O)—.
Preferably Y is=O.
Preferably either x is 0, or when x is 1 L' is —$CH_2$—O—, —NH—$CH_2$—, —O—$CH_2$— or —S—$CH_2$.

In particular embodiments the invention provides a compound of formula II' or a physiologically-acceptable and -cleavable ester or a salt thereof

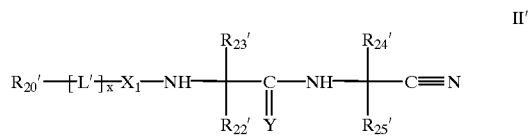

wherein:
$R_{20}'$ is optionally substituted ($C_6$–$C_{18}$ aryl or $C_4$–$C_{18}$ heteroaryl);
$R_{22}'$ is H, or optionally substitued $C_1$–$C_8$ alkyl, and
$R_{23}'$ is optionally substituted ($C_2$–$C_8$ alkyl, or $C_7$–$C_{14}$ aralkyl), or
$R_{22}'$ and $R_{23}'$ together with the carbon atom to which they are attached form an optionally substituted ($C_3$–$C_8$ cycloalkyl group or $C_4$–$C_7$ heterocycloalkyl group);
$R_{24}'$ and $R_{25}'$ are independently H, or optionally substituted ($C_1$–$C_8$ alkyl, $C_7$–$C_{14}$ aralkyl, or $C_5$–$C_{14}$ heteroaralkyl), —C(O)O$R_6'$, or —C(O)N$R_6'R_7'$
wherein
$R_6'$ is optionally substituted ($C_1$–$C_8$ alkyl, $C_7$–$C_{14}$ aralkyl, $C_3$–$C_8$ cycloalkyl, $C_4$–$C_7$ heterocycloalkyl, $C_5$–$C_{14}$ heteroaralkyl, $C_6$–$C_{14}$ aryl, or $C_4$–$C_{14}$ heteroaryl), and
$R_7'$ is H, or optionally substituted ($C_1$–$C_8$ alkyl, $C_7$–$C_{14}$ aralkyl, $C_3$–$C_8$ cycloalkyl, $C_4$–$C_7$ heterocycloalkyl, $C_5$–$C_{14}$ heteroaralkyl, $C_6$–$C_{14}$ aryl, or $C_4$–$C_{14}$ heteroaryl), or
$R_{24}'$ and $R_{25}'$ together with the carbon atom to which they are attached form an optionally substituted ($C_3$–$C_8$ cycloalkyl group or $C_4$–$C_7$ heterocycloalkyl group);
$X_1$ is —C(O)—, —C(S)—, —S(O)—, —$S(O)_2$—, —P(O)(O$R_6'$)—
wherein R' is as defined above;
Y is oxygen or sulphur;
L' is optionally substituted (—Het—$CH_2$— or —$CH_2$—Het—),
wherein Het is a a hetero atom selected from O, N or S, and x is 1 or 0,
provided that when x is one, L' is —$CH_2$—O— and $X_1$ is —C(O)—
$R_{20}'$ is not unsubstituted phenyl,
provided that when $R_{22}'=R_{24}'=R_{25}'$=H, x is zero and $X_1$ is —C(O)—,
$R_{23}'$ is not H, —$CH_3$, —$CH(CH_3)_2$, —$CH_2$—CH—$(CH_3)_2$, —$CH_2$—COOH, or —$CH_2$—COO—$CH_2$—$CH_3$, when $R_{20}'$ is unsubstituted phenyl,
$R_{23}'$ is not H, —$CH(CH_3)_2$, or —$CH_2$—CH—$(CH_3)_2$, when $R_{20}'$ is 4-aminophenyl or 4-nitrophenyl,
$R_{23}'$ is not H when $R_{20}'$ is 3-aminophenyl, 3-nitrophenyl, 2-chloropyridin-4-yl, or vinyl, or
$R_{23}'$ is not —$CH_2$—$CH_2$—S—$CH_3$ when $R_{20}'$ is pyridin-3-yl or 2-chloropyridin-4-yl, provided that when $R_{22}'=R_{23}'=R_{24}'=H$, x is zero and $X_1$ is —C(O)— and $R_{20}'$ is phenyl, $R_{25}'$ is not —CH(CH$_3$)$_2$, provided that when $R_{23}'=R_{24}'=H$, $R_{25}'$ is —CH$_2$—CH$_2$—COOH, x is zero and $X_1$ is —C(O)—, $R_{20}'$ does not form a heterocyclic ring with the adjacent nitrogen atom, and provided that when $R_{22}'=R_{23}'=R_{24}'=R_{25}'$ H, x is zero and $X_1$ is —SO$_2$—, $R_{20}'$ is not 4-methylphenyl.

Compounds of formula II' are typically selective inhibitors of cathepsin K.

In a further aspect the invention provides a compound of formula III

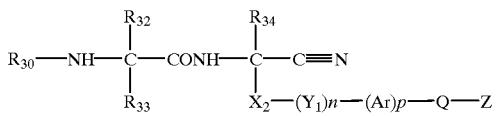

wherein $R_{30}$ is an acyl group derived from an organic carboxylic, carbonic, carbamic or sulfonic acid;

$R_{32}$ and $R_{33}$ are independently hydrogen, lower alkyl, cycloalkyl, bicycloalkyl, or (aryl, biaryl, cycloalkyl or bicycloalkyl)-lower alkyl; or $R_{32}$ and $R_{33}$ together represent lower alkylene so as to form a ring together with the carbon to which they are attached;

$R_{34}$ is hydrogen or lower alkyl; $X_2, Y_1$, Ar, Q, Z, n and p are as previously defined;

and pharmaceutically acceptable salts and esters thereof for use as a pharmaceutical.

In preferred embodiments the invention further provides a compound of formula III as defined above, wherein $R_{30}$ is an acyl group derived from an organic carboxylic, carbamic or sulfonic acid Compounds of formula III are typically selective inhibitors of cathepsin B and/or L.

Particular embodiments relate to the compounds of formula III wherein $R_{30}$, $R_{32}$, $R_{33}$, $R_{34}$, Q, Z and n are as defined above; and wherein (a) p is one;

(b) $Y_1$ is O, S, SO, SO$_2$, N(R$_6$)SO$_2$ or N—R$_6$; and (c) $X_2$ is lower alkylene; or when n is zero, $X_2$ is also $C_2$–$C_7$-alkylene interrupted by O, S, SO, SO$_2$ or NR$_6$; wherein R$_6$ is as defined above and pharmaceutically acceptable salts thereof.

Further particular embodiments relate to the compounds of formula III wherein $R_{30}$, $R_{32}$, $R_{33}$, $R_{34}$, $R_{35}$, Ar, Z and Q have meaning as defined above; and wherein (a) p is one, n is zero, and $X_2$ is lower alkylene or $C_2$–$C_7$-alkylene interrupted by O, S, SO, SO$_2$NR$_6$, NR$_6$SO$_2$, SO$_2$NR$_6$, CONR$_6$ or NR$_6$CO; or (b) p is one, n is one, $X_2$ is lower alkylene and $Y_1$ is O, S, SO, SO$_2$, N(R)SO$_2$ or NR$_6$, SO$_2$NR$_6$, CONR$_6$, NR$_6$CO; or (c) p is one, n is zero and $X_2$ is lower alkylene; or (d) p is one, n is zero and $X_2$ is $C_2$–$C_7$-alkylene interrupted by O, S, SO, SO$_2$ or NR$_6$, SO$_2$NR$_6$, CONR$_6$ or NR$_2$CO; or (e) p is zero, n is one, $X_2$ is lower alkylene and $Y_1$ is O, S, SO, SO$_2$, N(R$_6$)SO$_2$ or NR$_6$, SO$_2$NR$_{6, CONR6}$ or NR$_6$CO; or (f) p is zero, n is zero and $X_2$ is $C_2$–$C_7$-alkylene interrupted by O, S, SO, SO$_2$ or NR$_6$, SO$_2$NR$_6$, CONR$_6$ or NR$_6$CO;

and pharmaceutically acceptable salts thereof: or

Preferred compounds of formula III are those in which Z is carboxyl or carboxyl derivatized as a pharmaceutically acceptable ester.

A particular embodiment of the invention relates to the compounds of formula III wherein n is zero, in particular those of formula III'

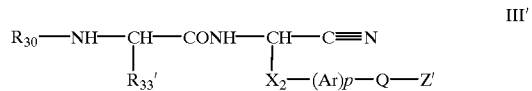

wherein $R_{30}$, $X_2$, Ar, Q, and p are as defined above; and wherein $R_{33}'$ is carbocyclic or heterocyclic aryl-lower alkyl;

Z' is hydroxy, acyloxy, carboxyl, carboxyl derivatized as a pharmaceutically acceptable ester or amide, or 5-tetrazolyl;

and pharmaceutically acceptable salts thereof.

In a specific embodiment of the compounds of formula III', $R_{30}$ is carboxylic acid derived acyl; $R_{33}'$ is carbocyclic or heterocyclic aryl-lower alkyl; $X_2$ is $C_1$–$C_5$-alkylene, or $X_2$ is $C_2$–$C_4$-alkylene interrupted by O or S; p is one; Ar is carbocyclic arylene; Q is a direct bond or $C_1$–$C_4$-alkylene; and Z is carboxyl or carboxyl derivatized as a pharmaceutically acceptable ester; and pharmaceutically acceptable salts thereof.

In a more specific embodiment of the compounds of formula III', $R_{30}$ is aroyl, $R_{33}'$ is carbocyclic aryl-methyl; $X_2$ is $C_3$-alkylene; or $X_2$ is $C_2$-alkylene interrupted by O; p is one; Ar is phenylene; Q is a direct bond; and Z is carboxyl; and pharmaceutically acceptable salts thereof.

A further particular embodiment of the invention relates to the compounds of formula III wherein n is one, in particular those of formula III''

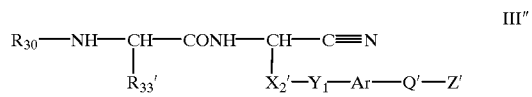

wherein $R_{30}$, $R_{33}'$, $Y_1$, Ar, and Z' are as defined above;

$X_2'$ is lower alkylene;

Q' is a direct bond or lower alkylene;

and pharmaceutically acceptable salts thereof.

A specific embodiment of the invention is directed to the compounds of formula III'' wherein $R_{30}$ is carboxylic acid derived acyl; $R_{33}'$ is carbocyclic or heterocyclic aryl-lower alkyl; $X_2'$ is$C_1$–$C_4$-alkylene; $Y_1$ is O or S; Ar is carbocyclic arylene; Q' is a direct bond or $C_1$–$C_4$-alkylene; and Z' is carboxyl or carboxyl derivatized as a pharmaceutically acceptable ester; and pharmaceutically acceptable salts thereof.

A more specific embodiment of the invention is directed to said compounds of formula III'' wherein $R_{30}$ is aroyl, $R_{33}'$ is carbocyclic aryl-methyl; $X_2'$ is $C_2$-alkylene; $Y_1$ is O; Ar is phenylene; Q' is a direct bond; and Z' is carboxyl, and pharmaceutically acceptable salts thereof.

A yet further aspect of the invention is directed to a compound of formula IV

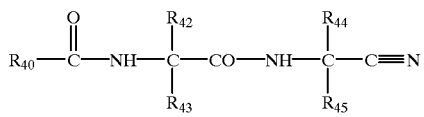

(IV)

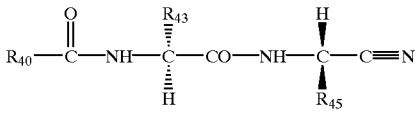

-continued

V'' wherein

R₄ (is substituted phenyl or heterocyclic aryl, (mono- or di- carbocyclic or heterocyclic aryl)-lower alkyl or lower alkenyl, or heterocyclyl;

R₄₂ is hydrogen or lower alkyl;

R₄₃ is carbocyclic or heterocyclic aryl-lower alkyl;

R₄₄ and R₄₅ are independently hydrogen or lower alkyl; or

R₄₄ and R₄₅ combined represent lower alkylene;

and pharmaceutically acceptable salts and esters thereof.

Preferred are compounds of formula IV wherein R₄₀ is morpholino, substituted phenyl or heterocyclic aryl; R₄₂ is hydrogen; R₄₃ is carbocyclic or heterocyclic aryl-lower alkyl; R₄₄ and R₄₅ are hydrogen or lower alkyl; or R₄₄ and R₄₅ combined represent ethylene to form a cyclopropyl ring.

Particularly preferred are compounds of formula IV wherein R₄₀ is pyrazolyl or pyrazolyl substituted by 1–3 lower alkyl; R₄₂ is hydrogen; R₄₃ is carbocyclic or heterocyclic aryl-C₁–C₄-alkyl; and R₄₄ and R₄₅ are hydrogen; or R₄₄ and R₄₅ combined are ethylene.

Compounds of formula IV are typically selective inhibitors of cathepsin L and/or S.

The compounds of formulae I, II, III and IV, depending on the nature of substituents, possess one or more asymmetric carbon atoms. The resulting diastereomers and enantiomers are encompassed by the instant invention. Preferably, however, e.g. for pharmaceutical use in accordance with the invention, the compounds of formulae I, II, III and IV are provided in pure or substantially pure epimeric form, e.g. as compositions in which the compounds are present in a form comprising at least 90%, e.g. preferably at least 95% of a single epimer (i.e. comprising less than 10%, e.g. preferably less than 5% of other epimeric forms).

Preferred compounds of formula I are those wherein the asymmetric carbon to which are attached R₂ and/or R₃ corresponds to that of an L-amino acid precursor and the asymmetric carbon to which is attached the cyano group also corresponds to that of an L-amino acid and is generally assigned the (S)-configuration. Preferred compounds of formula I wherein R₃ and R₄ represent hydrogen can be represented by formulae V, V' and V'', corresponding to preferred compounds of formulae II, III and IV respectively.

Thus in particularly preferred embodiments the invention provides a compound of formula V, V' or V''

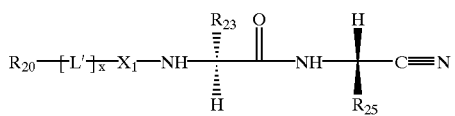

V

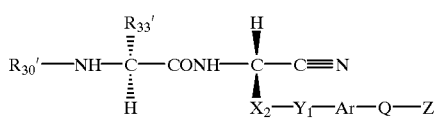

V' wherein the symbols are as defined above, and physiologically-acceptable and -cleavable esters or salts thereof.

The compounds of formula I, II, II', III, III', III'', IV, V, V' and V'' as defined above are hereinafter referred to as Compounds of the Invention.

The general definitions used herein have the following meaning within the scope of the invention, unless otherwise specified.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1–4 carbon atoms. Lower alkyl represents for example methyl, ethyl, propyl, butyl, isopropyl or isobutyl.

Lower alkenyl represents either straight chain or branched alkenyl of 2 to 7 carbon atoms, preferably 24 carbon atoms, e.g. as vinyl, propenyl, isopropenyl, butenyl, isobutenyl or butadienyl.

Lower alkynyl represents either straight chain or branched alkynyl of 2 to 7 carbon atoms, preferably 2–4 carbon atoms, e.g. as acetylenyl, propynyl, isopropynyl, butynyl or isobutynyl.

Lower alkyl, lower alkenyl and lower alkynyl may be substituted by up to 3 substituents selected from lower alkoxy, aryl, hydroxy, halogen, cyano, or trifluoromethyl.

Lower alkylene represents either straight chain or branched alkylene of 1 to 7 carbon atoms and represents preferably straight chain alkylene of 1 to 4 carbon atoms, e.g. a methylene, ethylene, propylene or butylene chain, or said methylene, ethylene, propylene or butylene chain mono-substituted by C₁–C₃-alkyl (advantageously methyl) or disubstituted on the same or different carbon atoms by C₁–C₃-alkyl (advantageously methyl), the total number of carbon atoms being up to and including 7.

A lower alkoxy (or alkyloxy) group preferably contains 14 carbon atoms, advantageously 1–3 carbon atoms, and represents for example ethoxy, propoxy, isopropoxy, or most advantageously methoxy.

Halogen (halo) preferably represents chloro or fluoro but may also be bromo or iodo.

An acyl group as represented by R₃₀ is preferably derived from an organic carbonic acid, an organic carboxylic acid, a carbamic acid or an organic sulfonic acid.

Acyl which is derived from a carboxylic acid represents, for example, carbocyclic or heterocyclic aroyl, cycloalkylcarbonyl, (oxa or thia)-cycloalkylcarbonyl, lower alkanoyl, (lower alkoxy, hydroxy or acyloxy)-lower alkanoyl, (mono- or di- carbocyclic or heterocyclic)-(lower alkanoyl or lower alkoxy-, hydroxy- or acyloxy- substituted lower alkanoyl), or biaroyl.

Carbocyclic aroyl represents, for instance, benzoyl, benzoyl substituted, by one to three substituents selected independently from e.g. halo, trifluoromethyl, lower alkyl, lower alkoxy, hydroxy, methylenedioxy, nitro, di-lower alkylamino, cyano, or carbocyclic aroyl represents e.g. 1- or 2-naphthoyl.

Heterocyclic aroyl represents, for instance, 2-, 3- or 4-pyridylcarbonyl (such as nicotinoyl), furoyl, thienoyl, oxazoloyl, isoxazoloyl, quinoxaloyl, each optionally substituted by e.g. halo, lower alkyl, lower alkoxy or nitro.

(Oxa- or thia)-cyclolalkylcarbonyl is, for example, tetrahydrofuranoyl or tetrahydrothienoyl. Dicarbocyclic or heterocyclic)aryl-lower alkanoyl is, for example, diphenylacetyl or dipyridylacetyl.

Aryl-(lower alkoxy, hydroxy or acyloxy substituted) lower alkanoyl is, for example, phenyl-(2-alkoxy, hydroxy or acyloxy)-acetyl.

Biaroyl is, for example, 2, 3 or 4-biphenylcarbonyl.

Acyl which is derived from an organic carbonic acid is, for example, alkoxycarbonyl, especially lower alkoxycarbonyl, which is unsubstituted or substituted by carbocyclic or heterocyclic aryl or is cycloalkoxycarbonyl, especially $C_3$–$C_7$-cycloalkyloxycarbonyl, which is unsubstituted or substituted by lower alkyl.

Acyl which is derived from a carbamic acid is, for example, aminocarbonyl which is optionally substituted on nitrogen by one or two of lower alkyl, carbocyclic or heterocyclic aryl-lower alkyl, carbocyclic or heterocyclic aryl, or by lower alkylene or lower alkylene interrupted by O or S.

Acyl which is derived from an organic sulfonic acid represents, for example, lower alkylsulfonyl, carbocyclic or heterocyclic arylsulfonyl, carbocyclic or heterocyclic aryl-lower alkysulfonyl, in which aryl is e.g. phenyl, naphthyl or thienyl, such being optionally substituted by, for example, lower alkyl, lower alkoxy, halo, nitro, trifluoromethyl, carboxyl or lower alkoxycarbonyl.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-$C_2$–$C_3$-alkylene; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$–$C_3$-alkylene is also a divalent substituent attached to two adjacent carbon atoms of phenyl, e.g. oxyethylene or oxypropylene. An example for oxy-$C_2$–$C_3$-alkylene-phenyl is 2,3-dihydrobenzofuran-5-yl.

Preferred as carbocyclic aryl is naphthyl, phenyl or phenyl mono- or disubstituted by lower alkoxy, phenyl, halogen, lower alkyl or trifluoromethyl, especially phenyl or phenyl mono- or disubstituted by lower alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-1-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(2-thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, by e.g. lower alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represent preferably 3-benzopyranyl or 3-benzothiopyranyl, respectively. Thiazolyl represents preferably 2- or 4-thiazolyl, advantageously 4-thiazolyl. Triazolyl is preferably 1-, 2- or 5-(1,2,4-triazolyl). Tetrazolyl is preferably 5-tetrazolyl.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted, by lower alkyl or halogen; and in particular pyridyl.

Arylene (Ar in formula III) is an aryl linking group in which aryl is heterocyclic or carbocyclic aryl, preferably monocyclic as defined above.

A heterocyclic aryl linking group is for instance (but not limited thereto) 1,3-pyrazolyl, 2,4- or 2,5-pyridyl or 1,4-imidazolyl in which the groups as depicted in formula III are attached to the ring at the indicated positions.

A carbocyclic aryl linking group is for instance (but not limited thereto) optionally substituted phenyl in which the two groups as depicted in formula I are attached ortho, meta or para to each other.

Biaryl is may be carbocyclic biaryl, preferably e.g. biphenyl, namely 2, 3 or 4-biphenyl, advantageously 4-biphenyl, each optionally substituted by e.g. lower alkyl, lower alkoxy, halogen, trifluoromethyl or cyano, or heterocyclic-carbocyclic biaryl, preferably e.g. thienylphenyl, pyrrolylphenyl and pyrazolylphenyl.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Bicycloalkyl is for example norbomanyl.

Heterocyclyl represents a saturated cyclic hydrocarbon containing one or more, preferably 1 or 2, hetero atoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino.

Aryl-lower alkyl represents preferably (carbocyclic aryl or heterocylic aryl)-lower alkyl.

Carbocyclic aryl-lower alkyl represents preferably straight chain or branched aryl-$C_{1-4}$-alkyl in which carbocyclic aryl has meaning as defined above, e.g. benzyl or phenyl-(ethyl, propyl or butyl), each unsubstituted or substituted on phenyl ring as defined under carbocyclic aryl above, advantageously optionally substituted benzyl, e.g. benzyl substituted or phenyl lay lower alkyl.

Heterocyclic aryl-lower alkyl represents preferably straight chain or branched heterocyclic aryl-$C_{1-4}$-alkyl in which heterocyclic aryl has meaning as defined above, e.g. 2-, 3- or 4-pyridylmethyl or (2, 3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4-thiazolyl)-(ethyl, propyl or butyl).

Cycloalkyl-lower alkyl represents e.g. (cyclopentyl- or cyclohexyl)-(methyl or ethyl).

Biaryl-lower alkyl represents e.g. 4-biphenylyl-(methyl or ethyl).

Acyl as in acyloxy is derived from an organic carboxylic acid, carbonic acid or carbarnic acid. Acyl represents e.g. lower alkanoyl, carbocyclic aryl-lower alkanoyl, lower alkoxycarbonyl, aroyl, di-lower alkylaminocarbonyl or di-lower alkylamino-lower alkanoyl. Preferably, acyl is lower alkanoyl.

Lower alkanoyl represents e.g. $C_{1-7}$-alkanoyl including formyl, and is preferably $C_{2-4}$-alkanoyl such as acetyl or propionyl.

Aroyl represents e.g. benzoyl or benzoyl mono- or di-substituted by one or two radicals selected from lower alkyl, lower alkoxy, halogen, cyano and trifluoromethyl; or 1- or 2-naphthoyl; and also e.g. pyridylcarbonyl.

Lower alkoxycarbonyl represents preferably $C_{1-4}$-alkoxycarbonyl, e.g. ethoxycarbonyl.

Esterified carboxyl is carboxyl derivatized as a pharmaceutically acceptable ester, for example lower alkoxycarbonyl, benzyloxycarbonyl or allyloxycarbonyl.

Amidated carboxyl is carboxyl derivatized as a pharmaceutically acceptable amide, for example aminocarbonyl, mono- or di-lower alkylaminocarbonyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The compounds of the invention exhibit valuable pharmacological properties in mammals and are particularly useful as cysteine cathepsin inhibitors.

The cathepsin inhibitory effects of the compound of the invention can be determined in vitro by measuring the inhibition of e.g. recombinant human cathepsins B, K, L and S. The buffer used in the cathepsin B, L and S assays is a 0.1 M pH 5.8 phosphate buffer containing EDTA (1.33 mM), DTT (2.7 mM) and Brij (0.03%).

The in vitro assays are carried out as follows:

(a) For cathepsin B:

To a microtiter well is added 100 uL of a 20 uM solution of inhibitor in assay buffer followed by 50 uL of a 6.4 mM solution of Z-Arg-Arg-AMC substrate (Peptides International) in assay buffer. After mixing, 50 uL of a 0.544 nM solution of recombinant human cathepsin B in assay buffer is added to the well, yielding a final inhibitor concentration of 10 uM. Enzyme activity is determined by measuring fluorescence of the liberated aminomethylcoumarin at 440 nM using 380 nM excitation, at 20 minutes. % Enzyme inhibition is determined by comparison of this activity to that of a solution containing no inhibitor. Compounds are subsequently subjected to a dose response curve analysis to determine $IC_{50}$ values.

(b) For cathepsin K:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-MCA—Peptide Institute Inc. Osaka, Japan) in 100 mM sodium phosphate buffer, pH 7.0, containing 2 mM dithiothreitol, 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively.

(c) For cathepsin L:

Recombinant human cathepsin L is activated prior to use in this assay: To 500 uL of a 510 nM solution of cathepsin L in a 50 mM pH 5.0 acetate buffer containing 1 mM EDTA, 3 mM DTT and 150 mM NaCl is added 10 uL of a 625 uM solution of dextran sulfate (ave. mw=8000), and the resulting solution is incubated on ice for 30 min. 4 uL of this solution is then diluted into 46 uL assay buffer, yielding a 40 nM enzyme solution.

To perform the assay, 100 uL of a 20 uM solution of inhibitor in assay buffer is added to a microtiter well. 50 uL of a 20 uM solution of Z-Phe-Arg-AMC (Peptides International) is then added. After mixing, 50 uL of the activated 40 nM solution of recombinant human cathepsin L in assay buffer is then added to the well, yielding a final inhibitor concentration of 10 uM. Enzyme activity is determined by measuring fluorescence of the liberated aminomethylcoumarin at 440 nM using 380 nM excitation of 20 minutes. % Enzyme inhibition is determined by comparison of this activity to that of a solution containing no inhibitor. Compounds are subsequently subjected to a dose response curve analysis to determine $IC_{50}$ values.

(d) For cathepsin S:

To a microtiter well is added 100 uL of a 20 uM solution of inhibitor is assay buffer. 50 uL of a 700 uM solution of Z-Val-Val-Arg-AMC substrate (Peptides International) is then added. After mixing, 50 uL of a 5.2 nM solution of recombinant human cathepsin S in assay buffer is then added to the well, yielding a final inhibitor concentration of 10 uM. Enzyme activity is determined by measuring fluorescence of the liberated aminomethylcoumarin at 440 nM using 380 nM excitation at 200 minutes. % Enzyme inhibition is determined by comparison of this activity to that of a solution containing no inhibitor. Compounds are subsequently subjected to a dose response curve analysis to determine $IC_{50}$ values.

In view of their activity as inhibitors of cysteine cathepsin enzymes, Compounds of the Invention are particularly useful in mammals as agents for treatment and prophylaxis of diseases and medical conditions involving elevated levels of cathepsins. Such diseases include diseases involving infection by organisms such as pneumocystis carinii, trypsanoma cruzi, trypsanoma brucei, crithidia fusiculata, as well as parasitic diseases such as schistosomiasis and malaria, tumours (tumour invasion and tumour metastasis), and other diseases such as metachromatic leukodystrophy, muscular dystrophy, amytrophy and similar diseases.

Cathepsins, in particular K, have been implicated in diseases of excessive bone loss, and thus the Compounds of the Invention may be used for treatment and prophylaxis of such diseases, including osteoporosis, gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation.

Compounds of the Invention, are also indicated for preventing or treating coronary disease, atherosclerosis (including atherosclerotic plaque rupture and destabilization), autoimmune diseases, respiratory diseases and immunologically mediated diseases (including transplant rejection).

Compounds of the Invention, in particular cathepsin K selective inhibitor compounds, are particularly indicated for preventing or treating osteoporosis of various genesis (e.g. juvenile, menopausal, post-menopausal, post-traumatic, caused by old age or by cortico-steroid therapy or inactivity).

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule formulation. The dosage in vitro may range between about $10^{-5}$ molar and $10^{-9}$ molar concentrations. The dosage in vivo may range, depending on the route of administration, between about 0.1 and 100 mg/kg.

The antiarthritic efficacy of the compounds of the invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Arth. Rheum. 1993 26, 875–886). The efficacy of the compounds in the model can be quantified using histological scoring methods, as described previously (O'Byme et al. Inflamm Res 1995, 44, S117–S118).

The efficacy of the compounds of the invention for the treament of osteoporosis can be determined using an animal model such as the ovarectomised rat or other similar species in which test compounds are administered to the animal and the presence of markers of bone resorption are measured in urine or serum.

The compounds of the invention are prepared by:

(a) converting an amide of the formula VI

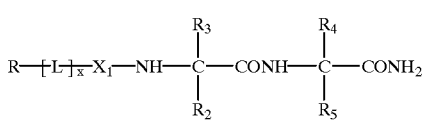

VI wherein R, $R_2$, $R_3$, $R_4$ and $R_5$ have meaning as previously defined for the compounds of formula I to a nitrile of formula I; or (b) condensing a compound of the formula VII

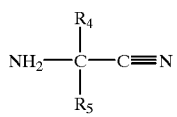

VII wherein $R_4$ and $R_5$ have meaning as defined hereinabove, with an acid of formula VIII

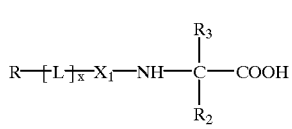

VIII wherein R, $R_2$ and $R_3$ have meaning as defined above; or with a reactive derivative thereof; or (c) condensing a compound of the formula Ia

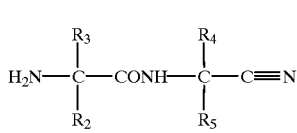

(Ia)

wherein $R_2$, $R_3$, $R_4$ and $R_5$ have meaning as defined hereinabove with an acid corresponding to the group R—[L]$_x$—X— or with a reactive derivative thereof; and in the above processes, if required, temporarily protecting any interfering reactive groups and then isolating the resulting compound of the invention; and, if desired, converting any resulting compound into another compound of the invention; and/or if desired, converting a resulting compound into a salt or a resulting salt into the free acid or base or into another salt.

Appropriate protecting groups are used for starting compounds and intermediates, for instance as hereinafter described in the Examples.

The conversion of primary amides of formula V to the nitrites of formula I, according to process (a), can be carried out according to methods well known in the art for the dehydration of a primary amide to a nitrile, e.g. with thionyl chloride in the presence of a base. A preferred procedure involves the treatment with oxalyl chloride and pyridine in DMF at or below room temperature as illustrated in the examples.

The starting materials of formula VI can be prepared by condensing an amino acid amide of formula IX

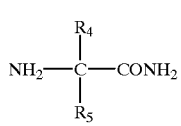

IX wherein $R_4$, and $R_5$ have meaning as defined above with an acid of the formula VIII, in protected form as appropriate.

The condensation can be carried out according to methods well-known in the art, e.g. by reacting a mixed anhydride or an acyl halide of the acid of formula VIII e.g. the acid chloride, with an amino acid amide of formula IX, in an inert solvent such as methylene chloride, in the presence of a base, such as an amine like triethylamine or pyridine.

The acylation of an acid of formula VIII with an amino acid amide of formula IX can also be carried out in the presence of a condensing agent such as N-(3-dimethylaminopropyl)-N'-ethylcarbodiimide, optionally in the presence of e.g. hydroxybenzotriazole or 1-hydroxy-7-azabenzotriazole, and a base such as N-methylmorpholine.

The amino acid amides of formula IX are either known or can be prepared according to methodology known in the art and illustrated herein.

Alternative procedures and conditions may be used; for instance as described in the Examples.

Compounds of the invention are either obtained in the free form, or as a salt thereof if salt forming groups are present.

Acidic Compounds of the Invention may be converted into metal salts with pharmaceutically acceptable bases, e.g. an aqueous alkali metal hydroxide, advantageously in the presence of an ethereal or alcoholic solvent, such as a lower alkanol. Resulting salts may be converted into the free compounds by treatment with acids. These or other salts can also be used for purification of the compounds obtained. Ammonium salts are obtained by reaction with the appropriate amine, e.g. diethylamine, and the like.

Compounds of the Invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal, transdermal, topical, and parenteral administration to mammals, including man, to inhibit cathepsin activity, and for the treatment of cathepsin dependent disorders, in particular inflammation, osteoporosis, rheumatoid arthritis and osteoarthritis, and comprise an effective amount of a pharmacologically active compound of the invention, alone or in combination, with one or more pharmaceutically acceptable carriers.

More particularly, the pharmaceutical compositions comprise an effective cathepsin inhibiting amount of a Compound of the Invention.

The pharmacologically active Compounds of the Invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Matrix transdermal formulations may also be used.

Suitable formulations for topical application, e.g. to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin inhibiting amount of a Compound of the Invention as defined above, either alone or in combination with another therapeutic agent.

In conjunction with another active ingredient, a Compound of the Invention may be administered either simultaneously, before or after the other active ingredient, either separately by the same or different route of administration or together in the same pharmaceutical formulation. The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

The present invention also relates to methods of using Compounds of the Invention and their pharmaceutically acceptable salts, or pharmaceutical compositions thereof, in mammals for inhibiting cathepsins, such as cathepsin B, K, L and/or S, and for the treatment of cathepsin dependent conditions, such as cathepsin B, K, L and/or S dependent conditions, described herein, e.g. inflammation, osteoporosis, rheumatoid arthritis and osteoarthritis.

Particularly the present invention relates to a method of selectively inhibiting cathepsin activity in a mammal which comprises administering to a mammal in need thereof an effective cathepsin inhibiting amount of a Compound of the Invention.

More specifically such relates to a method of treating rheumatoid arthritis, osteoarthritis, and inflammation (and other diseases as identified above) in mammals comprises administering to a mammal in need thereof a correspondingly effective amount of a Compound of the Invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Example 1
Preparation of Indol4-yl-C(O)-Leu-Gly(CN) of formula X

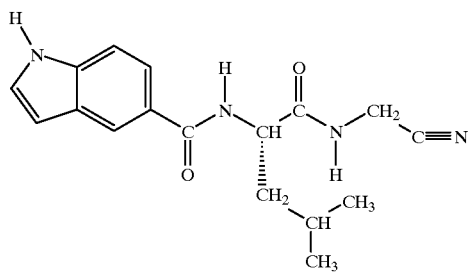

A. Fmoc-Leu-Gly(CN)
[1-(Cyanomethyl-carbamoyl)-3-methyl-butyl]-carbamic acid 9.H.-fluoren-9-yl methyl ester Fmoc-Leucine (0.27 mmol) and aminoacetonitrile hydrochloride (32.4 mmol) are dissolved in dimethylformamide (300 ml) and cooled with ice-salt. HOBt (32.4 mmol) and WSCD (32.4 mmol) are added, and the reaction mixture is stirred at 4–25° C. over night. After evaporation of the solvent, the residue is extracted with ethyl acetate. The extract is washed with saturated sodium bicarbonate, 1N hydrochloric acid and brine, dried over magnesium sulfate and the solvent is evaporated. Chromatography on silica gel using n-hexane/ethyl acetate=1/1 (v/v) gives the product in 90% yield.

mp. 173–175° C., Rf=0.68 (chloroform:methanol:acetic acid=90:10:1).

B. H-Leu-Gly(CN)
2-Amino-4-methyl-pentanoic acid cyanomethyl-amide

Fmoc-Leu-Gly(CN) (18 mmol) is dissolved in 20% piperidine in dimethylformamide (36 ml). The reaction mixture is stirred at room temperature for 60 min. After evaporation of the solvent and chromatography on silica gel using n-hexane, n-hexane/ethyl acetate=1/1 and 10% methanol in chloroform, the product is obtained in 93% yield.

oil, Rf=0.73 (n-propanol:water:ethyl acetate:ammonia= 5:1:2:1).

C. Indol-5-yl-C(O)-Leu-Gly(CN)

Indol-5-ylcarboxylic acid (1.0 eq.) and H-Leu-Gly(CN) (1.2 eq.) are dissolved in dimethylformamide and cooled with ice-salt. HOBt (1.2 eq.) and WSCD (1.2 eq.) are added and the reaction mixture is stirred at 4–25° C. over night. After ethyl acetate is added to the reaction mixture, the organic layer is washed with saturated sodium bicarbonate, 1N hydrochloric acid and brine, dried over magnesium sulfate and evaporated. Chromatography on silica gel gives the title product in 70% yield.

mp. 201–204° C., Rf=0.39 (n-hexane:AcOEt=1:2)

Example 2
5-Aminoquinoline-2-carboxylic acid [1-(cyanomethyl-carbamoyl)-3-methyl-butyl]-amide 5-Nitro-quinoline-2-carboxylic acid [1-(cyanomethyl-carbamoyl)-3-methyl-butyl]-amide (0.35 mmol) is dissolved in tetrahydrofuran (10 ml) and methanol (10 ml) at room temperature. $Na_2S_2O_4$ aq * (7 mmol) is added to the solution, and the reaction mixture is heated at reflux for 90 min. The crude product is isolated by filtration and purified by chromatography on silica gel using 2% methanol in chloroform. The product is obtained in 33% yield. mp. 190–194° C., Rf=0.60 (n-hexane:ethyl acetate=1:5). * A. S. Kende et al., Tetrahedron Lett., 25, 923–926, (1984).

Example 3
p-Acetamidomethylbenzoyl-Leu-Gly(CN)

p-Aminomethylbenzoyl-Leu-Gly(CN) (see Example 14 below)(0.33 mmol) and acetic acid (3.3 mmol) are dissolved in dimethylformamide (10 ml) and cooled in an ice bath. HOBt (0.4 mmol) and WSCD (0.4 mmol) are added and the reaction mixture is stirred at 4–25° C. over night. After evaporation of the solvent, the residue is extracted with ethyl acetate. The extract is washed with saturated sodium bicarbonate, 1N hydrochloric acid and brine, dried over magnesium sulfate and evaporated. Diethylether is added to the residue to give a precipitate, which is collected by filtration and precipitated again from ethyl acetate with diethylether to give the product in 32% yield.

mp. 176–184.5° C., Rf=0.24 (chloroform:methanol=9:1).

By repeating the procedures described in the above Examples using appropriate starting materials and conditions the following compounds of formula XI are obtained as identified below in Table 1.

TABLE 1
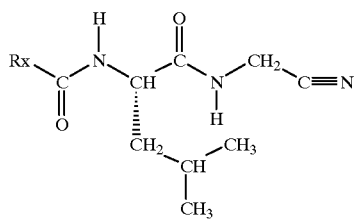
| Example No. | Rx | mp. (° C.) | Rf (solvent) |
|---|---|---|---|
| 4 | 4-methylindole | 52–70 | 0.24 (n-hexane:AcOEt = 1:1) |
| 5 | 3-methylindole | 150–160 | 0.30 (n-hexane:AcOEt = 1:2) |
| 6 | 2-methylindole | 170–194 | 0.77 (n-hexane:AcOEt = 1:2) |
| 7 | 2-methylnaphthalene | 169–184.5 | 0.43 (n-hexane:AcOEt = 1:1) |
| 8 | 2-methylanthracene | 210–235.5 | 0.39 (n-hexane:AcOEt = 1:1) |
| 9 | 2-methylquinoline | 174.5–176.5 | 0.48 (n-hexane:AcOEt = 1:2) |
| 10 | 5-nitro-2-methylquinoline | 163–167 | 0.42 (n-hexane:AcOEt = 1:1) |
| 11 | 2-methylanthraquinone | 234–242 | 0.43 (n-hexane:AcOEt = 1:1) |

TABLE 1-continued

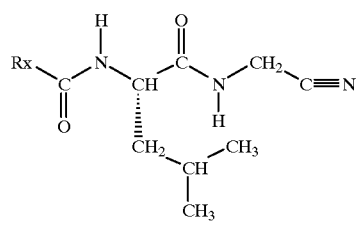

XI

| Example No. | Rx | mp. (° C.) | Rf (solvent) |
|---|---|---|---|
| 12 | 2-quinoxalinyl | 156–158.5 | 0.31 (n-hexane:AcOEt = 1:1) |
| 13 | 4-biphenylyl | 191.5–199 | 0.45 (n-hexane:AcOEt = 1:1) |
| 14 | 4-(aminomethyl)phenyl (H₂NCH₂-C₆H₄-) | 57–64 | 0.80 (n-hexane:AcOEt = 1:2) |
| 15 | 3-(aminomethyl)phenyl | | 0.31 (chloroform:MeOH = 7:3) |
| 16 | 4-aminophenyl | 89–95 | 0.61 (n-hexane:AcOEt = 1:2) |
| 17 | 2-aminophenyl | 223–224 | 0.23 (n-hexane:AcOEt = 1:2) |
| 18 | 3-aminophenyl | 143–144 | 0.70 (n-hexane:AcOEt = 1:2) |
| 19 | 4-(2-thienyl)phenyl | | 0.33 (n-hexane:AcOEt = 1:1) |
| 20 | 4-(3-thienyl)phenyl | | 0.47 (n-hexane:AcOEt = 1:1) |
| 21 | CH₃-O-CH₂-CH₂-NH-CH₂-C₆H₄- | 122–126 | 0.18 (CH₂Cl₂:MeOH = 9:1) |

TABLE 1-continued

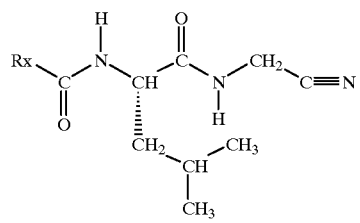

XI

| Example No. | Rx | mp. (° C.) | Rf (solvent) |
|---|---|---|---|
| 22 | HO—CH₂—CH₂—NH—CH₂—C₆H₄—CH₃ | oil | 0.17 (CH₂Cl₂/MeOH/NH₃ = 9:1) |
| 23 | imidazol-1-yl-CH₂-(4-methylphenyl) | 248–250 | 0.35 (CH₂Cl₂/MeOH = 9:1) |
| 24 | morpholin-4-yl-CH₂-(4-methylphenyl) | 136–138 | 0.21 (CH₂Cl₂/MeOH = 95:5) |
| 25 | pyrrolidin-1-yl-CH₂-(4-methylphenyl) | 225–227 | 0.10 (CH₂Cl₂/MeOH = 9:1) |
| 26 | CH₃O—CH₂—CH₂—N(CH₃)—CH₂-(4-methylphenyl) | 97–99 | 0.41 (CH₂Cl₂/MeOH = 9:1) |
| 27 | imidazol-1-yl-CH₂-(3-methylphenyl) | 164–168 | 0.27 (CH₂Cl₂/MeOH = 9:1) |
| 28 | morpholin-4-yl-CH₂-(3-methylphenyl) | 114–116 | 0.16 (CH₂Cl₂/MeOH = 95:5) |
| 29 | pyrrolidin-1-yl-CH₂-(3-methylphenyl) | <70 | 0.16 (CH₂Cl₂/MeOH = 9:1) |
| 30 | CH₃O—CH₂—CH₂—N(CH₃)—CH₂-(3-methylphenyl) | 89–91 | 0.19 (CH₂Cl₂/MeOH = 9:1) |

Example 31

Indole-2-carboxylic acid {1-[(cyano-dimethyl-methyl)-carbamoyl]-cyclohexyl}-amide A. Fmoc-1-aminocyclohexane carboxylic acid The title compound is prepared from 1-cyclohexane carboxylic acid (7 mmol), Fmoc-Cl (7.7 mmol) and NaOH (14 mmol) in the usual manner in 18% yield. Rf=0.17 (n-hexane:ethyl acetate=1:2).

B. Boc-2-Aminoisobutyric acid amide

28% aqueous ammonia (66 mmol) is added to the mixed anhydride (prepared from 22 mmol of Boc-2-aminobutyric acid and 22 mmol of iso-butylchoroformate by customary procedures) at −20° C. The reaction mixture is stirred at 4–25° C. overnight. After evaporation of the solvent, the residue is extracted with ethyl acetate. The extract is washed with saturated sodium bicarbonate, 1N hydrochloric acid and brine, dried over magnesium sulfate and evaporated. The crude product is purified by chromatography on silica gel using n-hexane/ethyl acetate=1/1 and n-hexane/ethyl acetate=1/2, to give the product in 31% yield.

mp. 168–177.5° C., Rf=0.41 (chloroform:methanol=9:1).

C. 2-Aminobutyric acid amide hydrochloride

Boc-2-Aminoisobutyric acid amide is dissolved in 4N hydrochloride in dioxane. The reaction mixture is stirred at room temperature for 60 min. Diethylether is added to the solution to give a white precipitate, which is collected in 91% yield by filtration. The crude product is used for the next coupling without further purification.

Rf=0.28 (n-PrOH:H$_2$O:ethyl acetate:NH3=5:1:2:1).

D. Fmoc-1-Amino-cyclohexanecarboxylic acid (1-carbamoyl-1-methyl-ethyl)-amide

Fmoc-1-aminocyclohexane carboxylic acid (2.2 mmol) and 2-aminobutyric acid amide hydrochloride (2.2 mmol) are dissolved in dimethylformamide (30 ml) and cooled with ice-salt. HOBt (2.6 mmol) and WSCD (2.6 mmol) are added and the reaction mixture is stirred at 4–25° C. over night. After evaporation of the solvent, the residue is extracted with ethyl acetate. The extract is washed with saturated sodium bicarbonate, 1N hydrochloric acid and brine, dried over magnesium sulfate and evaporated. The crude product is purified by chromatography on silica gel using n-hexane/ethyl acetate=1/4 and n-hexane/ethyl acetate=1/6, to give the product in quantitative yield.

mp. 177.5–178.5° C., Rf=0.24 (n-hexane:ethyl acetate=1:5)

E. Fmoc-1-Amino-cyclohexanecarboxylic acid (cyano-dimethyl-methyl)-amide Thionyl chloride (2.6 mmol) is added to the solution of Fmoc-1-amino-cyclohexanecarboxylic acid (1-carbamoyl-1-methyl-ethyl)-amide (0.86 mmol) in dimethylformamide (10 ml) at 4° C. The reaction mixture is stirred at 4° C. for 2 h., ethyl acetate and saturated sodium bicarbonate solution are added and the organic layer is washed with brine, dried over magnesium sulfate and evaporated. The crude product is purified by chromatography on silica gel using n-hexane/ethyl acetate=3/1, to give the product in quantitative yield.

Rf=0.57 (n-hexane:ethyl acetate=1:1).

F. 1-Amino-cyclohexanecarboxylic acid (cyano-dimethyl-methyl)-amide

Fmoc-1-Aminocyclohexanecarboxylic acid (cyano-dimethyl-methyl)-amide (2.1 mmol) is dissolved in 20% piperidin in dimethylformamide (6.3 ml). The reaction mixture is stirred at room temperature for 60 min. After evaporation of the solvent, the crude product is purified by chormatography on silica gel using n-hexane, n-hexane/ethyl acetate=1/1 and 10% methanol in chloroform, to give the product in 31% yield. oil, Rf=0.84 (n-propanol:water:ethyl acetate:ammonia=5:1:2:1)

G. Indole-2-carboxylic acid {1-[(cyano-dimethyl-methyl)-carbamoyl]-cyclohexyl}-amide 2-Indole carboxylic acid (0.61 mmol) and 1-amino-cyclohexanecarboxylic acid (cyano-dimethyl-methyl)-amide (0.61 mmol) are dissolved in dimethylformamide (15 ml) and cooled in an ice bath. HOBt (0.61 mmol) and WSCD.HCI (0.61 mmol) are added and the reaction mixture is stirred at 4–25° C. over night. After evaporation of the solvent, the residue is extracted with ethyl acetate. The extract is washed with saturated sodium bicarbonate, 1N hydrochloric acid and brine, dried over magnesium sulfate and evaporated. The crude product is purified by chromatography on silica using n-hexane/ethyl acetate=4/1 and n-hexane/ethyl acetate=2/1, to give the product in 71% yield.

mp. 200–202° C., Rf=0.55 (n-hexane:ethyl acetate=1:1)

Example 32

Synthesis of Naphthalene-2-carboxylic acid [1-(cyanomethyl-carbamoyl)-2-methyl-butyl]-amide A. 2-tert-Butyloxycarbonylamino-3-methyl-pentanoic acid cyanomethyl-amide N-Tertbutyloxycarbonyl-isoleucine semihydrate (3 g, 12.5 mmol), HOBt (3.71 g, 27.5 mmol, 2.2 eq.) and aminoacetonitrile hydrochloride (1.27 g, 13.7 mmol, 1.1 eq.) are dissolved in dimethylformamide (36 ml) and WSCD (2.5 ml, 13.7 mmol, 1.1 eq.) is added. After stiring for 1 hour at rt, 4% sodium bicarbonate solution is added and the mixture is extracted with ethyl acetate. The organic layer is washed with sodium bicarbonate and dilute hydrochloric acid, dried over magnesium sulfate and evaporated, to give the product in quantitative yield.

mp. 125–133.5° C., Rf=0.44 (hexanes:ethyl acetate=1:1)

B. 2-Amino-3-methyl-pentanoic acid cyanomethyl-amide hydrochloride 2-tert-Butyloxycarbonylamino-3-methyl-pentanoic acid cyanomethyl-amide (2 g, 7.4 mmol) is dissolved in 4N hydrochloride in dioxane (10 ml). After 15 min. at rt the solvent is evaporated to give the product in quantitative yield. The crude product is used for the next step without further purification.

Rf (free amine)=0.33 (ethyl acetate:methanol=10:1)

C. Naphthalene-2-carboxylic acid [1-(cyanomethyl-carbamoyl)-2-methyl-butyl]-amide 2-Naphthoylchloride (255 mg, 1.34 mmol, 1.1 eq.) is added to the solution of 2-amino-3-methyl-pentanoic acid cyanomethyl-amide hydrochloride (250 mg, 1.22 mmol) and triethylamine (0.42 ml, 3.04 mmol, 2.5 eq.) in 5 ml dichloromethane. After 1 hour at rt 1 N hydrochloric acid is added and the reaction mixture is extracted with ethyl acetate. The organic layer is washed with saturated sodium bicarbonate solution, dried over magnesium sulfate and evaporated. Chromatography on silica gel (hexane/ethyl acetate 10/1 to 5/1, followed by ethyl acetate) gives the product in 97% yield (381 mg).

mp. 203.5–207° C., Rf=0.44 (hexanes:ethyl acetate=1:1).

Example 33

Synthesis of Naphthalene-2-carboxylic acid [1-(1-cyano-3-methyl-butylcarbamoyl)-2-methyl-butyl]-amide A. N-(Naphthalene-2 carbonyl)-isoleucine methylester L-isoleucine methylester hydrochloride (2.0 g, 11.0 mmol) and triethylamine (3.1 ml, 22.0 mmol, 2 eq.) are dissolved in dichloromethane (40 ml). The solution is cooled in an icebath and 2-naphthoylchloride (2.1 g, 11.0 mmol, 1 eq.) is added. The reaction mixture is allowed to warm up to rt and after 1 hour 1N hydrochloric acid is added. The mixture is extracted with ethyl acetate, the organic layer is washed with saturated sodium bicarbonate solution, dried over magnesium sulfate and evaporated to give the product in 98% yield.

Rf=0.50 (hexanes:ethyl acetate=2:1)

B. N-(Naphthalene-2-carbonyl)-isoleucine

N-(Naphthalene-2-carbonyl)-isoleucine methylester (3.14 g, 10.5 mmol) is stirred in a mixture of methanol (35 ml) and 1 N aqueous sodium hydroxide (16.8 ml, 1.6 eq.). After 3 hours at rt the mixture is heated for 1 hour at 40° C. 1 N hydrochloric acid and brine is added and the mixture is extracted with ethyl acetate. The organic layer is dried over magnesium sulfate and evaporated to give the product in quantitative yield (partly epimerized).

Rf=0.32 (hexane:ethyl acetate=1:2)

C. (S)-1-Cyano-3-methyl-butylamine hydrochloride (S)-N-tert-Butyloxycarbonyl-1-cyano-3-methyl-butylamine (CAS 115654-59-6) (3.7 g, 17.4 mmol) is dissolved in 4N hydrogenchloride in dioxane (20 ml). After 15 minutes at rt the solvent is evaporated, the residue is taken up in diethylether, the solid is filtered and dried in vacuum to give the product in 81% yield.

Rf (free amine)=0.34 (hexane:ethyl acetate=1:1)

D. Naphthalene-2-carboxylic acid [1-(1-cyano-3-methyl-butylcarbamoyl)-2-methyl-butyl]-amide N-(Naphthalene-2-carbonyl)-isoleucine (250 mg, 0.87 mmol), (S)-1-cyano-3-methyl-butylamine (143 mg, 0.96 mmol, 1.1 eq.) and HOBt (260 mg, 1.93 mmol, 2.2 eq.) are dissoved in dimethylformamide (5 ml) and WSCD (0.17 ml, 0.96 mmol, 1.1 eq.) is added. After stirring for 1 hour at rt, 4% sodium bicarbonate solution is added and the mixture is extracted with ethyl acetate. The organic layer is washed with sodium bicarbonate and dilute hydrochloric acid, dried over magnesium sulfate and evaporated. Chromatography on silica gel (hexane/ethyl acetate 2/1) gives the product in 68% yield (mixture of epimers).

Rf=0.43 (hexanes:ethyl acetate=2:1)

Example 34

Synthesis of Naphthalene-2-carboxylic acid [1-(1-cyano-3-methyl-butylcarbamoyl)-3-methyl-butyl]-amide A. N-(Naphthalene-2 carbonyl)-leucine The title compound is prepared analogously is prepared similar to N-(Naphthalene-2-carbonyl)-isoleucine (see above) in 98% yield, starting from leucine methylester.

Rf=0.34 (hexanes:ethyl acetate=1:1)

B. Naphthalene-2-carboxylic acid [1-(1-cyano-3-methyl-butylcarbamoyl)-3-methyl-butyl]-amide N-(Naphthalene-2-carbonyl)-leucine (250 mg, 0.88 mmol), (S)-1-cyano-3-methyl-butylamine (143 mg, 0.96 mmol, 1.1 eq.) and HOBt (260 mg, 1.93 mmol, 2.2 eq.) are dissovled in dimethylformamide (5 ml) and WSCD (0.18 ml, 0.97 mmol, 1.1 eq.) is added. After stiring for 1 hour at rt, 4% sodium bicarbonate solution is added and the mixture is extracted with ethyl acetate. The organic layer is washed with sodium bicarbonate and dilute hydrochloric acid, dried over magnesium sulfate and evaporated. Chromatography on silica gel (hexane/ethyl acetate 2/1) gives the product in 79% yield (mixture of epimers).

Rf=0.44 (hexane:ethyl acetate=2:1)

Example 35

Naphthalene-2-carboxylic acid {1-[1-cyano-2-(1H-indol-3-yl)-ethylcarbamoyl]-3-methyl-butyl}-amide The title compound is prepared analogously to the compound of Example 22. N-(Naphthalene-2-carbonyl)-leucine and 1-cyano-2-(1H-indol-3-yl)-ethylamine (CAS 169545-97-5) are reacted by the same procedure as for Naphthalene-2-carboxylic acid [1-(1-cyano-3-methyl-butylcarbamoyl)-3-methyl-butyl]-amide, to give the product in 36% yield after chromatography on silica gel (hexane/ethyl acetate 1/1) (mixture of epimers).

Rf=0.59 (hexane:ethyl acetate=1:1)

Example 36

Naphthalene-2-carboxylic acid[1-(1-cyano-1-methyl-ethylcarbamoyl)-3-methyl-butyl]-amide A. N-tert-Butyloxycarbonyl-1-cyano-1-methyl-ethylamine

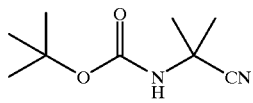

Boc-2-aminoisobutyric acid amide(4.58 g, 22.6 mmol) and triethylamine(7 ml, 50 mmol, 2.2 eq.) are dissolved in THF (100 ml) and trifluoroacetic acid anhydride (3.5 ml, 25 mmol, 1.1 eq.) is added at 0. The reaction mixture is stirred at 0° for 1 hour.The mixture is concentrated and water is added. The organic layer is extracted with ethyl acetate, washed with brine, dried over sodium sulfate and evaporated. The crude product is purified by chromatography on silica gel using n-hexane/ethyl acetate=20/1, 10/1, 5/1 and 1/1 to give the product in 74% yield.

Rf=0.45 (n-hexane/ethyl acetate=3/1)

B. 1-Cyano-1-methyl-ethylamine hydrochloride

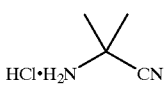

B. N-tert-Butyloxycarbonyl-1-cyano-1-methyl-ethylamine (3.09 g, 16.8 mmol) is dissolved in dioxane (15 ml) and 4N hydrochloric acid-dioxane (25 ml) is added at 0°. The reaction mixture is stirred at 0° for 1.5 hours, then at rt for 1 hour. The mixture is concentrated and diethyl ether is added. The resulting white precipitate is washed with diethyl ether and dried to give the product in 83% yield. The crude product is used for the next coupling without further purification.

Rf=0.66(n-PrOH/H$_2$O/ethyl acetate/NH$_{3=5/1/2/1}$)

C. Naphthalene-2-carboxylic acid[ 1-(1-cyano-1-methyl-ethylcarbamoyl)-3-methyl-butyl]-amide

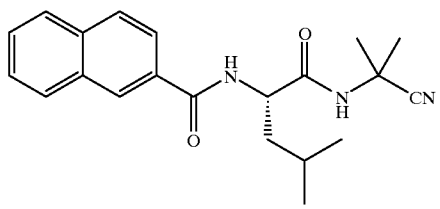

N-(Naphthalene-2-carbonyl)-leucine (279 mg, 0.98 mmol), 1-cyano-1-methyl-ethylamine hydrochloride (137 mg, 1.14 mmol, 1.2 eq.) and HOBt (297 mg, 2.20 mmol, 2.2 eq.) are dissolved in dimethylformamide (5 ml) and WSCD (0.2 ml, 1.09 mmol, 1.1 eq.) is added at 10°. After stirring for 1.5 hours at −10°, 5% sodium bicarbonate solution is added and the mixture is extracted with ethyl acetate. The organic layer is washed with brine, dried over sodium sulfate and evaporated. Chromatography on silica gel (n-hexane/ethyl acetate=20/1, 10/1, 5/1, 3/1 and 1/1) gives the product in 8.7% yield (mixture of enantiomers).

Rf=0.54 (n-hexane/ethyl acetate=1/1)

Example 37

Naphthalene-2carboxylic acid[1-(1-cyano-4-phenyl-propylcarbamoyl)-3-methyl-butyl]-amide A. Boc-2-Amino-4-phenyl-butyric acid amide Boc-Hph-CONH2

31

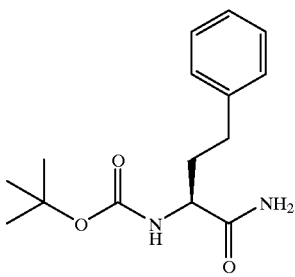

28% aqueous ammonia (34 mmol) is added to the mixed anhydride (prepared from 16,8 mmol of Boc-homophenylalanine and 17.0 mmol of isobutylchloroformate as usual) at −10. The reaction mixture is stirred at rt for 4.5 hours. The mixture is concentrated, washed with saturated sodium bicarbonate, 1N hydrochloric acid and brine, dried over sodium sulfate and evaporated to give the product in quantitative yield. The crude product is used for the next reaction without further purification.
Rf=0.60 (chloroform/mathanol=10/1)
Thereafter the title compound

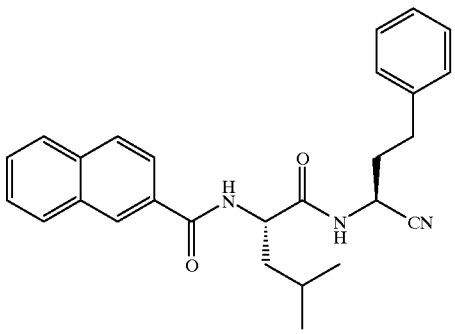

is prepared analogously as in steps A, B and C of Example 36
Rf=0.81 (n-hexane/ethyl acetate 1/1)

Example 38
Naphthalene-2-carboxylic acid[ 1-(1-cyano-4-phenyl-propylcarbamoyl)-cyclohexyl]-amide
A. Naphthalene-2-carboxylic acid[(1-methoxycarbonyl) cyclohexyl]-amide

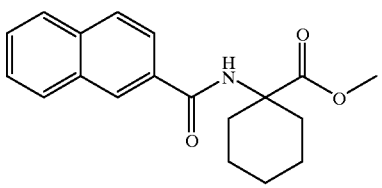

1-Amino-cyclohexanecarboxylic acid methyl ester hydrochloride (1 g, 5.2 mmol) and triethylamine (1.44 ml, 10.3 mmol, 2 eq.) are dissolved in dichloromethane (15 ml) and 2-naphthoyl chloride (1 g, 5.2 mmol, 1 eq.) is added at 0°. The reaction mixture is stirred at 0°–25° for 2 hours and hydrochloric acid is added. The mixture is extracted with ethyl acetate, the organic layer is washed with saturated sodium bicarbonate solution, dried over sodium sulfate and evaporated. Chromatography on silica gel (n-hexane/ethyl acetate=10/1, 5/1, 3/1 and 1/1) gives the product in 93% yield.

32

Rf=0.30 (n-hexane/ethyl acetate=3/1)
B. N-(2-Naphthoyl)-1-amino-cyclohexanecarboxylic acid

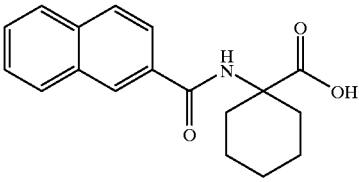

Starting from Naphthalene-2-carboxylic acid[(1-methoxycarbonyl)-cyclohexyl]-amide, the product is prepared analogously to N-(naphthalene-2-carbonyl)-isoleucine in quantitative yield. It is used for the next coupling without further purification.
Rf=0.60 (chloroform/methanol=10/1)
C. Naphthalene-2-carboxylic acid[ 1-(1-cyano-4-phenyl-propylcarbamoyl)-cyclohexyl]-amide

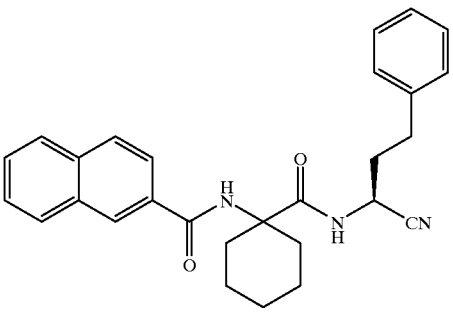

N-(2-Naphthoyl)-1-amino-cyclohexanecarboxylic acid (67 mg, 0.22 mmol), 1-cyano-3-phenyl-propylamine hydrochloride (47 mg, 0.24 mmol, 1.1 eq.) and HOAt (65 mg, 0.48 mmol, 2.2 eq.) are dissolved in dimethylformamide (2 ml) and WSCD (0.044 ml, 0.24 mmol, 1.1 eq.) is added at −10° After stirring at 0°–25° overnight, 5% sodium bicarbonate solution is added and the mixture is extracted with ethyl acetate. The organic layer is washed with brine, dried over sodium sulfate and evaporated. Chromatography on silica gel (chloroform/acetone=200/1 and 100/1) gives the product in 63% yield.
Rf=0.73 (chloroform/acetone=9/1)

Example 39
1.H.-Indole-5-carboxylic acid [1-(cyanomethyl-carbamoyl)-cyclohexyl]-amide
1-Amino-cyclohexancarboxylic acid cyanomethyl-amide (136 mg, 0.50 mmol), indol-5-carboxylic acid (80 mg, 0.50 mmol, 1.0 eq.) and HOBt (74 mg, 0.55 mmol, 1.1 eq.) are dissoved in dimethylformamide (5 ml) and WSCD (0.10 ml, 0.55 mmol, 1.1 eq.) is added. After stirring for 20 hour at rt, 4% sodium bicarbonate solution is added and the mixture is extraced with ethyl acetate. The organic layer is washed with sodium bicarbonate, dried over magnesium sulfate and evaporated. Chromatography on silica gel (hexanes/ethyl acetate 2/1, then ethyl acetate) gives the product in 20% yield.
Rf=0.31 (hexanes/ethyl acetate=3/1)

Example 40
Synthesis of N-[1-(cyanomethyl-carbamoyl)-cyclohexyl]-4-imidazol-1-ylmethyl-benzamide
A. Boc-1-aminocyclohexane carboxylic acid The title compound is prepared from 1-cyclohexane carboxylic acid (140 mmol), Boc$_2$O (154 mmol) and Na$_2$CO$_3$ (140 mmol) in 200 ml dioxane and 100 ml water by conventional methods. Mp. 157–161° C.; Rf=0.23 (CH$_2$Cl$_2$/MeOH=95:5)

B. Boc-1-amino-cyclohexanecarboxylic acid (1-(cyanomethyl-carbamoyl)-amide

Boc-1-aminocyclohexane carboxylic acid (40 mmol), HOBt (40 mmol) and WSCD (42 mmol) are dissolved in dimethylformamide (75 ml) and stirred for 15 min. at RT. 2-aminoacetonitrile hydrochloride (40 mmol) and triethylamine (40 mmol) are suspended in DMF (25 ml) and added to the reaction mixture which is stirred at 25° C. over night. After evaporation of the solvent, the residue is extracted with ethyl acetate. The extract is washed with water, 10% citric acid, brine, sodium bicarbonate, brine and dried over magnesium sulfate and evaporated. The residue is suspended in diethylether and the solid filtered of and dried (vacuum). 7.35 g of a white powder with mp. 160–162° C., Rf=0.28 (n-hexane:ethyl acetate=1:1) is obtained.

C. 1-Amino-cyclohexanecarboxylic acid (1-(cyanomethyl-carbamoyl)-amide hydrochloride HCl in Diethylether (3–4N, 50 ml) is added to the solution Boc-1-amino-cyclohexane-carboxylic acid (1-(cyanomethyl-carbamoyl)-amide (33 mmol) in THF (50 ml) at RT and stirred overnight. The reaction mixture is cooled with an ice bath to 0–4° C. and the solid filtered off and washed with diethylether. The white crystals are dried (vacuum). Mp. 205–209° C.; Rf=0.45 (CH$_2$Cl$_2$/MeOH=9:1).

D. N-[1-(cyanomethyl-carbamoyl)-cyclohexyl]-4-bromomethyl-benzamide

4-Bromomethyl-benzoic acid (2.3 mmol) is suspended in CH$_2$Cl$_2$ (7 ml) and cooled to 0–5° C. Chlorenamine (2.3 mmol) is added and the mixture is stirred for 45 min. at 0–5° C. 1-Amino-cyclohexanecarboxylic acid (1-(cyanomethyl-carbamoyl)-amide hydrochloride (2.3 mmol) and N-ethyldiisopropyl-amine (4.6 mmol) in CH$_2$Cl$_2$ (7 ml) is added at low temperature. The mixture is stirred for 2 hours at 0–5° C. and at RT over night. The reaction mixture is diluted with CH$_2$Cl$_2$ (40 ml), washed with water and dried over magnesium sulfate and evaporated. The residue was suspended in diethylether and the solid filtered of. The crude product is purified by chromatography on silica using CH$_2$Cl$_2$/MeOH97:3. The fractions containing the pure product were collected and evaporated. The residue was suspended in diethylether and the solid filtered of A white powder with mp. 194–196° C., Rf=0.38 (CH$_2$Cl$_2$/MeOH=95:5) is obtained.

E. N-[1-(cyanomethyl-carbamoyl)-cyclohexyl]-4-imidazol-1-ylmethyl-benzamide

N-[1-(cyanomethyl-carbamoyl)-cyclohexyl]-4-bromomethyl-benzamide (0.34 mmol) is dissolved in THF (2 ml) and sodium-imidazol (0.41 mmol) is added and the reaction mixture stirred at RT over night. After evaporation of the solvent, the residue is extracted with ethyl acetate. The extract is washed with water, dried over magnesium sulfate and evaporated. The residue was suspended in diethylether and the solid filtered of. The crude product is purified by chromatography on silica using CH$_2$Cl$_2$/MeOH=9:1. The fractions containing the pure product were collected and evaporated. The residue was suspended in diethylether and the solid filtered of. A white powder with mp. 194–196° C., Rf=0.28 (CH$_2$Cl$_2$/MeOH=9:1) is obtained.

By repeating the procedure described above in Examples 40, using appropriate starting materials and reaction conditions the following compounds of formula XII are obtained as identified below in Table 2.

TABLE 2

XII

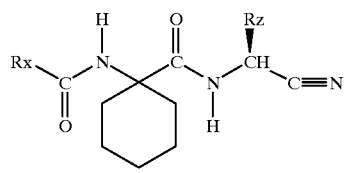

| Example No. | Rx | Rz | mp. (° C.) | Rf (solvent) MS (M + 1) |
|---|---|---|---|---|
| 41 | 2-naphthyl | CH(CH$_3$)$_2$ | | 0.26 (hexanes/EtOAc = 3/1) |
| 42 | 2-naphthyl | indol-3-ylmethyl (CH$_2$) | | 0.50 (hexanes/EtOAc = 1/1) |
| 43 | CH$_3$O—CH$_2$—CH$_2$—N(CH$_3$)—CH$_2$—(4-methylphenyl) | H | 126–128 | 0.19 (CH$_2$Cl$_2$/MeOH = 9:1) |

TABLE 2-continued

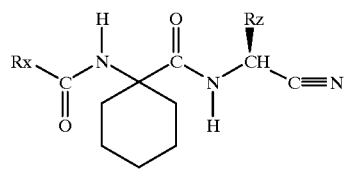

XII

| Example No. | Rx | Rz | mp. (° C.) | Rf (solvent) MS (M + 1) |
|---|---|---|---|---|
| 44 | (1-imidazolyl-CH₂-phenyl-CH₃, meta) | H | 162–165 | 0.27 (CH₂Cl₂/MeOH = 9:1) |
| 45 | CH₃O—CH₂—CH₂—N(CH₃)—CH₂-(3-methylphenyl) | H | 147–149 | 0.24 (CH₂Cl₂/MeOH = 9:1) |
| 46 | 2-methylnaphthyl | —CH₂—CH(CH₃)₂ | | 0.26 (hexanes/EtOAc = 3/1) |
| 47 | " | 3-indolyl-CH₂— | | 0.50 (hexanes/EtOAc = 1/1) |
| 48 | 5-methylindolyl | H | | 0.31 (hexanes/EtOAc = 3/1) |
| 49 | 4′-methylbiphenyl | —CH₂—CH(CH₃)₂ | | 0.31 (n-hexane/EtOAc = 2/1) |
| 50 | 1-(4-methylphenyl)pyrrole | " | | 0.42 (n-hexane/EtOAc = 2/1) |
| 51 | 4-methylphenyl-C(O)—CH₃ (4-methylacetophenone) | " | | 0.42 (n-hexane/EtOAc = 2/1) |

TABLE 2-continued
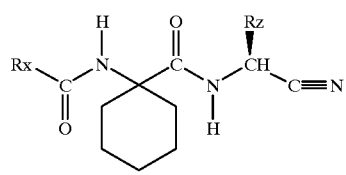
XII
| Example No. | Rx | Rz | mp. (° C.) | Rf (solvent) MS (M + 1) |
|---|---|---|---|---|
| 52 | 1,2-dimethylindol-3-yl | " | | 0.42 (n-hexane/EtOAc = 2/1) |
| 53 | 1-(4-methylphenyl)pyrrol-2-yl | H | | 0.69 (EtOAc) |
| 54 | 2-methylbenzofuran-3-yl | " | | 0.69 (EtOAc) |
| 55 | 2-methylindol-3-yl | —CH$_2$CH(CH$_3$)$_2$ | | 0.58 (n-hexane/EtOAc = 1/1) |
| 56 | 4-acetylphenyl | H | | 0.47 (EtOAc) |
| 57 | 2-methylindol-3-yl | H | | 0.72 (EtOAc) |
| 58 | 1,2-dimethylindol-3-yl | " | | 0.73 (EtOAc) |
| 59 | 4'-fluorobiphenyl-4-yl | " | | 0.66 (EtOAc) |

TABLE 2-continued

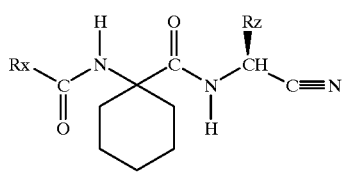

XII

| Example No. | Rx | Rz | mp. (° C.) | Rf (solvent) MS (M + 1) |
|---|---|---|---|---|
| 60 | 4-methoxy-4'-methylbiphenyl group | " | | 0.66 (EtOAc) |
| 61 | 4-(tert-butoxy)-4-methylphenyl group | " | | 0.67 (EtOAc) |
| 62 | benzyloxymethyl group | benzyloxymethyl group | | 0.24 (toluene/acetone 7/3) 436 |
| 63 | 2-methylbenzofuran group | 4-methoxybenzyl group | 199–201 | 446 |
| 64 | 1,2-dimethylindol-3-yl group | " | 184–185 | 459 |
| 65 | 2-methylindol-3-yl group | " | | 0.14 (CH$_2$Cl$_2$/MeOH 10/0.2) 445 |
| 66 | " | benzyloxymethyl group | | 0.54 (petroleum ether/EtOAC 1/1) |
| 67 | 2-phenyl-5-methylpyrrolo[1,2-a]pyrimidine group | " | 154–155 | 522 |

Example 68

Synthesis of N-{1-[(Cyano-dimethyl-methyl)-carbamoyl]-3-methyl-butyl}-4-imidazol-1-ylmethyl-benzamide A. {1-[(Cyano-dimethyl-methyl)-carbamoyl]-3-methyl-butyl}-carbamic acid .tert.-butyl ester Boc-Leu-OH (62 mmol), HOBt (62 mmol) and WSCD (62 mmol) are dissolved in dimethylformamide (150 ml) and stirred for 15 min. at RT. 2-Amino-2-methyl-propionamide hydrochloride (62 mmol) and triethylamine (62 mmol) are suspended in DMF (25 ml) and added to the reaction mixture which is stirred at 25° C. over night. After evaporation of the solvent, the residue is extracted with ethyl acetate. The extract is washed with water, 10% citric acid, brine, sodium bicarbonate, brine and dried over magnesium sulfate and evaporated. The residue is suspended in diethylether and the solid filtered of and dried (vacuum). 14.78 g of a white powder with mp. 182–184° C., Rf=0.39 (CH$_2$Cl$_2$/MeOH= 9:1) is obtained.

B. {1-[(Cyano-dimethyl-methyl)-carbamoyl]-3-methyl-butyl}-carbamic acid .tert.-butyl ester {1-[(Cyano-dimethyl-methyl)-carbamoyl]-3-methyl-butyl}-carbamic acid .tert.-butyl ester (47 mmol) is dissolved in THF (150 ml) and cooled to −10° C. Trifluoro-acetic acid anhydride (56 mmol) and triethylamine (94 mmol) are added at −10° C. and the stirred mixture is slowly warmed up to 0° C. over 2 hours. After evaporation of the solvent, the residue is extracted with ethyl acetate. The extract is washed with water and dried over magnesium sulfate and evaporated. The residue is suspended in diethylether/pentane and the solid filtered of and dried (vacuum). 9.93 g of a white powder with mp. 166–168° C., Rf=0.55 (n-hexane:ethyl acetate=1:1) is obtained.

C. 2-Amino-4-methyl-pentanoic acid (cyano-dimethyl-methyl)-amide

{1-[(Cyano-dimethyl-methyl)-carbamoyl]-3-methyl-butyl}-carbamic acid .tert.-butyl ester (19 mmol) is dissolved in ethyl acetate containing HCl (3–4N, water free) and the mixture is stirred at RT overnight. After evaporation of the solvent, the crude product is purified by chromatography on silica using CH$_2$Cl$_2$/MeOH=9:1. The fractions containing the pure product were collected and evaporated. 2.3 g of a yellowish oil, Rf=0.36 (CH$_2$Cl$_2$/MeOH=9:1) is obtained.

D. N-{1-[(Cyano-dimethyl-methyl)-carbamoyl]-3-methyl-butyl}-4-bromometyl-benzamide 4-Bromomethylbenzoic acid (4.1 mmol), HOBt (4.1 mmol) and WSCD.HCl (4.1 mmol) are dissolved in dimethylformamide (7 ml) and stirred for 10 min. 2-Amino-4-methyl-pentanoic acid (cyano-dimethyl-methyl)-amide (4.1 mmol) is added in DMF (3 ml) and the reaction mixture is stirred at RT overnight. After evaporation of the solvent, the residue is extracted with ethyl acetate. The extract is washed with water, 10% citric acid, brine, sodium bicarbonate, brine and dried over magnesium sulfate and evaporated. The crude product is suspended in diethylether and the solid filtered of and dried (vacuum). A white powder with mp. 185–187° C., Rf=0.43 (n-hexane:ethyl acetate=1:1) is obtained.

E. N-{1-[(Cyano-dimethyl-methyl)-carbamoyl]-3-methyl-butyl}-4-imidazol-1-ylmethyl-benzamide N-{1-[(Cyano-dimethyl-methyl)-carbamoyl]-3-methyl-butyl}-4-bromomethyl-benzamide (0.18 mmol) is dissolved in THF (1 ml) and sodium-imidazol (0.41 mmol) is added and the reaction mixture stirred at RT over night. After evaporation of the solvent, the residue is extracted with ethyl acetate. The extract is washed with water, dried over magnesium sulfate and evaporated. An oil with Rf=0.44 (CH$_2$Cl$_2$/MeOH=9:1) is obtained.

By repeating the procedure described above in Examples 68, using appropriate starting materials and conditions the following compounds of formula XIII are obtained as identified below in Table 3.

TABLE 3

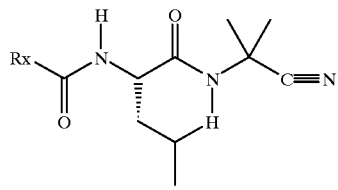

XIII

| Example No. | Rx | yield (%) (step B) | mp. (° C.) | Rf (solvent) |
|---|---|---|---|---|
| 69 | CH$_3$O—CH$_2$—CH$_2$—N(CH$_3$)—CH$_2$—C$_6$H$_4$— | 58 | 135–137 | 0.29 (CH$_2$Cl$_2$/MeOH = 9:1) |
| 70 | 4-methylpiperazin-1-ylmethyl-phenyl | 51 | 160–162 | 0.16 (CH$_2$Cl$_2$/MeOH = 9:1) |
| 71 | pyrrolidin-1-ylmethyl-phenyl | 44 | 186–188 | 0.23 (CH$_2$Cl$_2$/MeOH = 9:1) |

Example 72

N-[1-(Cyanomethyl-carbamoyl)-3-methyl-butyl]-4-(2-pyrrolidin-1-yl-ethylsulfanyl)-benzamide A. 4-(2-Chloroethylsulfanyl)-benzoic acid 4-Mercaptobenzoic acid (65 mmol) and 1-Bromo-2-chloro-ethane (71 mmol) are dissolved in acetone (120 ml) and powdered potassium carbonate (71 mmol) is added. The mixture is warmed up to 40° C. and stirred for 7 hours. After evaporation of the solvent, the residue is extracted with ethyl acetate. The extract is washed with water and dried over sodium sulfate and evaporated. The crude product is suspended in diethylether and the solid filtered of and dried (vacuum). 7.8 g of a white powder with mp. 142–144° C., Rf=0.37 (methylenchlorid/methanol=9/1) is obtained.

B. 4-(2-Chloroethylsulfanyl)-benzoyl-Leu-Gly(CN)

4-(2-Chloroethylsulfanyl)-benzoic acid (18.5 mmol), HOBt (18.5 mmol) and WSCD.HCI (19.4 mmol) are dissolved in dimethylformamide (50 ml) and stirred for 15 min. H-Leu-Gly((CN) (18.5 mmol) is added and the reaction mixture is stirred at RT overnight. After evaporation of the solvent, the residue is extracted with ethyl acetate. The extract is washed with water, 10% citric acid, brine, sodium bicarbonate, brine and dried over magnesium sulfate. After evaporation of the solvent, the crude product is purified by chromatography on silica using $CH_2Cl_2$/MeOH=95:5. The fractions containing the pure product were collected and evaporated. The product is suspended in diethylether and the solid filtered of and dried (vacuum). 3.15 g of a yellowish powder with mp. 108–110° C., Rf=0.33 (n-hexane:ethyl acetate=1:1) is obtained.

C. N-[1-(Cyanomethyl-carbamoyl)-3-methyl-butyl]-4-(2-pyrrolidin-1-yl-ethylsulfanyl)-benzamide 4-(2-Chloroethylsulfanyl)-benzoyl-Leu-Gly(CN) (1.36 mmol) is dissolved DMF (2 ml) and pyrrolidine (3 mmol) is added. The reaction mixture is stirred for 8 hours at RT, then a catalytic amount of potassium iodide is added and again stirred at 50° C. overnight. After evaporation of the solvent, the residue is extracted with ethyl acetate. The extract is washed with water and dried over magnesium sulfate and evaporated. The crude material is applied to a column of silica gel. Elution with $CH_2Cl_2$/MeOH=93:7 gives the product in 24% yield (Rf=0.12 ($CH_2Cl_2$/MeOH=95:5).

Example 73

Synthesis of N-[1-(Cyanomethyl-carbamoyl)-3-methyl-butyl]-4-(2-pyrrolidin-1-yl-ethylsulfonyl)-benzamide A. 4-(2-Chloroethylsulfonyl)-benzoic acid 4-(2-Chloroethylsulfanyl)-benzoic acid (18.4 mmol) is suspended in methylene chloride (60 ml) and cooled to −10C. m-Chloroperbenzoic acid (38.6 mmol) are added dropwise in methylene chloride (60 ml) and the mixture is stirred for e hours at −10° C. The mixture is diluted methylene chloride (100 ml) and a 5% solution of sodium thiosulfate in water is added and the mixture vigorously stirred. The mixture is extracted, washed with water and and dried over sodium sulfate and evaporated. The crude product is recrystallized from ethylacetate and the solid filtered of and dried (vacuum). 2.19 g of a pale powder with mp. 142–144° C., Rf=0.37 ($CH_2Cl_2$/MeOH=9:1) is obtained.

B. 4-(2-Chloroethylsulfonyl)-benzoyl-Leu-Gly(CN)

4-(2-Chloroethylsulfonyl)-benzoic acid (8.8 mmol), HOBt (8.8 mmol) and WSCD.HCI (8.8 mmol) are dissolved in dimethylformamide (25 ml) and stirred for 15 min. H-Leu-Gly((CN) (18.5 mmol) is added and the reaction mixture is stirred at RT overnight. After evaporation of the solvent, the z residue is extracted with ethyl acetate. The extract is washed with water, 10% citric acid, brine, sodium bicarbonate, brine and dried over magnesium sulfate. After evaporation of the solvent, the crude product is purified by chromatography on silica using $CH_2Cl_2$/MeOH=95:5. The fractions containing the pure product were collected and evaporated. The product is suspended in diethylether and the solid filtered of and dried (vacuum). 0.3 g of a white powder, Rf=0.25 ($CH_2Cl_2$/MeOH=95:5) is obtained.

C. N-[1-(Cyanomethyl-carbamoyl)-3-methyl-butyl]-4-(2-pyrrolidin-1-yl-ethylsulfonyl)-benzamide 4-(2-Chloroethylsulfonyl)-benzoyl-Leu-Gly(CN) (0.4 mmol) is in pyrrolidine (1 ml. The reaction mixture is stirred for 1.5 hours at RT. After evaporation of the solvent, the residue is extracted with ethyl acetate. The extract is washed with water and dried over magnesium sulfate and evaporated. The crude material is applied to a column of silica gel. Elution with $CH_2Cl_2$/MeOH=95:5 gives the product in 43% yield (Rf=0.30 ($CH_2Cl_2$/MeOH=95:5).

Example 74

Synthesis of N-[1-(1-Cyano-3-methyl-butylcarbamoyl)-3-methyl-butyl]-4-imidazol-1-ylmethyl-benzamide A. Boc-Leu-Leu-NH2

Boc-Leu-Leu-OH (Bachem, 43.6 mmol) is dissolved in THF (250 ml) and N-methylmorpholine (43.6 mmol) is added. The mixture is cooled to −20° C. and isobutyl chloroformate (43.6 mmol) is added dropwise. The mixture is stirred for 10 min. and then a 25% aqueous solution of ammonia (52.3 mmol) is added at −20° C. The mixture is stirred for 3 hours at −20° C. to −10° C. After evaporation of the solvent, the residue is extracted with ethyl acetate. The extract is washed with water and dried over magnesium sulfate and evaporated. The crude product is suspended in diethylether and the solid filtered of and dried (vacuum). 14.2 g of a white powder with mp. 155–156° C., Rf=0.5 ($CH_2Cl_2$/MeOH=9:1) is obtained.

B. Boc-Leu-Leu(CN)

Boc-Leu-Leu-NH2 (41 mmol) is suspended in THF (200 ml) and triethylamine (83 mmol) and trifluoroacetic acid anhydride (41 mmol) is added at −5° C. The mixture is stirred for 2 hours at −5° C. After evaporation of the solvent, the residue is extracted with ethyl acetate. The extract is washed with water and dried over magnesium sulfate and evaporated. A yellowish oil with Rf=0.59 (n-hexane:ethyl acetate=2:1) is obtained and deprotected without further purification (step C.).

C. H-Leu-Leu(CN)

Boc-Leu-Leu(CN) (41 mmol) is dissolved in THF (50 ml) and HCl in diethylether (50 ml, 3–4N, water-free) is added at RT and the mixture stirred overnight. After evaporation of the solvent the residue is dissolved in methanol and ammonia in methanol (40 ml, 3–4N, water-free) is added and the solid material filtered of. The filtrate is evaporated and the crude product is purified by chromatography on silica using $CH_2Cl_2$/MeOH=95:5. The fractions containing the pure product were collected and evaporated. 5.07 g of a yellowish oil with Rf=0.43 ($CH_2Cl_2$/MeOH=9:1) is obtained.

D. 4-Bromomethylbenzoyl-Leu-Leu(CN)

4-Bromomethylbenzoic acid (6.67 mmol), HOBt (6.67 mmol) and WSCD.HCI (7.0 mmol) are dissolved in dimethylformamide (15 ml) and stirred for 15 min. H-Leu-Leu(CN) (6.67 mmol) is added and the reaction mixture is stirred for 2.5 hours at RT. After evaporation of the solvent, the residue is extracted with ethyl acetate. The extract is washed with water, 10% citric acid, brine, sodium bicarbonate, brine and dried over magnesium sulfate. After evaporation of the solvent, the crude product is purified by chromatography on silica using $CH_2Cl_2$/MeOH=97:3. The fractions containing the pure product were collected and evaporated. 1.74 g of a yellowish oil with Rf=0.59 ($CH_2Cl_2$/MeOH=95:5) is obtained.

E. N-[1-(1-Cyano-3-methyl-butylcarbamoyl)-3-methyl-butyl]-4-imidazol-1-ylmethyl-benzamide 4-Bromomethylbenzoyl-Leu-Leu(CN) (1.23 mmol) is dissolved in THF (5 ml) and sodium-imidazol (1.48 mmol)

is added and the reaction mixture stirred at RT over night. After evaporation of the solvent, the residue is extracted with ethyl acetate. The extract is washed with water, dried over magnesium sulfate and evaporated. The crude product is purified by chromatography on silica using $CH_2Cl_2$/MeOH=95:5. The fractions containing the pure product were collected and evaporated. The product is suspended in diethylether and the solid filtered of and dried (vacuum). A white powder with mp. 100–103° C., Rf=0.36 ($CH_2Cl_2$/MeOH=9:1) is obtained.

By repeating the procedure described above in Example 74, using appropriate starting materials and conditions the following compounds of formula XIV are obtained as identified below in Table 4.

B. [1-(2-Benzyloxy-1-carbamoyl-ethylcarbamoyl)-3-methyl-butyl]-carbamic acid benzyl ester To a solution of 0.980 g of 3-benzyloxy-2-(2-benzyloxycarbonylamino-4-methyl-pentanoylamino)-propionic acid and 0.25 ml of N-methylmorpholine in 12 ml of tetrahydrofuran 0.3 ml of isobutylchloroformate is added dropwise at −15° C. The reaction mixture is stirred at −15° C. for 10 minutes, then 4 ml of aqueous $NH_3$ (25%) is added dropwise over a time period of 5 minutes. The reaction mixture is stirred for additional 15 minutes and diluted with ethyl acetate. Ethyl acetate is washed once with saturated $NH_4Cl$-solution and once with $H_2O$, then dried sodium sulfate, the solvent is removed und the residue is triturated with diethylether.

TABLE 4

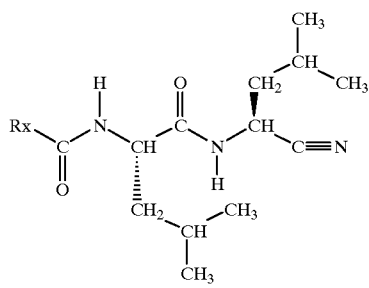

XIV

| Example No. | Rx | yield (%) (step B) | mp. (° C.) | Rf (solvent) |
|---|---|---|---|---|
| 75 | $CH_3O-CH_2-CH_2-N(CH_3)-CH_2-$(p-tolyl) | 45 | — | 0.17 ($CH_2Cl_2$/MeOH = 95:5) |
| 76 | (4-methylpiperazin-1-yl)-$CH_2$-(p-tolyl) × HCl | 51 | — | 0.23 ($CH_2Cl_2$/MeOH = 9:1) |
| 77 | (pyrrolidin-1-yl)-$CH_2$-(p-tolyl) | 64 | — | 0.31 ($CH_2Cl_2$/MeOH = 9:1) |

Example 78
[1-(2-Benzyloxy-1-cyano-ethylcarbamoyl)-3-methyl-butyl]-carbamic acid benzyl ester A. 3-Benzyloxy-2-(2-benzyloxycarbonylamino-4-methyl-pentanoylamino)-propionic acid To a suspension of 0.975 g H-Ser(OBzl)-OH in 5 ml of methylene chloride is added 1.52 ml of trimethylchlorosilane. After ten minutes at room temperature 0.98 ml of N,N-diisopropylethyl amine and 1.81 g of benzyloxy leucine N-hydroxysuccinimidester is added. The reaction mixture is stirred for 2 hours at room temperature and diluted with ethyl acetate. Ethyl acetate is washed once with saturated $NH_4Cl$-solution and once with $H_2O$, then dried over sodium sulfate, the solvent is removed and the residue is crystallized from diethylether.

$^1$H-NMR ($CDCl_3$, ppm): 7.30 (m, 10H), 6.83 (d, 1H), 5.32 (d, 1H), 5.10 (s, 2H), 4.71 (m, 1H), 4.50 (s, 2H), 4.28 (m, 1H), 3.92 (m, 1H), 3.67 (m, 1H), 1.46–1.79 (m, 3H), 0.92 (d, 6H).

$^1$H-NMR ($CDCl_3$, ppm): 7.38 (m, 10H), 6.87 (d, 1H), 6.60 (m (br.), 1H), 5.41 (m (br.), 1H), 5.12 (m (br.), 1H), 5.12 (d, 1H), 5.08 (s, 2H), 4.50 (d, 2H), 4.20–3.92 (m, 2H), 3.50 (m, 1H), 1.70–1.41 (m, 3H), 0.90 (d, 6H).

C. [1-(2-Benzyloxy-1-cyano-ethylcarbamoyl)-3-methyl-butyl]-carbamic acid benzyl ester 0.3 ml of trifluoroacetic acid anhydride is added dropwise to a solution of 0.9 g of [1-(2-benzyloxy-1-carbamoyl-ethylcarbamoyl)-3-methyl-butyl]-carbamic acid benzyl ester and 0.6 ml of triethylamine in 15 ml of tetrahydrofuran at −5° C. The reaction mixture is stirred at −5° C. for 3 hours and then for 12 hours at room temperature. The reaction mixture is then poured into $H_2O$ and the aqueous layer is extracted three times with ethyl acetate. The combined organic layers are washed once with $H_2O$ and once with brine, then dried over sodium sulfate, the solvent is removed and the residue is crystallized from diethylether/hexane. Mp.: 126–127° C.

The following compounds formula XV, as identified in Table 5 below, are prepared analogously to the compound of Example 78.

TABLE 5

XV

[Structure: Cbz-NH-CH(CH2CH(CH3)2)-C(=O)-NH-CH(Rz)-C≡N]

| Example No. | Rz | mp. (° C.)<br>MS (M + 1) |
|---|---|---|
| 79 | -CH2-C(=O)-O-CH2-C6H5 | 100–101° |
| 80 | -CH2-(2-naphthyl) | 157–158° |
| 81 | -C(=O)-O-CH2-C6H5 | 157–158° |
| 82 | -CH2-(1-naphthyl) | 159–161° |
| 83 | -CH2-CH2-C6H5 | 106–107° |
| 84 | -CH2-(4-OCH3-C6H4) | 126–127°<br>424 |
| 85 | -CH2-(4-OCH2CH3-C6H4) | 144–146<br>438 |

Example 86
2-[2-(4-Chloro-phenylamino)-acetylamino]-4-methyl-pentanoic acid cyanomethyl-amide

(4-Chloro-phenylamino)-acetic acid (0.5 g) and H-Leu-Gly((CN)).HCl (0.55 g) are dissolved in dimethylformamide (4 ml). HOBt (0.44 g), WSCD.HCl (0.54 g), triethylamine (0.37 ml) is added and the reaction mixture is stirred for 18 hours. After evaporation of the solvent, the residue is extracted with ethyl acetate. The extract is washed with 10% citric acid, brine, sodium bicarbonate, brine and dried over magnesium sulfate and evaporated. The crude product is slurried in diethylether and the solid filtered of and dried (vacuum) yielding a white powder with mp. 131–134° C.

By repeating the procedure described above in Example 86, using appropriate starting materilas and conditions the following compounds of formula XVI are obtained as identified below in Table 6.

TABLE 6

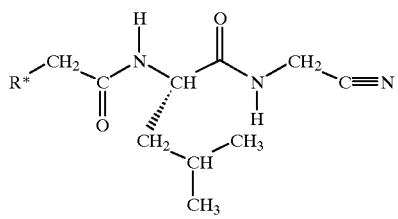

XVI

| Example No. | R* | mp. (° C.) | Rf (solvent) |
|---|---|---|---|
| 87 | 3,4-dichlorophenyl-NH- | foam | 0.32 (CH2Cl2/MeOH = 95:5) |
| 88 | 3-chlorophenyl-NH- | 110–115 | |
| 89 | 4-methoxyphenyl-NH- | foam | 0.30 (CH2Cl2/MeOH = 95:5) |
| 90 | 4-methylphenyl-NH- | 130–133 | |
| 91 | 1-naphthyl-NH- | amorph | 0.42 (CH2Cl2/MeOH = 95:5) |
| 92 | 2-naphthyl-NH- | 131–133 | |
| 93 | 3,4-dichlorophenyl-O- | 108–110 | |
| 94 | 4-chlorophenyl-O- | Resin | 0.43 (CH₂Cl₂/MeOH = 95:5) |

TABLE 6-continued

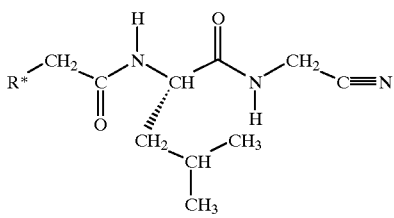

XVI

| Example No. | R* | mp. (° C.) | Rf (solvent) |
|---|---|---|---|
| 95 | 3-Cl, 3-OMe phenyl | 77–79 | |
| 96 | 1,4-dimethoxyphenyl | Oil | |
| 97 | 4-methyl, methoxyphenyl | Resin | 0.53 (CH2Cl2/MeOH = 95:5) |
| 98 | 2-methoxynaphthyl | foam | 0.47 (CH2Cl2/MeOH = 95:5) |
| 99 | 1-methoxynaphthyl | 143–146 | |
| 100 | 4-methoxybiphenyl | 119–121 | |
| 101 | 3-methoxypyridyl | Resin | 0.26 (CH$_2$Cl$_2$/MeOH = 95:5) |
| 102 | 2-methylthionaphthyl | 146–149 | |

By repeating the procedures described in the above Examples using appropriate starting materials and reaction conditions the following compounds of formula XVII are obtained as identified below in Table 7.

TABLE 7

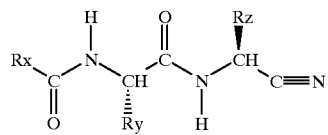

XVII

| Example No. | Rx | Ry | Rz | mp. (° C.) | Rf (solvent)/MS (M + 1) |
|---|---|---|---|---|---|
| 103 | 3-methylnaphthalene | isobutyl (CH(CH3)CH2CH3) | H | 203.5–207 | 0.44 (hexanes/EtOAc = 1/1) |
| 104 | " | isobutyl (CH2CH(CH3)2) | isobutyl (CH2CH(CH3)2) | | 0.44 (hexanes/EtOAc = 2/1) |
| 105 | 2-methylbenzofuran | " | 3-indolylmethyl | | 0.52 (n-hexane/EtOAc = 1/1) |
| 106 | 3-methylquinoxaline | " | " | | 0.45 (n-hexane/EtOAc = 1/1) |
| 107 | 5-methoxy-2-methylindole | " | isobutyl (CH2CH(CH3)2) | | 0.30 (n-hexane/EtOAc = 3/1) |
| 108 | 2-methylindole | " | " | | 0.40 (n-hexane/EtOAc = 2/1) |
| 109 | " | " | 3-indolylmethyl | | 0.24 (n-hexane/EtOAc = 4/3) |
| 110 | 4-methylbiphenyl | " | isobutyl (CH2CH(CH3)2) | | 0.36 (n-hexane/EtOAc = 2/1) |

TABLE 7-continued

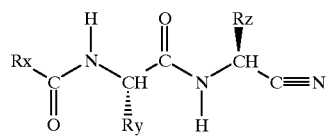

XVII

| Example No. | Rx | Ry | Rz | mp. (° C.) | Rf (solvent)/MS (M + 1) |
|---|---|---|---|---|---|
| 111 | 4-(methylsulfonyl)phenylmethyl | " | " | | 0.17 (n-hexane/EtOAc = 1/1) |
| 112 | 4-(pyrrol-1-yl)phenylmethyl | " | " | | 0.27 (n-hexane/EtOAc = 1/1) |
| 113 | (indol-3-yl)methyl | " | H | | 0.45 (EtOAc) |
| 114 | 4-acetylphenylmethyl | " | " | | 0.58 (EtOAc) |
| 115 | (1,2-dimethylindol-3-yl) | " | " | | 0.28 (n-hexane/EtOAc = 1/1) |
| 116 | 4-(methylthio)phenylmethyl | " | $CH_2CH(CH_3)CH_3$ | | 0.46 (n-hexane/EtOAc = 1/1) |
| 117 | (1,2-dimethylindol-3-yl) | " | " | | 0.41 (n-hexane/EtOAc = 2/1) |
| 118 | 2-phenyl-4,5-dimethyl-2H-1,2,3-triazol-yl | " | H | | 0.79 (EtOAc) |

TABLE 7-continued

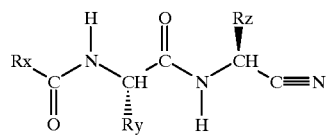

XVII

| Example No. | Rx | Ry | Rz | mp. (° C.) | Rf (solvent)/MS (M + 1) |
|---|---|---|---|---|---|
| 119 | 2-methylbenzofuran | " | " | | 0.74 (EtOAc) |
| 120 | 4'-methyl-4-methoxybiphenyl | " | isobutyl (CH₂CH(CH₃)₂) | | 0.52 (n-hexane/EtOAc = 1/1) |
| 121 | 2-phenyl-4,5-dimethyl-2H-1,2,3-triazole | " | " | | 0.60 (n-hexane/EtOAc = 1/1) |
| 122 | 4-(methylthio)benzyl | " | H | | 0.60 (EtOAc) |
| 123 | 4-(tert-butoxy)-methylbenzyl | " | isobutyl | | 0.54 (n-hexane/EtOAc = 1/1) |
| 124 | " | " | H | | 0.26 (n-hexane/EtOAc = 1/1) |
| 125 | 1-(4-methylphenyl)pyrrole | " | 4-methoxybenzyl | | 0.41 (n-hexane/EtOAc = 1/1) |
| 126 | 2-methylindole | " | " | | 0.43 (n-hexane/EtOAc = 1/1) |

TABLE 7-continued

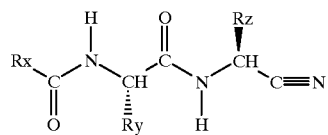

XVII

| Example No. | Rx | Ry | Rz | mp. (° C.) | Rf (solvent)/MS (M + 1) |
|---|---|---|---|---|---|
| 127 | " | " | benzyloxymethyl | 151–152 | 433 |
| 128 | 1,2-dimethylindol-3-yl | " | " | 137–138 | 447 |
| 129 | 4-(2-tert-butoxy)methylphenyl (4-methylphenyl-OC(CH3)3) | " | " | | 0.65 (toluene/acetone 7/3) 466 |
| 130 | 4-biphenylyl | " | " | 163–165 | 470 |
| 131 | 1,2-dimethylindol-3-yl | " | 4-methoxybenzyl | 214–215 | 447 |
| 132 | 4-chloro-2-(tert-butoxy)phenyl | " | " | | 0.66 (CH2Cl2/CH3OH 10/0.5) 487 |
| 133 | 4-methylphenyl-OC(CH3)3 | " | " | 176–178 | 466 |
| 134 | 4-(4-fluorophenyl)piperazin-1-ylmethyl (with N-ethyl) | " | " | 106–110 | 522 |
| 135 | (naphthalen-1-ylamino)methyl | " | " | | 0.46 (CH2Cl2/CH3OH 10/0.5) 477 |

TABLE 7-continued
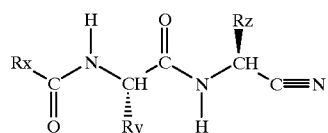
XVII
| Example No. | Rx | Ry | Rz | mp. (° C.) | Rf (solvent)/MS (M + 1) |
|---|---|---|---|---|---|
| 136 | 4-F-C6H4-piperazine-N-CH2- | " | " |  | 0.51 (CH2Cl2/CH3OH 10/0.5) 510 |
| 137 | Ph-piperidine-N-CH2- | " | " |  | 0.26 (CH2Cl2/CH3OH 10/0.5) 491 |
| 138 | 4-MeO-C6H4-piperazine-N-CH2- | " | 4-CF3-C6H4-CH2- | 121–126 | 560 |
| 139 | 4-F-C6H4-piperazine-N-CH2- | " | " | 141–143 | 548 |
| 140 | Ph-piperidine-N-CH2- | " | " | 233–234 | 529 |
| 141 | 2-methylindole | " | " | 199–202 | 471 |
| 142 | 3-MeO-C6H4-piperazine-N-CH2- | " | 4-MeO-C6H4-CH2- | 122–126 | 522 |
| 143 | 3-Me-C6H4-piperazine-N-CH2- | " | " |  | 0.40 (CH2Cl2/CH3OH 10/0.5) 506 |
| 144 | tetrahydronaphthyl-NH-CH2- | " | 4-CF3-C6H4-CH2- | 131–133 | 515 |

TABLE 7-continued
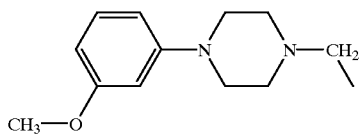
XVII
| Example No. | Rx | Ry | Rz | mp. (° C.) | Rf (solvent)/MS (M + 1) |
|---|---|---|---|---|---|
| 145 | 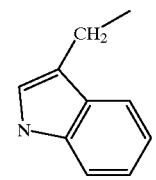 | " | " | 114–115 | 560 |
| 146 | 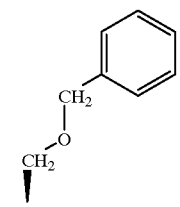 | " | " | 180–182 | 485 |
| 147 | " | " | 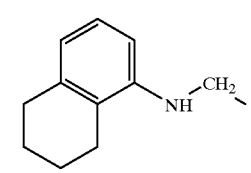 | 129–133 | 447 |
| 148 | 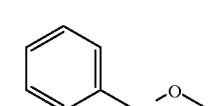 | " | " | | 0.50 (toluene/EtOH 9/1) 477 |
| 149 | 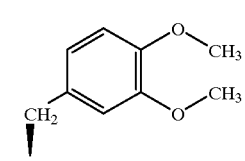 | " | 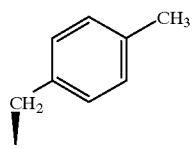 | 145–146 | 454 |
| 150 | " | " | 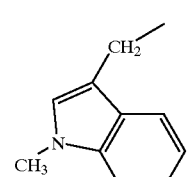 | 152–153 | 408 |
| 151 | 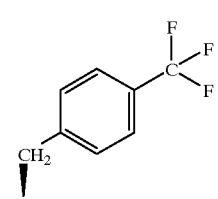 | " |  | 210–211 | 499 |

TABLE 7-continued

XVII

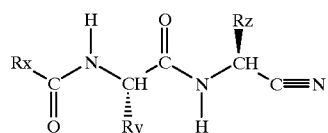

| Example No. | Rx | Ry | Rz | mp. (° C.) | Rf (solvent)/MS (M + 1) |
|---|---|---|---|---|---|
| 152 | (4-methoxyphenyl-piperazinyl-CH2CH2-) | " | (4-methylbenzyl-) | 148–149 | 506 |
| 153 | (2-methylindol-) | " | " | 236–237 | 417 |

Compounds of Examples 1 to 153 are typically selective inhibitors of cathepsin K and generally have $IC_{50}$s for inhibition of human cathepsin K of from about 100 to about 1 nM or less, e.g. about 0.5 nM.

Representative compounds e.g. as described in the the above Examples typically have $IC_{50}$s for inhibition of Cathepsin K in the range from less than 1 up to about 100 run, and $IC_{50}$s for inhibition of Cathepsin K which are at least 10 to about 1000 times less than their $IC_{50}$s for inhibition of Cathepsin L and Cathepsin S, e.g. when tested in the assays described above.

The cathepsin K selective compounds of the invention are particularly indicated for preventing or treating osteoporosis of various genesis (e.g. juvenile, menopausal, post-menopausal, post-traumatic, caused by old age or by corticosteroid therapy or inactivity).

By repeating the procedures described in the above Examples using appropriate starting materials and reaction conditions the following compounds of formula XVII are obtained as identified below in Tables 8, 9 and 10

TABLE 8

XVII

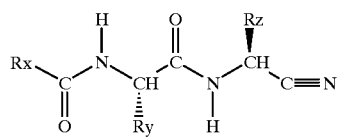

| Example | $R_x$ | $R_y$ | $R_z$ | mp. (° C.) | MS (M + 1) Rf (solvent) |
|---|---|---|---|---|---|
| 154 | (diphenylmethyl-) | (benzyl-) | H | 169–170 | 574 (M − 1) |

TABLE 8-continued
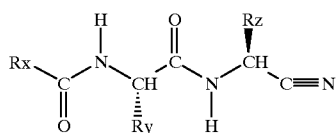
XVII
| Example | Rx | Ry | Rz | mp. (° C.) | MS (M + 1) Rf (solvent) |
|---|---|---|---|---|---|
| 155 | diphenylmethyl | CH₂CH(CH₃)₂ | H | | 0.80(n-hexane/EtOAC = 1/1) |
| 156 | N-methylmorpholine | CH₂CH(CH₃)₂ | H | | 0.63(n-hexane/EtOAC = 1/2) |
| 157 | 1,2-diphenylethyl | CH₂CH(CH₃)₂ | H | | 0.53(n-hexane/EtOAC = 1/1) |
| 158 | phenyl | CH₂CH(CH₃)₂ | H | | 0.38(n-hexane/EtOAC = 1/1) |
| 159 | 2-(1-benzyl)pyridyl | CH₂-phenyl | H | | 422.2 |
| 160 | 3-fluorophenyl | CH₂-indol-3-yl | H | | 365.1 |
| 161 | 2-thienyl | CH₂-indolin-3-yl | H | | 353 |

TABLE 8-continued

XVII

| Example | Rx | Ry | Rz | mp. (° C.) | MS (M + 1) Rf (solvent) |
|---|---|---|---|---|---|
| 162 | 4-pyridyl | CH2-cyclohexyl | H | | 315.1 |
| 163 | 3-pyridyl | CH2-cyclohexyl | H | | 314.9 |
| 164 | 2-furyl | CH2-cyclohexyl | H | | 304.1 |
| 165 | 2-thienyl | C(CH3)3 | H | | 259.1 |
| 166 | phenyl | C(CH3)3 | H | | 288.1 |
| 167 | 3-chlorophenyl | C(CH3)3 | H | | 322 |
| 168 | 3-methoxyphenyl | C(CH3)3 | H | | 318.1 |
| 169 | 3-(indol-3-yl)vinyl | 2-methyl-5-ethyl-furyl-CH2 | H | | 378.5 |

TABLE 8-continued
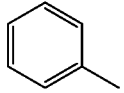
XVII
| Example | Rx | Ry | Rz | mp. (° C.) | MS (M + 1) Rf (solvent) |
|---|---|---|---|---|---|
| 170 | 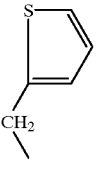 | 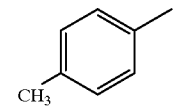 | H | | 313.9 |
| 171 | 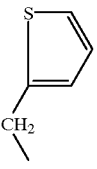 | 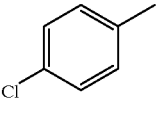 | H | | 327.9 |
| 172 | 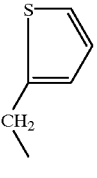 | 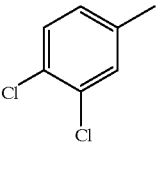 | H | | 349.9 |
| 173 | 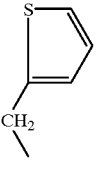 | 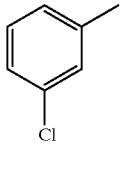 | H | | 383.7 |
| 174 | 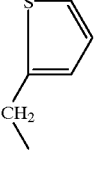 | 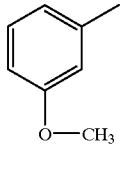 | H | | 349.8 |
| 175 | 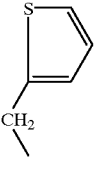 | 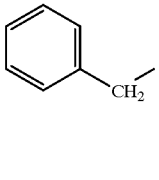 | H | | 343.9 |
| 176 | 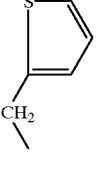 | 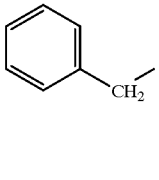 | H | | 327.9 |

TABLE 8-continued

XVII

Structure: Rx-C(=O)-NH-CH(Ry)-C(=O)-NH-CH(Rz)-C≡N

| Example | Rx | Ry | Rz | mp. (° C.) | MS (M + 1) Rf (solvent) |
|---|---|---|---|---|---|
| 177 | PhCH₂CH₂– | 2-thienyl-CH₂– | H | | 341.9 |
| 178 | 4-pyridyl-CH₂– | 4-pyridyl-CH₂– | H | | 315.2 |
| 179 | 2-thienyl– | 2-thienyl-CH₂– | H | | 319.9 |
| 180 | 3-fluorophenyl– | 2-thienyl-CH₂– | H | | 332 |
| 181 | 4-chlorophenyl– | cyclohexyl-CH₂– | H | | 348.1 |
| 182 | 3,4-dichlorophenyl– | cyclohexyl-CH₂– | H | | 381.3 |
| 183 | 4-methoxyphenyl– | cyclohexyl-CH₂– | H | | 344.0 |
| 184 | 3-chlorophenyl– | cyclohexyl-CH₂– | H | | 347.9 |

TABLE 8-continued
XVII
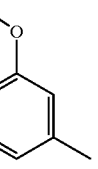
| Example | R$_x$ | R$_y$ | R$_z$ | mp. (° C.) | MS (M + 1) Rf (solvent) |
|---|---|---|---|---|---|
| 185 | 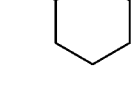 | 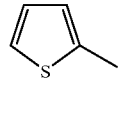 | H | | 344.0 |
| 186 | 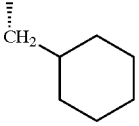 | 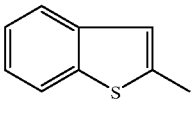 | H | | 320 |
| 187 | 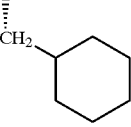 | 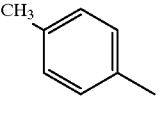 | H | | 370 |
| 188 | 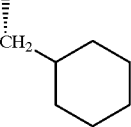 | 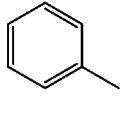 | H | | 328 |
| 189 | 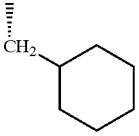 | 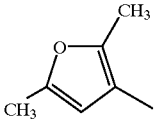 | H | | 313.8 |
| 190 | 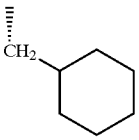 | 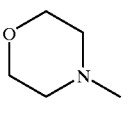 | H | | 332 |
| 191 | 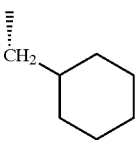 | 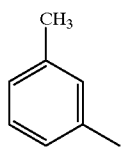 | H | | 322.9 |
| 192 | 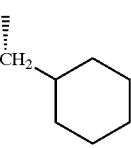 | | H | | 381.8 |

TABLE 8-continued

XVII structure: Rx-C(=O)-NH-CH(Ry)-C(=O)-NH-CH(Rz)-C≡N

| Example | Rx | Ry | Rz | mp. (° C.) | MS (M + 1) Rf (solvent) |
|---|---|---|---|---|---|
| 193 | 3-fluorophenyl | CH2-cyclohexyl | H | | 332 |
| 194 | 3-nitrophenyl | CH2-cyclohexyl | H | | 358.8 |
| 195 | benzo[1,3]dioxol-5-yl methyl | CH2-cyclohexyl | H | | 357.9 |
| 196 | 3-cyanophenyl | CH2-cyclohexyl | H | | 338.8 |
| 197 | CH3-C≡C- | CH2-cyclohexyl | H | | 275.9 |
| 198 | 2-phenylthiazol-4-yl | CH2-cyclohexyl | H | | 397.9 |
| 199 | 6-methyl-1H-indol-yl | CH2-cyclohexyl | H | | 352.9 |
| 200 | 1,5-dimethyl-1H-pyrrol-2-yl | CH2-cyclohexyl | H | | 316.9 |

TABLE 8-continued
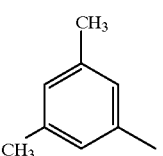
XVII
| Example | Rx | Ry | Rz | mp. (° C.) | MS (M + 1) Rf (solvent) |
|---|---|---|---|---|---|
| 201 | 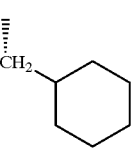 | 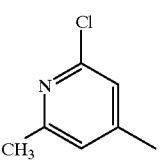 | H | | 392 |
| 202 | 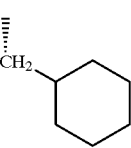 | 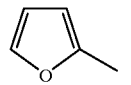 | H | | 360.8 |
| 203 | 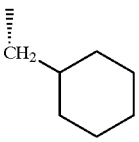 | 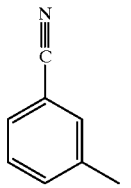 | Δ * | | 330 |
| 204 | 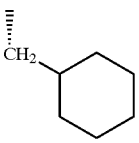 | 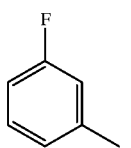 | Δ | | 365 |
| 205 | 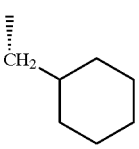 | 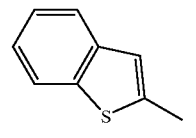 | Δ | | 358 |
| 206 | 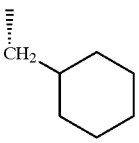 | 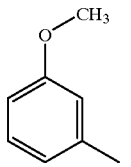 | Δ | | 396 |
| 207 | 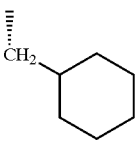 | | Δ | | 370 |

TABLE 8-continued
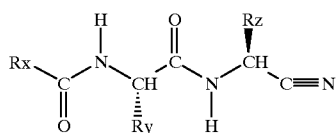
XVII
| Example | Rx | Ry | Rz | mp. (° C.) | MS (M + 1) Rf (solvent) |
|---|---|---|---|---|---|
| 208 | 3-chlorophenyl | CH2-cyclohexyl | Δ | | 374 |
| 209 | 4-methoxyphenyl | CH2-cyclohexyl | Δ | | 370 |
| 210 | 4-methylphenyl | CH2-cyclohexyl | Δ | | 354 |
| 211 | 4-morpholinyl | CH2-cyclohexyl | Δ | | 345.1 |
| 212 | 3-cyanophenyl | CH2CH(CH3)2 | Δ | | 325 |
| 213 | 3-fluorophenyl | CH2CH(CH3)2 | Δ | | 318 |
| 214 | 3,4-dichlorophenyl | CH2CH(CH3)2 | Δ | | 368 |
| 215 | 3-chlorophenyl | CH2CH(CH3)2 | Δ | | 307.9 |

TABLE 8-continued

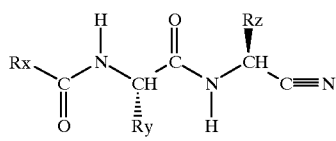

XVII

| Example | $R_x$ | $R_y$ | $R_z$ | mp. (° C.) | MS (M + 1) Rf (solvent) |

* Δ is cyclopropyl, i.e. Rz is ethylene and makes a cyclopropyl ring with the carbon atom to which it is attached.

The compounds of Table 8 are typically selective inhibitors for cathepsin S, and normally have $IC_{50}$s or cathepsin S inhibition in the range from abot 100 to about 10 nM.

TABLE 9

| Example | $R_x$ | $R_y$ | $R_z$ | mp. (° C.) | MS (M + 1) |
|---------|-------|-------|-------|------------|------------|
| 216 | diphenylmethyl | 3-chlorobenzyl | H | 184–185 | 432 |
| 217 | diphenylmethyl | 3-methylbenzyl | H | 181–182 | 412 |
| 218 | diphenylmethyl | 2-naphthylmethyl | H | 188–189 | 448 |
| 219 | 1-phenylpropyl | 3-methylbenzyl | H | 168–169 | 364 |

TABLE 9-continued
| Example | R$_x$ | R$_y$ | R$_z$ | mp. (° C.) | MS (M + 1) |
|---|---|---|---|---|---|
| 220 | 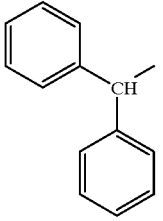 | 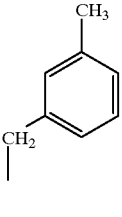 | A | 208–209 | 438 |
| 221 | 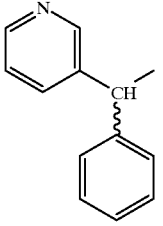 | 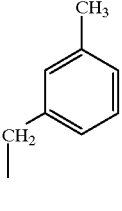 | H | 146–148 | 413 |
| 222 | 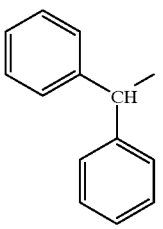 | 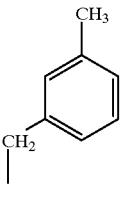 | H | 194–195 | 483 |
| 223 | 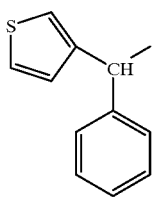 | 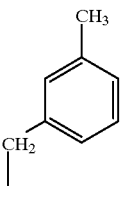 | H | 186–187 | 418 |
| 224 | 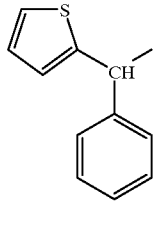 | 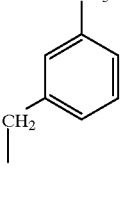 | H | 176–177 | 418 |
| 225 | 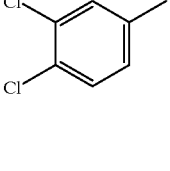 | 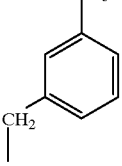 | H | 174–175 | 391 |

TABLE 9-continued
| Example | R$_x$ | R$_y$ | R$_z$ | mp. (° C.) | MS (M + 1) |
|---|---|---|---|---|---|
| 226 | 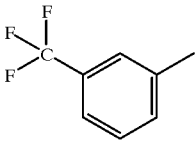 | 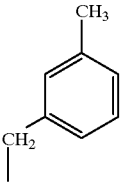 | H | | 390 |
| 227 | 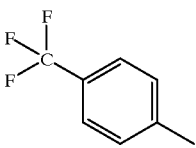 | 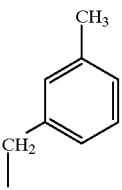 | H | 180–181 | 440 |
| 228 | 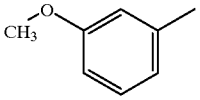 | 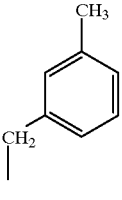 | H | | 352 |
| 229 | 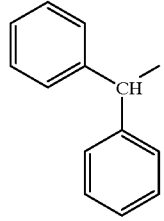 | 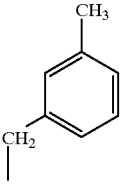 | H | 139–140 | 562 |
| 230 | 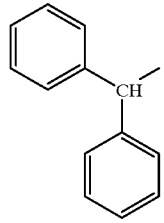 | 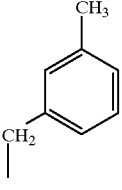 | 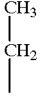 | 180–181 | 440 |
| 231 | 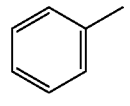 | 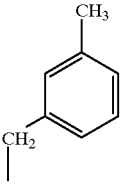 | 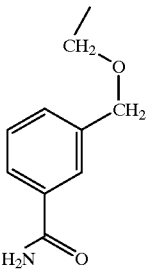 | 151–153 | 485 |

TABLE 9-continued
| Example | R_x | R_y | R_z | mp. (° C.) | MS (M + 1) |
|---|---|---|---|---|---|
| 232 | 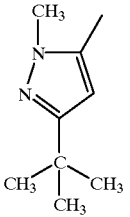 | 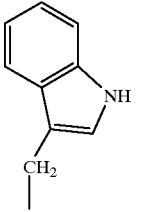 | H | 112–114 | 407 |
| 233 | 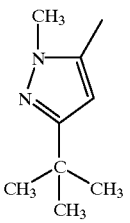 | 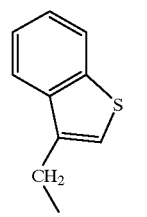 | H | | 424.3 |
| 234 | 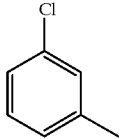 | 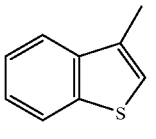 | H | | 399.4 |
| 235 | 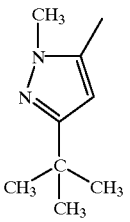 | 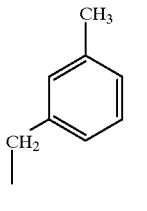 | H | | 382 |
| 236 | 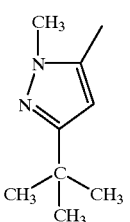 | 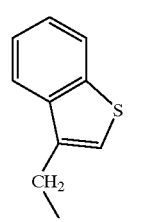 | H | | 468.0 |
| 237 | 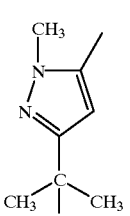 | 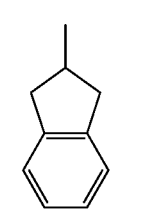 | H | | 394.2 |

TABLE 9-continued
| Example | Rx | Ry | Rz | mp. (° C.) | MS (M + 1) |
|---|---|---|---|---|---|
| 238 | 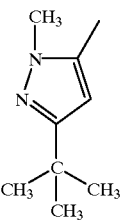 | 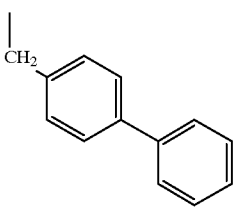 | H | | 444.3 |
| 239 | 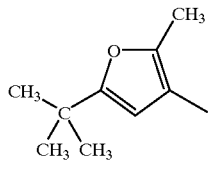 | 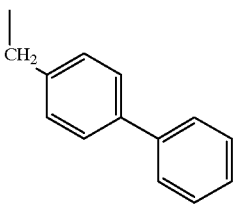 | H | | 444.2 |
| 240 | 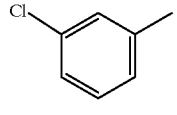 | 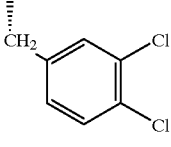 | H | | 411.9 |
| 241 | 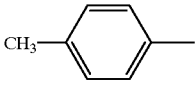 | 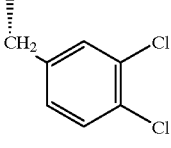 | H | | 390.1 |
| 242 | 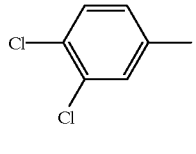 | 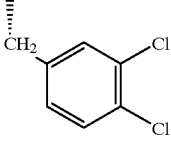 | H | | 445.9 |
| 243 | 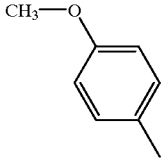 | 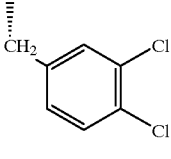 | H | | 406.0 |
| 244 | 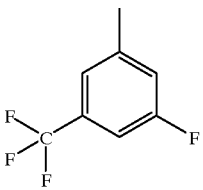 | 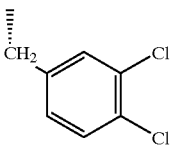 | H | | 461.9 |
| 245 | 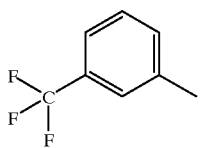 | 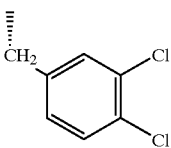 | H | | 443.7 |

TABLE 9-continued
| Example | Rx | Ry | Rz | mp. (° C.) | MS (M + 1) |
|---|---|---|---|---|---|
| 246 | 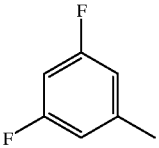 | 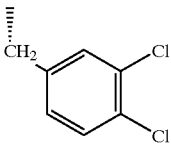 | H | | 411.7 |
| 247 | 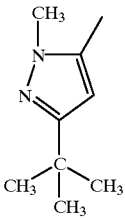 | 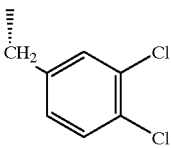 | H | | 435.8 |
| 248 | 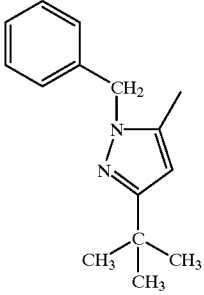 | 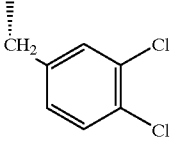 | H | | 511.9 |
| 249 | 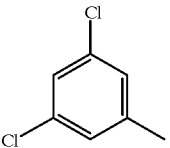 | 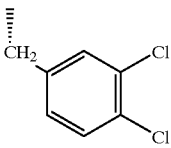 | H | | 445.5 |
| 250 | 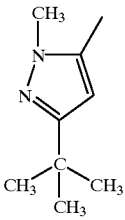 | 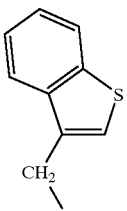 | H | | 429.4 |
| 251 | 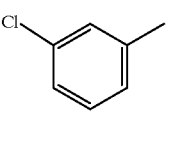 | 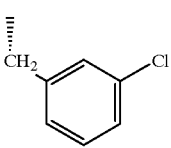 | H | | 376 |
| 252 | 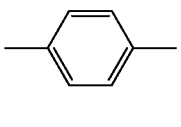 | 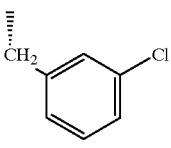 | H | | 356 |

TABLE 9-continued
| Example | R$_x$ | R$_y$ | R$_z$ | mp. (° C.) | MS (M + 1) |
|---|---|---|---|---|---|
| 253 | 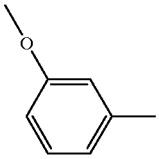 | 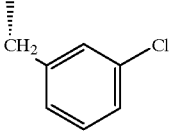 | H | | 372 |
| 254 | 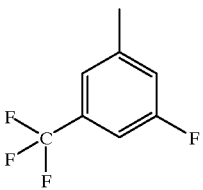 | 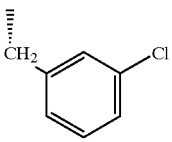 | H | | 427.9 |
| 255 | 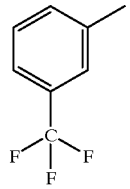 | 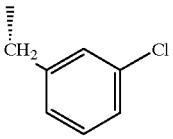 | H | | 410 |
| 256 | 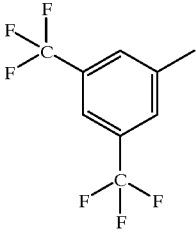 | 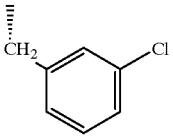 | H | | 477.9 |
| 257 | 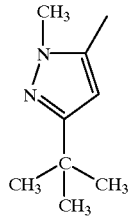 | 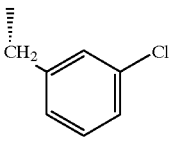 | H | | 402 |
| 258 | 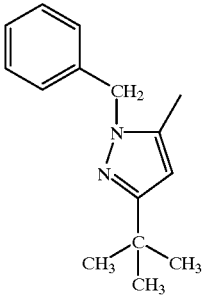 | 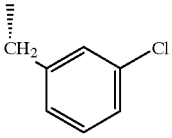 | H | | 478 |
| 259 | 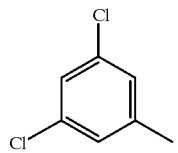 | 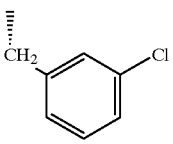 | H | | 409.9 |

TABLE 9-continued
| Example | R$_x$ | R$_y$ | R$_z$ | mp. (° C.) | MS (M + 1) |
|---|---|---|---|---|---|
| 260 | 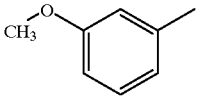 | 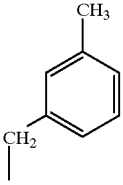 | H | 134–135 | 350 (M − 1) |
| 261 | 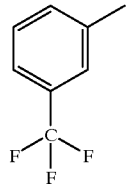 | 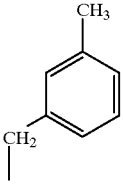 | H | 122–124 | 388 (M − 1) |
| 262 | 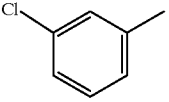 | 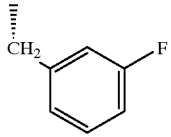 | H | | 360.0 |
| 263 | 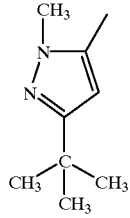 | 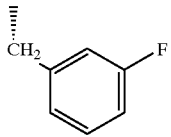 | H | | 385.9 |
| 264 | 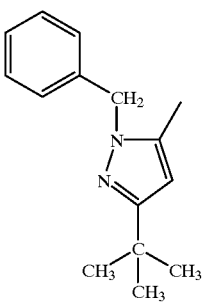 | 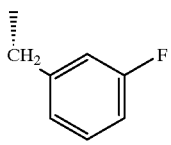 | H | | 461.9 |
| 265 | 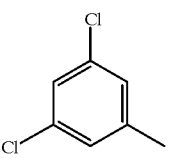 | 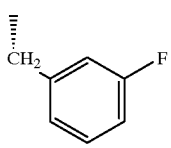 | H | | 393.8 |
| 266 | 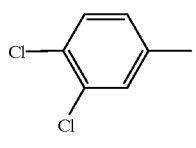 | 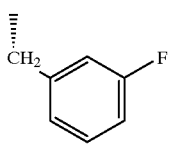 | H | | 411.7 |

TABLE 9-continued

| Example | Rx | Ry | Rz | mp. (° C.) | MS (M + 1) |
|---|---|---|---|---|---|
| 267 | 1-methyl-5-methyl-3-tert-butyl-pyrazole | CH2-(3,4-difluorophenyl) | H | | 408.0 |
| 268 | 1-benzyl-5-methyl-3-tert-butyl-pyrazole | CH2-(3,4-difluorophenyl) | H | | 480.0 |
| 269 | 3,5-dichlorophenyl | CH2-(3,4-difluorophenyl) | H | | 411.8 |
| 270 | 3,4-methylenedioxyphenyl | CH2-(3-chlorophenyl) | H | | 385.9 |
| 271 | 3,4-dimethylphenyl | CH2-(3-chlorophenyl) | H | | 369.9 |
| 272 | 2,3-dimethyl-4-tert-butyl-furan-5-yl | CH2-(3-chlorophenyl) | H | | 402 |
| 273 | 1-methyl-5-methyl-3-tert-butyl-pyrazole | CH2-(3-methylphenyl) | Δ | | 408 |

TABLE 9-continued
| Example | R$_x$ | R$_y$ | R$_z$ | mp. (° C.) | MS (M + 1) |
|---|---|---|---|---|---|
| 274 | 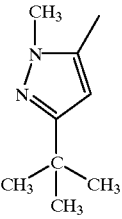 | 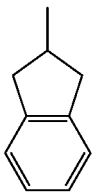 | H | | 394 |
| 275 | 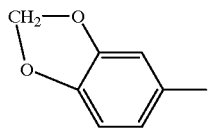 | 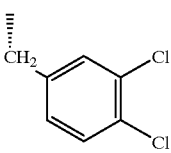 | H | | 421 |
| 276 | 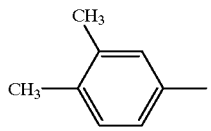 | 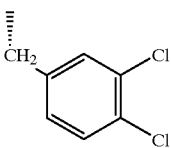 | H | | 409 |
| 277 | 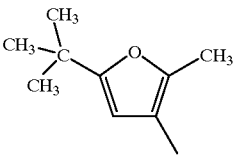 | 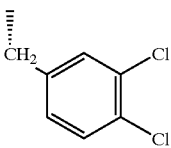 | H | | 437 |
| 278 | 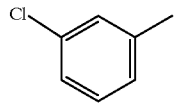 | 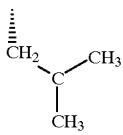 | H | | 307.9 |
| 279 | 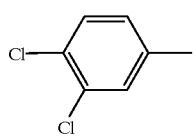 | 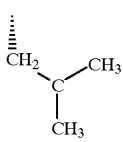 | H | | 341.7 |
| 280 | 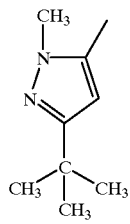 | 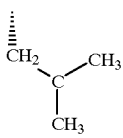 | H | | 333.9 |
| 281 | 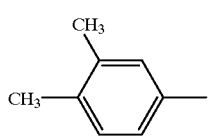 | 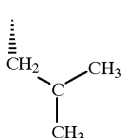 | H | | 302.1 |

TABLE 9-continued

| Example | Rx | Ry | Rz | mp. (° C.) | MS (M + 1) |
|---|---|---|---|---|---|
| 282 | 3,5-dimethyl-1-tert-butyl-pyrazole | 3-methylbenzyl | H | 150–151 | 382 |
| 283 | 3-tert-butyl-5-methyl-1H-pyrazole | 1H-indol-3-ylmethyl | H | | 393 |
| 284 | 3-tert-butyl-1,5-dimethyl-pyrazole | 1H-indol-3-ylmethyl | Δ | | 433 |
| 285 | 3-tert-butyl-5-methyl-1-benzyl-pyrazole | 3-methylbenzyl | H | | 458.3 |
| 286 | 3-tert-butyl-1,5-dimethyl-pyrazole | 3-chlorobenzyl | H | | 450.2 |
| 287 | 3-chlorophenyl | 3,4-dichlorobenzyl | —CH3 | | 424.1 |
| 288 | 3,4-dichlorophenyl | 3,4-dichlorobenzyl | —CH3 | | 457.3 |

TABLE 9-continued
| Example | $R_x$ | $R_y$ | $R_z$ | mp. (° C.) | MS (M + 1) |
|---|---|---|---|---|---|
| 289 | 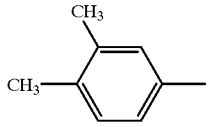 | 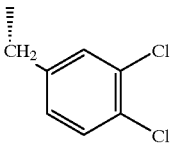 | —CH$_3$ | | 417.9 |
| 290 | 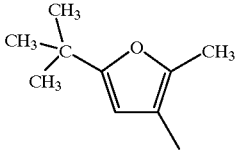 | 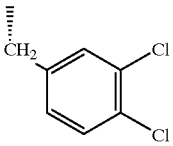 | —CH$_3$ | | 449.8 |
| 291 | 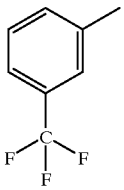 | 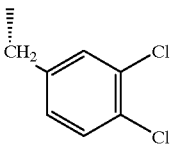 | —CH$_3$ | | 457.8 |
| 292 | 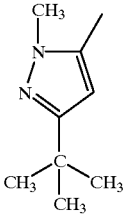 | 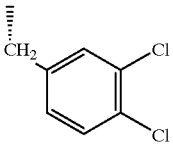 | —CH$_3$ | | 449.9 |
| 293 | 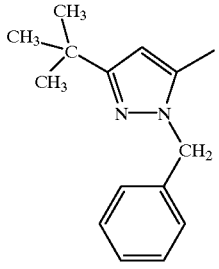 | 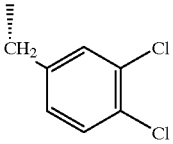 | —CH$_3$ | | 525.9 |
| 294 | 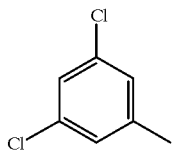 | 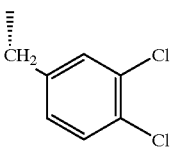 | —CH$_3$ | | 457.7 |
| 295 | 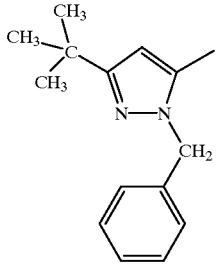 | 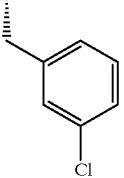 | —CH$_3$ | | 452.1 |

TABLE 9-continued
| Example | R$_x$ | R$_y$ | R$_z$ | mp. (° C.) | MS (M + 1) |
|---|---|---|---|---|---|
| 296 | 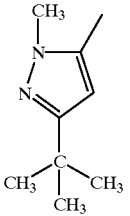 | 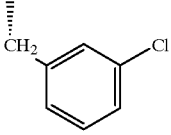 | Δ | | 428.2 |
The compounds of Table 9 are typically selective inhibitors for cathepsin L, having IC$_5$os for cathepin L inhibition which are preferably in the range from about 100 to about 1 nM.
TABLE 10
| Example | R$_x$ | R$_y$ | R$_z$ | mp. (° C.) | MS (M + 1) |
|---|---|---|---|---|---|
| 297 | 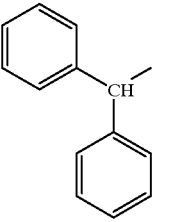 | 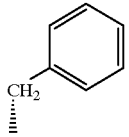 | H | 181–183 | 398 |
| 298 | 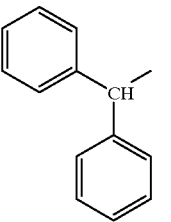 | 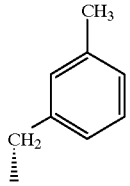 | H | 169–170 | 912 |
| 299 | 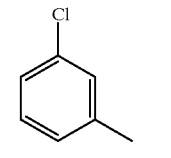 | 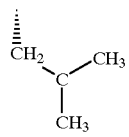 | Δ | | 333.9 |
| 300 | 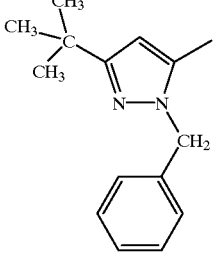 | 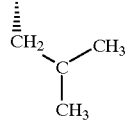 | H | | 410.1 |
| 301 | 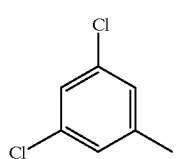 | 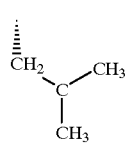 | H | | 434.7 |

The compounds of Table 10 are inhibitors of cathepsin L and cathepsin S, having IC$_{50}$s for inhibition of cathepsin L in the range from about 100 to about 50 nM and IC$_{50}$s for inhibition of cathepsin S in the range from about 50 to about 10 nM.

Example 302

Synthesis of N-[2-[(3-(methoxy-carbonyl)-phenyl)-methoxy]-1(S)-cyanoethyl]-3-methyl-Nα-(2,2-diphenylacetyl)-L-phenyl-alaninamide A. O-[[3-(methoxycarbonyl)-phenyl]methyl]-N-(t-butoxycarbonyl)-L-serine To a solution of Nt-butoxycarbonyl)-L-serine (16.1 g, 78.46 mmol) in DMF (90 mL) at −15° C. is added sodium hydride (6.9 g, 60% in mineral oil, 172.6 mmol) portionwise with vigorous stirring, over 0.5 hour. After all sodium hydride is added, the mixture is stirred for an additional 10 minutes at 0° C., and then at room temperature for 30 minutes. The solution is cooled back to 0° C., and a solution of methyl 3-bromomethylbenzoate (19.77 g, 86.30 mmol) in DMF (90 mL) is added dropwise over 15 minutes. The mixture is then warmed to room temperature for 16 hours. DMF is then evaporated (high vacuum, <40° C.), and the residue is diluted with cold water (200 mL) and acidified to pH 4–5 with 1 N HCl. The resulting mixture is extracted with EtOAc (4×150 mL). The combined extracts are washed with 0.1 N HCl (2×300 mL) and brine (2×300 mL), dried over MgSO$_4$, and evaporated to give a yellowish syrup. Chromatography (silica, 5% MeOH/CH$_2$Cl$_2$) yields O-[[3-(methoxycarbonyl)-phenyl]methyl]-N-(t-butoxycarbonyl)-L-serine as a yellowish oil.

B. O-[[3-(methoxycarbonyl)phenyl]methyl]-N-(t-butoxycarbonyl)-L-serinamide

A solution of O-[[3-(methoxycarbonyl)phenyl]methyl]-N-(t-butoxycarbonyl)-L-serine (3.0 g, 8.50 mmol) and N-methylmorpholine (2.8 mL, 2.58 g, 25.5 mmol) in CH$_2$Cl$_2$ (50 mL) is cooled to −10° C, and isobutyl chloroformate (1.1 mL, 1.16 g, 8.5 mmol) is added dropwise over 10 minutes. After stirring for 15 minutes, ammonia gas is bubbled into the solution at a moderately vigorous rate for 15 minutes. The solution is then warmed to room temperature over 30 minutes. CH$_2$Cl$_2$ is evaporated, and the residue is dissolved in EtOAc (50 mL). This solution is then extracted with 1 N HCl (2×50 mL), saturated NaHCO$_3$ (50 mL), water (50 mL) and brine (50 mL), dried over MgSO$_4$, and evaporated. Chromatography (silica, 75% EtOAc/hexane) yields O-[[3-(methoxycarbonyl)phenyl]methyl]-N-(t-butoxycarbonyl)-L-serinamide as a thick oil.

C. O-[[3-(methoxycarbonyl)phenyl]methyl]-L-serinamide.HCl

To a solution of O-[[3-(methoxycarbonyl)phenyl]methyl]-N-(t-butoxycarbonyl)-L-serinamide (2.4 g, 6.82 mmol) in EtOAc (50 mL) at 0° C. is bubbled HCl gas at a moderately vigorous rate for 5 minutes, during which time a lot of white precipitate is observed. The mixture is warmed to room temperature over 30 minutes, after which time EtOAc is removed, yielding O-[[3-(methoxycarbonyl)phenyl]methyl]-L-serinamide.HCl as a white solid.

D. 3-methyl-N-(2,2-diphenylacetyl)-L-phenylalanine

To a solution of 3-methyl-L-phenylalanine (1.8 g, 10.06 mmol) and Na$_2$CO$_3$ (3.2 g, 3.0.18 mmol) in water (150 mL) is added a solution of diphenylacetyl chloride (2.32 g, 10.06 mmol) in THF (150 mL), and the resulting solution is stirred vigorously at room temperature overnight. The THF is then evaporated and the aqueous layer is diluted with 6% aqueous Na$_2$CO$_3$ (100 mL), and washed with Et$_2$O (3×150 mL). The aqueous layer is then acidified to pH 1 with conc. HCl, and the resulting slurry is extracted with EtOAc (3×100 mL). The organic phase is then washed with water (2×100 mL) and brine (1×100 mL), dried over MgSO$_4$ and evaporated to yield 3-methyl-N-(2,2-diphenylacetyl)-L-phenylalanine, as a white solid.

E. N-[3-methyl-N-(2,2-diphenylacetyl)-L-phenylalanyl]-O-[[3-(methoxycarbonyl)phenyl]methyl]-L-serinamide To a solution of 3-methyl-N-(2,2-diphenylacetyl)-L-phenylalanine (1.0 g, 2.68 mmol) and O-[[3-(methoxycarbonyl)phenyl]methyl]-L-serinamide HCl (0.774 g, 2.68 mmol), 1-hydroxybenzotriazole hydrate (0.452 g, 2.95 mmol, and N-methylmorpholine (1.18 mL, 1.085 g, 10.72 mmol) in CH$_2$Cl$_2$ (50 mL) is added 1-(3-dimethylaminopropyl)-3-ethylcarbodiimide HCl (0.771 g, 4.02 mmol) in one portion and the mixture is stirred at room temperature for 16 hours. The solution is then washed with 1 N HCl (100 mL), saturated aqueous NaHCO$_3$ (1×50 mL), water (1×50 mL) and brine (1×50 mL), dried over MgSO$_4$, and evaporated. The residual solid is triturated with hot methanol to yield N-[3-methyl-N-(2,2-diphenylacetyl)-L-phenylalanyl]-O-[[3-(methoxycarbonyl)phenyl]methyl]-L-serinamide as a white solid.

F. N-[2-[(3-(methoxy-carbonyl)-phenyl)-methoxy]-1(S)-cyanoethyl]-3-methyl-Nα-(2,2-diphenylacetyl)-L-phenyl-alaninamide Oxalyl chloride (0.057 mL, 0.084 g, 0.66 mmol) is added dropwise to DMF (10 mL), and the resulting solution is cooled to 0° C. After the solution becomes clear, pyridine (0.11 mL, 0.10 g, 1.31 mmol) is added, followed by N-[3-methyl-N-(2,2-diphenylacetyl)-L-phenylalanyl]-O-[[3-(methoxy-carbonyl)-phenyl]methyl]-L-serinamide (0.20 g, 0.329 mmol), in one portion. The yellow reaction solution is stirred at 0° C. for 1.5 hours, after which time the it is diluted with EtOAc (50 mL), and washed with saturated NaHCO$_3$ (1×50 mL), saturated LiCl (1×50 mL), dried over MgSO$_4$, and evaporated. The residue is chromatographed (silica, 80% EtOAc/hexane) to yield N-[2-[(3-(methoxy-carbonyl)-phenyl)-methoxy]-1(S)-cyanoethyl]-3-methyl-Nα-(2,2-diphenylacetyl)-L-phenyl-alaninamide as a white solid having the following structure

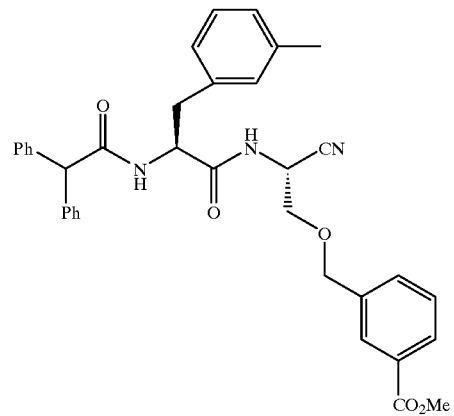

Example 303

Synthesis of N-[2-[(3-carboxypheny)methoxy]-1(S)-cyanoethyl]-3-methyl-Nα-(diphenyacetyl)-L-phenylalaninamide A solution of N-[2-[(3-(methoxycarbonyl)phenyl)methoxy]-1(S)-cyanoethyl]-3-methyl-Nα-(2,2-diphenylacetyl)-L-phenylalaninamide (0.34 g, 0.58 mmol) in pinacolone (20 mL) is degassed with bubbling nitrogen for 10 minutes. Lithium iodide (0.78 g, 5.80 mmol) is then added, and the solution is refluxed in the dark for 24 hours, after which time it is cooled to room temperature, diluted with ethyl acetate (50 mL), and washed with 5% aq. sodium thiosulfate (2×50 mL), water (1×50 mL) and brine (1×50 mL). The organic layer is then dried over MgSO$_4$, evaporated, and the residue is chromatographed (silica, 3% MeOH/CH$_2$Cl$_2$/0.05% acetic acid) to yield a clear glass, which is crystallized with an EtOAc/hexane (1:50) mixture to yield N-[2-[(3-carboxyphenyl)methoxy]-1(S)-cyanoethyl]-3-methyl-Nα-(diphenyacetyl)-L-phenylalaninamide as a white solid, m.p. 160–162° C.

Example 304
N-[2-[(3-(allyloxycarbonyl)-phenybmethogyl-1(S)-cyanoethyl]-3-methyl-Nα-(N-morpholinocarbonyl)-L-phenylalaninamide A. 3-methyl-N-(t-butoxycarbonyl)-L-phenylalanine To a suspension of 3-methyl-L-phenylalanine (2.7 g, 15 mmol) in 85 mL 10% triehylamine/methanol is added di-t-butyldicarbonate (6.5 g, 30 mmol), and the solution is refluxed for 2.5 hours. After cooling, the methanol and triethylamine are evaporated and the residue is diluted with Et$_2$O (250 mL) and extracted with saturated Na$_2$CO$_3$ (2×75 mL). The combined aqueous layers are again washed with Et$_2$O (250 mL), and then acidified with conc. HCl to pH 2–3. The resulting mixture is then extracted with EtOAc (3×75 mL) and washed with water and brine, dried over MgSO$_4$, and evaporated to yield 3-methyl-N-(t-butoxycarbonyl)-L-phenylalanine as a clear oil.

B. allyl 3-(chloromethyl)-benzoate

A solution of 3-(chloromethyl)-benzoic acid (50.0 g, 0.293 mol), potassium carbonate (48.61 g, 0.352 mol) and allyl bromide (50.7 mL, 0.586 mol) in acetone (500 mL) is refluxed for 2 hours, after which time the solution was cooled to room temp. and filtered through celite. The filtrate is evaporated and the residue chromatographed (silica, 5% EtOAc/hexane) to yield allyl 3-(chloromethyl)-benzoate as a clear oil.

C. allyl 3-(iodomethyl)-benzoate

A solution of allyl 3-(chloromethyl)-benzoate (54.5 g, 0.259 mmol) and sodium iodide (46.56 g, 0.311 mol) in acetone (500 mL) is stirred at room temp. for 6.5 hours, after which time the mixture is filtered. The filitrate is evaporated and the residue is dissolved in diethyl ether (500 mL), then washed with water (1×200 mL), 5% sodium sulfite solution (1×200 mL) and brine (1×200 mL), dried over magnesium sulfate, and evaporated to yield allyl 3-(iodomethyl)-benzoate as a white solid, which was is directly.

D. O-[[3-(allyloxycarbonyl)-phenyl]methyl]-N-(t-butoxycarbonyl)-L-serine

Sodium hydride (19.4 g, 60% in mineral oil, 484.4 mmol) is washed with dry hexanes (2×30 mL) to remove the mineral oil and then suspended in anhydrous DMF (330 mL). To this suspension a solution of N-butoxycarbonyl-L-serine (45.2 g, 220.2 mmol) in DMF (110 mL) at 0° C. is added dropwise with vigorous stirring. The mixture is stirred for an additional 5 minutes at 0° C., and then at room temperature for 30 minutes. The solution is cooled back to 0° C., and a solution of allyl 3-iodomethylbenzoate (66.6 g, 220.2 mmol) in DMF (110 mL) is added dropwise over 15 minutes. The mixture is then warmed to room temperature for 30 minutes. The reaction mixture is poured into ice water (2.2 L) and acidified to pH 2 with 1 N HCl (270 mL). The mixture is extracted with ether (1×600 mL, then 3×300 mL) and the combined ether extracts are then washed with water (5×200 ml) and then dried (MgSO$_4$) and evaporated in vacuo to yield O-[[3-(allyloxycarbonyl)-phenyl]methyl]-N-(t-butoxycarbonyl)-L-serine as a yellowish oil, which is used as is in the subsequent step.

E. O-[[3-(allyloxycarbonyl)phenyl]methyl]-N-(t-butoxycarbonyl)-L-serinamide

A solution of O-[[3-(allyloxycarbonyl)phenyl]methyl]-N-(t-butoxycarbonyl)-L-serine (79.2 g, 209 mmol) and N-methylmorpholine (68.9 mL, 63.4 g, 627 mmol) in CH$_2$Cl$_2$ (800 mL) is cooled to –10° C., and isobutyl chloroformate (32.5 mL, 34.2 g, 251 mmol) is added dropwise over 10 minutes. After stirring for 15 minutes, ammonia gas is bubbled into the solution at a moderately vigorous rate for 15 minutes, at –10° C. The solution is then warmed to room temperature and stirred for 30 minutes. The reaction mixure is cooled to 0° C. and 1 N HCl (800 mL) is added. The organic phase is washed with 1 N HCl (2×700 mL), then washed with saturated NaHCO$_3$ (700 mL), then dried (MgSO$_4$) and evaporated in vacuo to yield O-[[3-(allyloxycarbonyl)phenyl]methyl]-N-(t-butoxycarbonyl)-L-serinamide as a thick oil, which is used as is in the subsequent step.

F. O-[[3-(allyloxycarbonyl)phenyl]-methyl]-L-serinamide.HCl

To a solution of O-[[3-(allyloxycarbonyl)phenyl]methyl]-N-(t-butoxycarbonyl)-L-serinamide (69 g, 182.5 mmol) in EtOAc (1000 mL) at 0° C. is slowly bubbled HCl gas for 1 hour, during which time a white precipitate is observed. The mixture is warmed to room temperature over 30 minutes, after which time EtOAc is removed by evaporation. The resulting residue is triturated with ether (500 mL) with vigorous stirring for 30 minutes. The precipitate is collected by vacuum filtration, washed with ether (2×100 mL) and then air dried to yield O-[[3-(allyloxycarbonyl)phenyl]-methyl]-L-serinamide.HCl as a free-flowing white solid.

G. N-[3-methyl-N-(t-butoxycarbonyl)-L-phenylalanyl]-O-[[3-(allyloxycarbonyl)-phenyl]methyl]-L-serinamide To a solution of O-[[3allyloxycarbonyl)phenyl]methyl]-L-serinamide.HCl (2.92 g, 10.46 mmol), 3-methyl-N-(t-butoxycarbonyl)-L-phenylalanine (3.29 g, 10.46 mmol), 1-hydroxybenzotriazole (1.92 g, 12.55 mmol), and N-methylmorpholine (4.6 mL, 4.23 g, 41.84 mmol) in CH$_2$Cl$_2$ (120 mL) is added 1-(3-dimethylaminopropyl)-3-ethylcarbodiimide.HCl (3.01 g, 15.69 mmol) in one portion. The solution is stirred for 16 hours, then washed with 1 N HCl (100 mL), saturated aqueous NaHCO$_3$ (1×50 mL), water (1×50 mL) and brine (1×50 mL), dried over MgSO$_4$, and evaporated. The residual solid is triturated with hot methanol to yield N-[3-methyl-N-(t-butoxycarbonyl)-L-phenylalanyl]-O-[[3-(allyloxycarbonyl)-phenyl]methyl]-L-serinamide as a white solid.

H. N-[2-[(3-(allyloxycarbonyl)-phenyl)methoxy]-1(S)-cyanoethyl]-3-methyl-Nα-(t-butoxycarbonyl)-L-phenylalaninamide Oxalyl chloride (1.79 mL, 2.6 g, 20.48 mmol) is added dropwise to DMF (30 mL), and the resulting solution is cooled to 0° C. After the solution becomes clear, pyridine (3.31 mL, 3.24 g, 40.96 mmol) is added, followed by N-[3-methyl-N-(t-butoxycarbonyl)-L-phenylalanyl]-O-[[3-(allyloxy-carbonyl)phenyl]methyl]-L-serinamide (5.52 g, 10.24 mmol), in one portion. The yellow reaction solution is stirred at 0° C. for 1.5 hours, after which time it is diluted with EtOAc (50 mL), and washed with saturated NaHCO$_3$ (1×50 mL), saturated LiCl (1×50 mL), dried over MgSO$_4$, and evaporated. The residue is chromatographed (silica, 40% EtOAc/hexane) to yield N-[2-((3-(allyloxycarbonyl)-phenyl)methoxy]-1(S)-cyanoethyl]-3-methyl-Nα-(t-butoxycarbonyl)-L-phenylalaninamide as a white solid.

I. N-[2-[(3-(allyloxycarbonyl)-phenyl)methoxy]-1(S)-cyanoethyl]-3-methyl-L-phenylalaninamide A solution of N-[2-[(3-(allyloxycarbonyl)-phenyl)methoxy]-1(S)-cyanoethyl]-3-methyl-Nα-(t- butoxycarbonyl)-L-phenylalaninamide (3.18 g, 6.10 mmol) in 96% formic acid (40 mL) is stirred at room temperature for 5.5 hours. Formic acid is evaporated (high vacuum, 25° C.), and the residue is taken up in water (50 mL) and basified with saturated NaHCO$_3$ (100 mL). The resulting mixture is extracted with EtOAc (3×50 mL), and then washed with water (2×100 mL) and brine (1×100 mL), dried over MgSO$_4$, and evaporated to yield N-[2-[(3-(allyloxycarbonyl)-phenyl)methoxy]-1(S)-cyanoethyl]-3-methyl-L-phenylalaninamide as a clear thick oil.

J. N-[2-[(3-(allyloxycarbonyl)-phenyl)methoxy]-1(S)-cyanoethyl]-3-methyl-Nα-(N-morpholinocarbonyl)-L-phenylalaninamide To a solution of N-[2-[(3-(allyloxycarbonyl)phenyl)methoxy]-1(S)cyanoethyl]-3-methyl-L-phenylalaninamide.HCl (0.29 g, 0.69 mmol) and N-methylmorpholine (0.23 mL, 0.21 g, 2.07 mmol) in CH$_2$Cl$_2$ (10 mL) is added mopholinecarbonyl chloride (0.21 g, 0.23 mL, 2.065 mmol) in one portion, and the solution is stirred at room temperature for 16 hours. The solution is then diluted with additional CH$_2$Cl$_2$ (40 mL), and washed with 1 N HCl (50 mL), saturated aqueous NaHCO$_3$ (1×50 mL), water (1×50 mL) and brine (1×50 mL), dried over MgSO$_4$, and evaporated. The residue is chromatographed (silica, 80% EtOAc/hexane) to yield N-[2-[(3-(allyloxycarbonyl)-phenyl)methoxy]-1(S)-cyanoethyl]-3-methyl-Nα-(N-morpholinocarbonyl)-L-phenylalaninamide as a clear oil.

The corresponding 3-carboxyphenylmethoxy compound is prepared as follows:

To a solution of N-[2-[(3-(allyloxycarbonyl)-phenyl)methoxy]-1(S)-cyanoethyl]-3-methyl-Nα-(N-morpholinocarbonyl)-L-phenylalaninamide (see example 3, 0.2 g, 0.375 mmol) in anhydrous THF (20 mL) is added morpholine (0.327 mL, 0.326 g, 3.75 mmol), followed by Pd(PPh$_3$)$_4$ (0.043 g, 0.0375 mmol). The solution is stirred at room temperature for 3 hours, after which time the THF is evaporated. The residue is taken up in EtOAc (100 mL) and washed with 1 N HCl (100 mL), saturated aqueous NaHCO$_3$ (1×50 mL), water (1×50 mL) and brine (1×50 mL), dried over MgSO$_4$, and evaporated. The residue is chromatographed (silica, 3% MeOH/CH$_2$Cl$_2$/0.05% acetic acid) to yield a clear glass, which is crystallized with an EtOAc/hexane (1:50) mixture to yield N-[2-[(3-carboxyphenyl)-methoxy]-1(S)-cyanoethyl]-3-methyl-Nα-(N-morpholinocarbonyl)-L-phenylalaninamide as a white solid, m.p. 100° C. (dec.).

Example 305

Synthesis of N-[3-(3-(methoxycarbonyl)-phenoxy)-1-cyanopropyl]-3-methyl-Nα-(2,2-diphenylacetyl)-L-phenylalaninamide A. methyl 3-(2-bromoethoxy)-benzoate A solution of methyl 3-hydroxybenzoate (5.0 g, 32.86 mmol), 1,2-dibromoethane (11.3 mL, 131.44 mmol), and potassium carbonate (5.45 g, 39.43 mmol) in DMF (100 mL) is refluxed 16 hours, after which time the solution is cooled, concentrated in vacuo, and chromatographed to yield methyl 3-(2-bromoethoxy)-benzoate, as a yellow oil.

B. methyl 3-(2-iodoethoxy)-benzoate

A solution of methyl 3-(2-bromoethoxy)-benzoate (2.4 g, 9.26 mmol) and sodium iodide (2.78 g, 18.52 mmol) in acetone (50 mL) is refluxed for 2 hours. The resulting mixture is then filtered and concentrated. The residue is diluted with EtOAc (100 mL), washed with 5% Na$_2$SO$_3$ (50 mL), water (2×50 mL) and brine (50 mL), dried over MgSO$_4$ and evaporated to yield methyl 3-(2-iodoethoxy)-benzoate, as a yellow oil, which is used directly.

C. 2-(diphenylmethyleneamino)4-[(3-methoxycarbonyl)-phenoxy]-butyronitrile

To a solution of sodium hexamethyldisilazide (8.82 mL of a 1.0 M solution, 8.82 mmol) in 90 mL THF at −78° C. is added a solution of N-(diphenylmethylene)aminoacetonitrile (1.90 g, 8.65 mmol) in THF (30 mL), via syringe. After stirring 30 minutes at −78° C., a solution of methyl 3-(2-iodoethoxy)-benzoate (2.7 g, 8.82 mmol) in THF (20 mL) is added in to the reaction solution via syringe. The solution is then warmed to room temperature, and allowed to stir for 3 hours. The mixture is then quenched with saturated NH$_4$Cl (50 mL), and the aqueous layer is extracted with EtOAc (3×50 mL). The combined organic layers are washed with water (1×50 mL) and brine (1×50 mL), and chromatographed (silica, 12.5% EtOAc/hexane) to yield 2-(diphenylmethyleneamino)4-[(3-methoxycarbonyl)-phenoxy]-butyronitrile, as a clear oil.

D. 2-amino4-[3-(methoxycarbonyl)-phenoxy]-butyronitrile 2-(Diphenylmethyleneamino)-4-[(3-methoxycarbonyl)-phenoxy]-butyronitrile (3.7 g, 6.78 mmol) is stirred vigorously for 16 hours in a biphasic mixture of 1 N HCl (7.5 mL) and Et$_2$O (90 mL). The ether layer is removed, and the aqueous layer is washed with Et$_2$O (3×50 mL), basified to pH 8 with 1 N NaOH, and extracted with EtOAc (3×50 mL). The combined organic layers are then washed with brine (1×50 mL), dried over MgSO$_4$ and evaporated to yield 2-amino4-[3-(methoxycarbonyl)-phenoxy]-butyronitrile, as a clear oil.

E. N-[3-(3-(methoxycarbonyl)-phenoxy)-1-cyanopropyl]-3-methyl-Nα-(2,2-diphenylacetyl)-L-phenylalaninamide To a solution of 2-amino-4-[3-(methoxycarbonyl)-phenoxy]-butyronitrile (0.5 g, 2.13 mmol), 3-methyl-N-(2,2-diphenylacetyl)-L-phenylalanine (see example 1, 0.80 g, 2.13 mmol) and diisopropylethylamine (1.1 mL, 6.39 mmol) in CH$_2$Cl$_2$ (15 mL) is added benzotriazol-1-yloxy-tris-(pyrrolidino)-phosphonium hexafluorophosphate (PyBop, 1.22 g, 2.34 mmol) in one portion. After stirring 1.5 hour, an additional portion of PyBop (0.61 g, 1.2 mmol) is added, and the solution is stirred overnight. The reaction mixture is washed with 1 N HCl (50 mL), saturated aqueous NaHCO$_3$ (1×50 mL), water (1×50 mL) and brine (1×50 mL), dried over MgSO$_4$, and evaporated. The residue is chromatographed (silica, 50% EtOAc/hexane) to yield N-[3-(3-(methoxycarbonyl)-phenoxy)-1-cyanopropyl]-3-methyl-Nα-(2,2-diphenylacetyl)-L-phenylalaninamide as a white solid, m.p. 152–153° C.

The corresponding carboxyphenoxy compound is prepared as follows:

To a solution of N-[3-(3-(methoxycarbonyl)-phenoxy)-1-cyanopropyl]-3-methyl-Nα-2,2-diphenylacetyl)-L-phenylalaninamide (0.16 g, 0.272 mmol) in THF (3 mL) is added a solution of LiOH-H$_2$O (22 mg, 0.544 mmol) in water (1.5 mL). The reaction is stirred for 1 hour, after which z.4Dw time e THF is evaporated. The residue is acidified with 1 N HCl and extracted with EtOAc (3×30 mL). The aqueous layer is washed with brine (30 mL), dried over MgSO$_4$, evaporated and chromatographed (5% MeOH, 0.05% AcOH, CH$_2$Cl$_2$) to yield N-[3-(3-carboxyphenoxy)-1-cyanopropyl]-3-methyl-Nα-(2,2-diphenylacetyl)-L-phenylalaninamide, as a white solid, m.p. 169–170° C.

Example 306

Synthesis of N-[2-[(5-(methoxycarbonyl)-fur-2-yl)-methoxy]-1(S)-cyanoethyl]-3-methyl-Nα-(2,2-diphenylacetyl)-L-phenylalaninamide A. 5-(bromomethyl)-2-furoate To a solution of 5-methylfufural (5.0 g, 45.5 mmol) in CH$_2$Cl$_2$ (100 mL) is added pulverized N-bromosuccinimide (17.8 g, 100 mmol), and the solution is subjected to sun lamp irradiation. After 15 minutes, the solution begins to reflux vigorously, and then settles down after another 2–3 minutes. After an additional 10 minutes, the dark mixture is cooled to room temperature, and MeOH (30 mL) is added. After 10 minutes, the solution is evaporated, and the residue is diluted with $Et_2O$, and washed with saturated $NaHCO_3$ (50 mL), water (50 mL) and brine (50 mL), dried over $MgSO_4$ and evaporated. The residue is chromatographed (silica, 15% EtOAc/hexane) to yield methyl 5-(bromomethyl)-2-furoate, as a yellowish oil.

B. O-[[(5-methoxycarbonyl)-fur-2-yl]-methyl]-N-(t-butoxycarbonyl)-L-serine

To a solution of N-(t-butoxycarbonyl)-L-serine (2.5 g, 12.3 mmol) in DMF (50 mL) at −15° C. is added sodium hydride (1.22 g, 60% in mineral oil, 30.7 mmol) portionwise with vigorous stirring, over 0.5 hours. After all sodium hydride is added, the mixture is stirred for an additional 10 minutes at 0° C., and then at room temperature for 30 minutes. The solution is cooled back to 0° C., and a solution of methyl 5-(bromomethyl)-2-furoate (2.5 g, 12.3 mmol) in DMF (10 mL) is added dropwise over 2 minutes. The mixture is then warmed to room temperature for 16 hours, and the residue is quenched with 10% $NaH_2PO_4$ (100 mL) and acidified to pH 3 with 1 N HCl. 10% LiCl (30 mL) is added to the solution, and the resulting mixture is extracted with EtOAc (3×50 mL). The combined extracts are washed with brine (50 mL), dried over $MgSO_4$, and evaporated to give a yellowish syrup. This residue is taken up in $Et_2O$ (50 mL), and extracted with saturated $NaHCO_3$(2×50 mL). The aqueous layer is acidified with conc. HCl, and extracted with $Et_2O$ (2×50 mL), dried ($MgSO_4$), and evaporated. Chromatography (silica, 5% $MeOH/CH_2Cl_2$) yields O-[[(5-methoxycarbonyl)-fur-2-yl]-methyl]-N-(t-butoxycarbonyl)-L-serine as a yellowish oil.

C. O-[[(5-methoxycarbonyl)-fur-2-yl]-methyl]-Nα-(t-butoxycarbonyl)-L-serinamide

A solution of O-[[(5-methoxycarbonyl)-fur-2-yl]-methyl]-N-(t-butoxycarbonyl)-L-serine (0.70 g, 2.1 mmol) and N-methylmorpholine (0.46 mL, 4.2 mmol)) in $CH_2Cl_2$ (50 mL) is cooled to −10° C., and isobutyl chloroformate (0.27 mL, 2.1 mmol)) is added dropwise over 10 minutes. After stirring for 15 minutes, ammonia gas is bubbled into the solution at a moderately vigorous rate for 15 minutes. The solution is then warmed to room temp. over 30 minutes. $CH_2Cl_2$ is evaporated, and the residue is dissolved in EtOAc (50 mL). This solution is then extracted with 1 N HCl (2×50 mL), saturated $NaHCO_3$ (50 mL), water (50 mL) and brine (50 mL), dried over $MgSO_4$, and evaporated to yield O-[[(5-methoxycarbonyl)-fur-2-yl]-methyl]-Nα-(t-butoxycarbonyl)-L-serinamide as a brownish solid.

D. O-[[(5-methoxycarbonyl)-fur-2-yl]-methyl]-L-serinamide.HCl

To a solution of O-[[(5-methoxycarbonyl)-fur-2-yl]-methyl]-Nα-(t-butoxycarbonyl)-L-serinamide (0.52 g, 1.58 mmol)) in EtOAc (50 mL) at 0° C. is bubbled HCl gas at a moderately vigorous rate for 1 minute, during which time a lot of white precipitate is observed. The mixture is stirred at 0° C. for 10 minutes, after which time ethyl acetate is removed, yielding O-[[(5-methoxycarbonyl)-fur-2-yl]-methyl]-L-serinamide.HCl as a yellowish solid.

E. N-[3-methyl-N-(2,2-diphenylacetyl)-L-phenylalanyl]-O-[[5-(methoxycarbonyl)-fur-2-yl]-methyl]-L-serinamide To a solution of 3-methyl-Nα-(2,2-diphenylacetyl)-L-phenylalanine (0.40 g, 1.5 mmol), O-[[(5-methoxycarbonyl)-fur-2-yl]methyl]-L-serinamide.HCl (0.54 g, 1.5 mmol), 1-hydroxybenzo triazole hydrate (0.2 g, 1.5 mmol) and N-methylmorpholine (0.66 mL, 6.0 mmol) in $CH_2Cl_2$ (30 mL) is added 1-(3-dimethylaminopropyl)-3-ethylcarbodiimide.HCl (0.43 g, 2.3 mmol) in one portion, and the mixture is stirred at room temp. for 16 hours. The solution is then washed with 1 N HCl (100 mL), saturated aqueous $NaHCO_3$ (1×50 mL), water (1×50 mL) and brine (1×50 mL), dried over $MgSO_4$, and evaporated. The residual solid is triturated from ether to yield N-[3-methyl-Nα-(2,2-diphenylacetyl)-L-phenylalanyl]-O-[[5-(methoxycarbonyl)-fur-2-yl]-methyl]-L-serinamide as a light yellow solid.

F. N-[2-[(5-(methoxycarbonyl)-fur-2-yl)-methoxy]-1(S)-cyanoethyl]-3-methyl-Nα-(2,2-diphenylacetyl)-L-phenylalaninamide Oxalyl chloride (0.046 mL, 0.36 mmol) is added dropwise to DMF (5 mL), and the resulting solution is cooled to 0° C. After the solution is clear, pyridine (0.032 mL, 0.40 mmol) is added, followed by N-[3-methyl-N-(2,2-diphenylacetyl)-L-phenylalanyl]-O-[[5-(methoxycarbonyl)-fur-2-yl]-methyl]-L-serinamide (0.20 g, 0.33 mmol), in one portion. The yellow reaction solution is stirred at 0° C. for 1.5 hours, after which time it is diluted with EtOAc (50 mL), and washed with saturated $NaHCO_3$ (1×50 mL), saturated LiCl (1×50 mL), dried over $MgSO_4$, and evaporated. The residue is chromatographed (silica, 40% EtOAc/hexane) to yield N-[2-[(5-(methoxycarbonyl)-fur-2-yl)-methoxy]-1(S)-cyanoethyl]-3-methyl-Nα-(2,2-diphenylacetyl)-L-phenylalaninamide as a white solid.

Example 307

Synthesis of N-[2-[(3-(methoxycarbonyl)phenyl)thiomethoxy]-1(S)-cyanoethyl]-3-methyl-Nα-(2,2-diphenylacetyl)-L-phenylalaninamide A. N-[3-methyl-N-(2,2-diphenylacetyl)-L-phenylalanyl]-S-trityl-L-cysteinamide To a solution of 3-methyl-N-(2,2-diphenylacetyl-L-phenylalanine (see example 302, 1.0 g, 2.68 mmol), 1-hydroxybenzotriazole hydrate (0.41 g, 2.68 mmol) and N-methylmorpholine (0.74 mL, 6.69 mmol) in $CH_2Cl_2$ (80 mL) is added 1-(3-dimethylaminopropyl)-3-ethylcarbodiimide.HCl (0.77 g, 4.02 mmol) in one portion. After stirring 30 minutes at room temperature, S-trityl-L-cysteinamide (0.97 g, 2.68 mmol) is added to the solution in one portion, and the solution is stirred for 16 hours. The solution is evaporated, and the residue partitioned between water (80 mL) and ethyl acetate (80 mL). The aqueous layer is washed with EtOAc (2×80 mL), and the combined organic layers are then washed with 1 N HCl (100 mL), saturated aqueous $NaHCO_3$ (1×50 mL), water (1×50 mL) and brine (1×50 mL), dried over $MgSO_4$, and evaporated. The residue is triturated with $Et_2O$/hexane (1:1) to yield N-[3-methyl-N-(2,2-diphenylacetyl)-L-phenylalanyl]-S-trityl-L-cysteinamide as a white solid.

B. N-[3-methyl-N-(2,2-diphenylacetyl)-L-phenylalanyl]-L-cysteinamide

To a solution of N-[3-methyl-N-(2,2-diphenylacetyl)-L-phenylalanyl]-S-trityl-L-cysteinamide (0.68 g, 0.95 mmol) in $CH_2Cl_2$ (20 mL) is added triethylsilane (0.30 mL, 1.9 mmol), in one portion, followed by dropwise addition of trifluoroacetic acid (10 mL). The yellow solution is stirred at room temperature for 1 hour, after which time solvent is evaporated, and the residue is suspended in water (30 mL), filtered, and the collected solid is washed with water and ether (100 mL each), and dried in vacuo, to yield of N-[3-methyl-N-(2,2-diphenylacetyl)-L-phenylalanyl]-L-cysteinamide, as a white solid.

C. N-[3-methyl-N-(2,2-diphenylacetyl)-L-phenylalanyl]-S-[[3-(methoxycarbonyl)phenyl]methyl]-L-cysteinamide A solution of N-[3-methyl-N-(2,2-diphenylacetyl)-L-phenylalanyl]-L-cysteinamide (0.72 g, 1.51 mmol), methyl 3-(bromomethyl)-benzoate (0.35 g, 1.51 mmol), and diisopropylethylamine (0.27 mL, 1.53 mmol) is stirred at room temperature overnight. Solvent is evaporated, and the residue is treated with 1 N HCl (50 mL), and filtered to collect a white solid, which is washed with water and Et$_2$O (100 mL each). Drying in vacuo yields N-[3-methyl-N-(2,2-diphenylacetyl)-L-phenylalanyl]-S-[[3-(methoxycarbonyl)phenyl]methyl]-L-cysteinamide, as a white solid.

D. N-[2-[(3-(methoxycarbonyl)phenyl)thiomethoxy]-1(S)-cyanoethyl]-3-methyl-Nα-(2,2-diphenylacetyl)-L-phenylalaninamide Oxalyl chloride (0.29 mL, 2.90 mmol) is added dropwise to DMF (20 mL), and the resulting solution is cooled to 0° C. After the solution becomes clear, pyridine (0.54 mL, 5.8 mmol) is added, followed by N-[3-methyl-N-(2,2-diphenylacetyl)-L-phenylalanyl]-S-[[3-(methoxycarbonyl)-phenyl]-methyl]-L-cysteinamide (0.90 g, 1.51 mmol), in one portion. The yellow reaction solution is stirred at 0° C. for 1.5 hours, after which time it is diluted with EtOAc (50 mL), and washed with saturated NaHCO$_3$ (1×50 mL), saturated LiCl (1×50 mL), dried over MgSO$_4$, and evaporated. The residue is chromatographed (silica, 33% EtOAc/hexane) to yield N-[2-[(3-(methoxycarbonyl)phenyl)thiomethoxy]-1(S)-cyanoethyl]-3-methyl-Nα-(2,2-diphenylacetyl)-L-phenylalaninamide as a white solid.

Example 308
N-[2-[(3-carboxyphenyl)methanesulfinyl]-1(S)-cyanoethyl]-3-methyl-Nα-2,2-diphenylacetyl-L-phenylalaninamide To a solution of N-[2-[(3-carboxyphenyl)thiomethoxy]-1(S)-cyanoethyl]-3-methyl-Nα-(2,2-diphenylacetyl)-L-phenylalaninamide (89 mg, 0.15 mmol) in acetone (5 mL) is added a solution of potassium peroxymonosulfate (Oxone®, 0.11 g, 0.18 mmol) in water (5 mL) at 0° C., and the solution is stirred at 0° C. for 40 minutes. 5% NaHSO$_4$ (10 mL) is added, and the cloudy suspension is filtered. The solid is washed with water (50 mL), dried in vacuo, and then recrystalized (CH$_2$Cl$_2$, Et$_2$O) to yield N-[2-[(3-carboxyphenyl)methanesulfinyl]-1(S)-cyanoethyl]-3-methyl-Nα-(2,2-diphenylacetyl-L-phenylalaninamide product, as a white solid, m.p. 170–171° C.

Example 309
N-[4-(3-methoxycarbonyl-1H-pyrazol-1-yl)-1(S)-cyanobutyl]-3-methyl-Nα-(2,2-diphenylacetyl)-L-phenylalaninamide A. t-butyl (S)-5-hydroxy-2-(t-butoxycarbonylamino)-pentanoate To a solution of N-(t-butoxycarbonyl)-L-glutamic acid t-butyl ester (6.0 g, 19.78 mmol) and triethylamine (2.83 mL, 20.27 mmol) in THF at −10° C. is added ethyl chloroformate (1.94 mL, 20.27 mmol) dropwise, via syringe, and the solution is stirred at −10° C. for 30 minutes. The solution is filtered to remove precipitate, and the filtrate is added into a solution of NaBH$_4$ (2.3 g, 60.86 mmol) in THF (40 mL) and water (50 mL). This solution is then stirred for 4 hours, after which time the solution is acidified with 1 N HCl to pH=5, and THF is evaporated. The aqueous residue is extracted with EtOAc (3×200 mL), and the organic layers is then washed with 1 N NaOH (2×300 mL), water (300 mL) and brine (300 mL), dried over MgSO$_4$, and evaporated. Chromatography (silica, 20% EtOAc/hexane) yields t-butyl (S)-5-hydroxy-2-(t-butoxycarbonylamino)-pentanoate as a thick oil.

B. t-butyl (S)-5-iodo-2-(t-butoxycarbonylamino)-pentanoate

To a solution of t-butyl (S)-5-hydroxy-2-(t-butoxycarbonylamino)-pentanoate (5.79 g, 20.0 mmol), triphenylphosphine (8.13 g, 31.0 mmol) and imidazole (2.04 g, 30.0 mmol) in CH$_2$Cl$_2$ (200 mL) at room temperature is added iodine (6.35 g, 25.0 mmol), portionwise, over 30 minutes. The mixture is then stirred 16 hours at room temperature. Methanol (20 mL) is added to the solution, which is then stirred an additional 1 hour. Solvent is evaporated, and the residue is purified by chromatography (silica, 33% EtOAc/hexane) to yield t-butyl (S)-5-iodo-2-(t-butoxycarbonylamino)-pentanoate as a clear oil.

C. 3-methyl-Nα-(2,2-diphenylacetyl)-L-phenylalanine N-hydroxysuccinimide ester

A solution of 3-methyl-N-(2,2-diphenylacetyl)-L-phenylalanine (see example 1, 10.93 g, 2.5 mmol) in dioxane (50 mL) at 0° C. is added N-hydroxysuccinimide (0.29 g, 2.5 mmol) in one portion, followed by a solution of DCC (0.52 g, 2.5 mmol) in dioxane (10 mL), which is added dropwise over 10 minutes. The cloudy mixture is warmed to room temperature overnight, after which time it is cooled back to 0° C., and filtered. The filtrate is evaporated to yield 3-methyl-Nα-(2,2-diphenylacetyl)-L-phenylalanine N-hydroxysuccinimide ester as a white solid.

D. t-butyl (S)-5-(3-methoxycarbonyl-1H-pyrazol-1-yl)-2-(t-butoxycarbonylamino)pentanoate To a solution of methyl 1H-pyrazole 3-carboxylate (Synth. Comm., 25, 1995, 761) (0.98 g, 7.74 mmol) in DMF (20 mL) at 0° C. is added NaH (60% suspension, 0.31 g, 7.74 mmol) portionwise, over 10 minutes. After stirring an additional 10 minutes, a solution of t-butyl (S)-5-iodo-2-(t-butoxy-carbonylamino)-pentanoate (2.78 g, 9.29 mmol) in DMF (20 mL) is added over 2 minutes, and the solution is warmed to room temperature over 16 hours. The solvent is evaporated (high-vac), the residue is treated with water (50 mL) and the aqueous layer is extracted with EtOAc (3×80 mL). The combined organic layers are washed with water (2×200 mL) and brine (100 mL), dried over MgSO$_4$, and evaporated. Chromatography (silica, 25% EtOAc/hexane) yields the two regioisomeric products in a 2:1 ratio. The minor product, which is determined to be the desired product, t-butyl (S)-5-(3-methoxycarbonyl-1H-pyrazol-1-yl)-2-(t-butoxycarbonylamino)-pentanoate, is isolated as a thick, clear oil.

E. (S)-5-(-3-methoxycarbonyl-1H-pyrazol-1-yl)-2-aminopentanoic acid.HCl

To a solution of t-butyl (S)-5-(3-methoxycarbonyl-1H-pyrazol-1-yl)-2-(t-butoxycarbonylamino)-pentanoate (0.84 g, 0.21 mmol) in CH$_2$Cl$_2$ (20 mL) at 0° C. is bubbled HCl gas for 30 minutes. Afterward, the solution is warmed to room temperature over 30 minutes. Evaporation of solvent yields (S)-5-(-3-methoxycarbonyl-1H-pyrazol-1-yl)-2-aminopentanoic acid.HCl as a gray-white solid.

F. N-[4-(3-methoxycarbonyl-1H-pyrazol-1-yl)-1(S)-carboxybutyl]-3-methyl-Nα-(2,2-diphenylacetyl)-L-phenylalaninamide To a solution of (S)-5-(-3-methoxycarbonyl-H-pyrazol-1-yl)-2-aminopentanoic acid.HCl (0.67 g, 2.13 mmol) in 10 mL water is added a solution of NaHCO$_3$ (0.72 g, 8.53 mmol) in water (10 mL). After bubbling subsides, a solution of 3-methyl-Nα-(2,2-diphenylacetyl)-L-phenylalanine N-hydroxysuccinimide ester (0.67 g, 2.13 mmol) in 20 mL dioxane is added dropwise over 10 minutes, and the solution is stirred at room temperature for 16 hours. Solvent is then evaporated, and the residue is diluted with water (50 mL) and adjusted to pH 4 with 1 N HCl. The aqueous layer is extracted with EtOAc (3×80 mL), and the combined extracts are washed with brine (2×100 mL), dried over MgSO$_4$, evaporated, and triturated from Et$_2$O to yield N-[4-(3-methoxycarbonyl-1H-pyrazol-1-yl)-1(S)-carboxybutyl]-3- methyl-Nα-(2,2-diphenylacetyl)-L-phenylalaninamide, which is carried on directly.

G. N-[4-(3-methoxycarbonyl-1H-pyrazol-1-yl)-1(S)aminocarbonyl)-butyl]-3-methyl-Nα-2,2-diphenylacetyl)-L-phenylalaninamide A solution of N-[4-(3-methoxycarbonyl-1H-pyrazol-1-yl)-1(S)-carboxybutyl]-3-methyl-Nα-(2,2-diphenylacetyl)-L-phenylalaninamide (0.3 g, 0.5 mmol)) and N-methylmorpholine (0.17 mL, 1.5 mmol) in $CH_2Cl_2$ (50 mL) is cooled to –10° C., and isobutyl chloroformate (0.065 mL, 0.5 mmol) is added dropwise over 10 minutes. After stirring for 15 minutes, ammnonia gas is bubbled into the solution at a moderately vigorous rate for 15 minutes. The solution is then warmed to room temperature over 30 min. $CH_2Cl_2$ is evaporated, the residue is treated with water (30 mL). The suspension is adjusted to pH=7 with 1 N HCl, and filtered. The solid is washed with water (50 mL) and dried in vacuo to yield N-[4-(3-methoxycarbonyl-1H-pyrazol-1-yl)-1(S)-(aminocarbonyl)-butyl]-3-methyl-Nα-(2,2-diphenylacetyl)-L-phenylalaninamide.

H. N-[4-(3-methoxycarbonyl-1H-pyrazol-1-yl)-1(S)-cyanobutyl]-3-methyl-Nα-(2,2-diphenylacetyl)-L-phenylalaninamide Oxalyl chloride (0.082 mL, 0.94 mmol) is added dropwise to DMF (20 mL), and the resulting solution is cooled to 0° C. After the solution becomes clear, pyridine (0.15 mL, 1.88 mmol) is added, followed by N-[4-(3-methoxycarbonyl-1H-pyrazol-1-yl)-1(S)-(aminocarbonyl)butyl]-3-methyl-Nα-(2,2-diphenyl-acetyl)-L-phenylalaninamide (0.28 g, 0.47 mmol), in one portion. The yellow reaction solution is stirred at 0° C. for 1.5 hours, after which time it is diluted with EtOAc (50 mL), and washed with saturated $NaHCO_3$ (1×50 mL), saturated LiCl (1×50 mL), dried over $MgSO_4$, and evaporated. The residue is chromatographed (silica, 66% EtOAc/hexane) to yield N-[4-(3-methoxycarbonyl-1H-pyrazol-1-yl)-1(S)-cyanobutyl]-3-methyl-Nα-(2,2-diphenylacetyl)-L-phenylalaninamide as a white solid.

Example 310
N-[4-(3-methoxycarbonyl-phenyl)-1(S)-cyanobutyl]-3-methyl-Nα-(2,2-diphenylacetyl)-L-phenylalaninamide A. N-(t-butoxycarbonyl)-(S)-propargylglycineamide To a solution of N-(t-butoxycarbonyl)-(S)-propargylglycine (2.44 g, 11.45 mmol) in $CH_2Cl_2$ (50 mL) is added N-methylmorpholine (3.78 mL, 34.4 mmol) in one portion. The solution is then cooled to –10° C, and isobutyl chloroformate is added dropwise over 5 minutes. After stirring for 15 minutes, ammonia gas is bubbled into the reaction mixture at a moderately vigorous rate for 15 minutes. The resulting milky suspension is then warmed to room temperature over 2 hours, and the mixture is washed with 1 N HCl (2×25 mL), aqueous $NaHCO_3$ (25 mL) and brine (25 mL), and then dried over $MgSO_4$. Evaporation of solvent, followed by chromatography (silica, 65% EtOAc/hexane) yields N-(t-butoxycarbonyl)-(S)-propargylglycineamide, as a clear oil.

B. (S)-2-(t-butoxycarbonylamino)-5-(3-carbomethoxyphenyl)-4-pentynoic acid amide A solution of N-(t-butoxycarbonyl)-(S)-propargylglycineamide (1.15 g, 5.33 mmol), methyl 3-bromobenzoate (1.15 g, 5.33 mmol), and Cu(I)I (0.041 g, 0.214 mmol) in triethylamine (25 mL) is deoxygenated with bubbling $N_2$ for 2–3 minutes. Bis(triphenylphosphine) palladium dichloride (0.075 g, 0.11 mmol) is then added in one portion, and the mixture is refluxed for 3 hours, after which time solvent is evaporated. The residue is then taken up in EtOAc (10 ml), and then washed with 1 N HCl (40 mL) and brine (30 mL), and then dried over $MgSO_4$. The residue is chromatographed (silica, 80% EtOAc/hexane) to yield (S)-2-(t-butoxycarbonylamino)-5-(3-carbomethoxyphenyl)4-pentynoic acid amide, as a light yellow solid.

C. (S)-2-butoxycarbonylamino4-(3-carbomethoxyphenyl)-pentanamide

To a solution of (S)-2-(t-butoxycarbonylamino)-5-(3-carbomethoxyphenyl)-4-pentynoic acid amide (1.11 g, 3.22 mmol) in 1:1 ethanol/THF (50 mL) is added 10% Pd/C (0.5 g), and the mixture is hydrogenated at 1 atm. for 1.5 hours. The mixture is filtered through celite, and evaporated to yield (S)-2-butoxycarbonylamino-4-(3-carbomethoxyphenyl)-pentanamide, as a clear oil.

D. (S)-2-amino4-(3-carbomethoxyphenyl)-pentanamide HCl

To a solution of (S)-2-(t-butoxycarbonylamino)-5-(3-carbomethoxyphenyl)-pentanamide (1.22 g, 3.5 mmol) in EtOAc (75 mmol) at 0° C. is bubbled HCl gas at a moderately vigorous rate, for 5 minutes. The solution is then warmed to room temperature for 30 minutes Evaportion of solvent yields (S)-2-amino4-(3-carbomethoxyphenyl)-pentanamide HCl salt as a light yellow solid.

E. N-[4-(3-methoxycarbonyl-phenyl)-1(S)-(aminocarbonyl)-butyl]-3-methyl-Nα-(2,2-diphenylacetyl)-L-phenylalaninamide To a solution of (S)-2-amino-5-(3-carbomethoxyphenyl)-pentanamide HCl (0.30 g, 0.80 mmol), of 3-methyl-N-(2,2-diphenylacetyl)-L-phenylalanine (0.23 g, 0.80 mmol), 1-hydroxybenzotriazole hydrate (0.135 g, 0.89 mmol) and N-methylmorpholine (0.35 ml, 3.2 mmol) in $CH_2Cl_2$ (25 mL) is added 1-(3-dimethylaminopropyl)-3-ethylcarbodiimide.HCl (0.23 g, 1.2 mmol) in one portion, and the mixture is stirred at room temperature for 16 hours. The solution is then washed with 1 N HCl (100 mL), saturated aqueous $NaHCO_3$ (1×50 mL), water (1×50 mL) and brine (1×50 mL), dried over $MgSO_4$, and evaporated. The residual solid is triturated with ether to yield N-[4-(3-methoxycarbonyl-phenyl)-1(S)-(aminocarbonyl)-butyl]-3-methyl-Nα-(2,2-diphenylacetyl)-L-phenylalaninamide as a light yellow solid.

F. N-[4-(3-methoxycarbonyl-phenyl)-1(S)-cyanobutyl]-3-methyl-Nα-(2,2-diphenylacetyl)-L-phenylalaninamide Oxalyl chloride (0.12 mL, 1.39 mmol) is added dropwise to DMF (10 mL), and the resulting solution is cooled to 0° C. After the solution is clear, pyridine (0.22 mL, 2.78 mmol) is added, followed by N-[4-(3-methoxycarbonylphenyl)-1(S)-(aminocarbonyl)butyl]-3-methyl-Nα-(2,2-diphenylacetyl)-L-phenylalaninamide (0.42 g, 0.70 mmol), in one portion. The yellow reaction solution is stirred at 0° C. for 1.5 hours, after which time it is diluted with EtOAc (50 mL), and washed with saturated aqueous $NaHCO_3$ solution (1×50 mL), saturated aqueous LiCl solution (1×50 mL), dried over $MgSO_4$, and evaporated. The residue is chromatographed to yield N-[4-( 3-methoxycarbonyl-phenyl)-1(S)-cyanobutyl]-3-methyl-Nα-(2,2-diphenylacetyl)-L-phenylalaninamide, as a yellow solid.

By repeating the procedure described above in Examples 302 to 310, using appropriate starting materials and conditions the following compounds of formula XVIII are obtained as identified below in Table 11.

TABLE 11
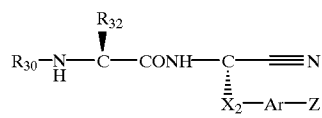
XVIII
| Example | R30 | R32 | X2 | -Ar | Z | mp. (° C.) | MS (M + 1) |
|---|---|---|---|---|---|---|---|
| 311 | morpholine-N-CO | 3-methylbenzyl (CH3, CH2-) | -CH2-O-CH2- | 3-methylphenyl | COOH | 100 dec. | |
| 312 | 3,4-dimethoxyphenyl-C(=O)- | " | " | " | " | 142–145 | |
| 313 | CH3CO | " | " | " | " | 171–172 | |
| 314 | phenyl-C(=O)- | " | " | " | " | 173–175 | |
| 315 | phenyl-CH(3-pyridyl)-C(=O)- Isomer 1 | " | " | " | " | 120 dec. | |
| 316 | phenyl-CH(3-pyridyl)-C(=O)- Isomer 2 | " | " | " | " | 90 dec. | |

TABLE 11-continued
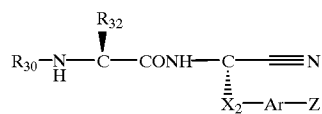
XVIII
| Example | R₃₀ | R₃₂ | X₂ | -Ar | Z | mp. (° C.) | MS (M + 1) |
|---|---|---|---|---|---|---|---|
| 317 | (di-pyridin-3-yl-CH-CO-) | " | " | " | " |  | 578 |
| 318 | 4-CH₃O-C₆H₄-CO- | " | " | " | " | 139–141 |  |
| 319 | 3-CH₃O-C₆H₄-CO- | " | " | " | " | 153–155 |  |
| 320 | Ph-CH(CH₃)-CO- | " | " | " | " | 129–131 |  |
| 321 | pyridin-3-yl-CO- | " | " | " | " | 170–172 |  |
| 322 | Ph-SO₂- | " | " | " | " |  | 522 |
| 323 | 4-CH₃-C₆H₄-SO₂- | " | " | " | " |  | 536 |
| 324 | 4-(CH₃)₂N-C₆H₄-CO- | " | " | " | " |  | 529 |
| 325 | pyridin-4-yl-CO- TFA salt | " | " | " | " |  | 601 |

TABLE 11-continued
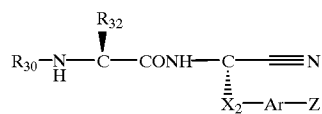
XVIII
| Example | R30 | R32 | X2 | -Ar | Z | mp. (°C.) | MS (M + 1) |
|---|---|---|---|---|---|---|---|
| 326 | 2-naphthyl-SO2- | " | " | " | " | | 572 |
| 327 | 4-Br-C6H4-SO2- | " | " | " | " | | 600, 602 |
| 328 | C4H9-SO2- | " | " | " | " | | 502 |
| 329 | 2-CH3-C6H4-SO2- | " | " | " | " | | 536 |
| 330 | 4-C3H7-C6H4-SO2- | " | " | " | " | | 564 |
| 331 | 2-F-C6H4-SO2- | " | " | " | " | | 540 |
| 332 | 3-Cl-C6H4-SO2- | " | " | " | " | | 556 |
| 333 | 3-F-C6H4-SO2- | " | " | " | " | | 540 |
| 334 | 3,4-diCl-C6H3-SO2- | " | " | " | " | | 590 |

TABLE 11-continued
XVIII
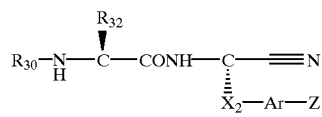
| Example | R30 | R32 | X2 | -Ar | Z | mp. (° C.) | MS (M + 1) |
|---|---|---|---|---|---|---|---|
| 335 | 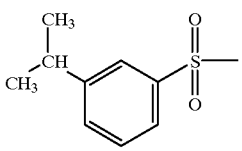 | " | " | " | " | | 564 |
| 336 | 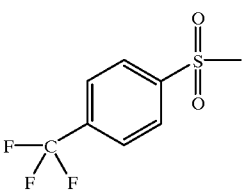 | " | " | " | " | | 590 |
| 337 | 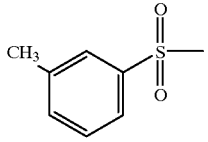 | " | " | " | " | | 536 |
| 338 | 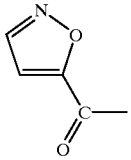 | " | " | " | " | | 540 |
| 339 | CH₃(CH₂)₂C(O)— |  | " | " | " | | 468 |
| 340 | 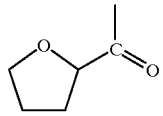 | " | " | " | " | | 496 |
| 341 | CH₃(CH₂)₂C(O)— | 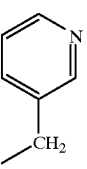 | " | " | " | | 439 |

TABLE 11-continued
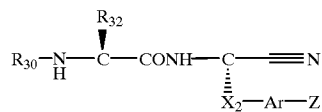
XVIII
| Example | R30 | R32 | X2 | -Ar | Z | mp. (° C.) | MS (M + 1) |
|---|---|---|---|---|---|---|---|
| 342 | (tetrahydrofuran-2-carbonyl) | " | " | " | " | | 467 |
| 343 | (α-methoxy-phenylacetyl) | (isothiazol-3-yl-CH2) | " | " | " | | 523 |
| 344 | (2-chlorobenzoyl) | (3-methylbenzyl) | " | " | " | | 520 |
| 345 | (cyclohexanecarbonyl) | " | " | " | " | | 520 |
| 346 | (phenylacetyl) | " | " | " | " | | 501 |
| 347 | (2-methylbenzoyl) | " | " | " | " | | 500 |
| 348 | CH3CH2O—C(O)— | " | " | " | " | | 454 |
| 349 | (thien-2-yl-CH2-C(O)) | " | " | " | " | | 506 |
| 350 | (furan-2-carbonyl) | " | " | " | " | | 476 |
| 351 | (4-chlorobenzoyl) | " | " | " | " | | 520 |

TABLE 11-continued
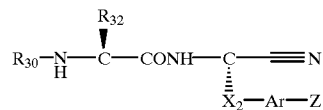
XVIII
| Example | R30 | R32 | X2 | –Ar | Z | mp. (° C.) | MS (M + 1) |
|---|---|---|---|---|---|---|---|
| 352 | 3,5-bis(CF₃)-C₆H₃-C(O)- | " | " | " | " |  | 622 |
| 353 | C₆H₅-O-C(O)- | " | " | " | " |  | 502 |
| 354 | CH₃-S(O)₂- | " | " | " | " |  | 460 |
| 355 | CH₃(CH₂)₂C(O)— | " | " | " | " |  | 452 |
| 356 | 3-NO₂-C₆H₄-C(O)- | " | " | " | " |  | 531 |
| 357 | 5-NO₂-furan-2-C(O)- | " | " | " | " |  | 521 |
| 358 | 4-Br-C₆H₄-C(O)- | " | " | " | " |  | 564, 566 |
| 359 | C₆H₅-S(O)₂- | " | " | " | " |  | 522 |
| 360 | C₆H₅-O-CH₂-C(O)- | " | " | " | " |  | 516 |
| 361 | CH₃O-C(O)-(5-CH₃SO₂-thien-2-yl) | " | " | " | " |  | 586 |

TABLE 11-continued
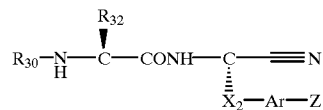
XVIII
| Example | R$_{30}$ | R$_{32}$ | X$_2$ | -Ar | Z | mp. (° C.) | MS (M + 1) |
|---|---|---|---|---|---|---|---|
| 362 | C$_4$H$_9$-C$_6$H$_4$-C(O)- | " | " | " | " |  | 558 |
| 363 | PhCH$_2$OC(O)- | " | " | " | " |  | 516 |
| 364 | CH$_3$OCH$_2$C(O)— | " | " | " | " |  | 454 |
| 365 | 1-naphthyl-SO$_2$- | " | " | " | " |  | 572 |
| 366 | 2-NO$_2$-C$_6$H$_4$-SO$_2$- | " | " | " | " |  | 567 |
| 367 | CH$_3$(CH$_2$)$_2$CO | indol-3-yl-CH$_2$ | " | " | " |  | 477 |
| 368 | tetrahydrofuran-2-yl-C(O)- | " | " | " | " |  | 505 |
| 369 | PhCH(OCH$_3$)C(O)- | " | " | " | " |  | 555 |
| 370 | CH$_3$(CH$_2$)$_2$C(O)— | 1-methylimidazol-5-yl-CH$_2$ | " | " | " |  | 442 |

TABLE 11-continued
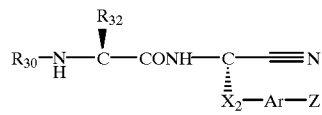
XVIII
| Example | R30 | R32 | X2 | -Ar | Z | mp. (° C.) | MS (M + 1) |
|---|---|---|---|---|---|---|---|
| 371 | (2-tetrahydrofuranyl-C(O)-) | " | " | " | " | | 470 |
| 372 | (2-methoxybenzyl-C(O)-) | " | " | " | " | | 520 |
| 373 | (2-tetrahydrofuranyl-C(O)-) TFA salt | (4-thiazolyl-CH2-) | " | " | " | | 473 |
| 374 | (α-methoxybenzyl-C(O)-) | " | " | " | " | | 523 |
| 375 | CH3(CH2)2C(O)— | " | " | " | " | | 445 |
| 376 | (3-pyridyl-C(O)-) | (5-methyl-2-furyl-CH2-) | " | " | " | | 477 |
| 377 | (3,4-methylenedioxyphenyl-C(O)-) | " | " | " | " | | 520 |
| 378 | (2-quinoxalinyl-C(O)-) | " | " | " | " | | 528 |
| 379 | (5-isoxazolyl-C(O)-) | (cyclohexyl-CH2-) | " | " | " | | 469 |

TABLE 11-continued
XVIII
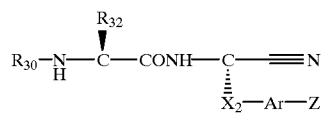
| Example | R₃₀ | R₃₂ | X₂ | -Ar | Z | mp. (°C.) | MS (M + 1) |
|---|---|---|---|---|---|---|---|
| 380 | 3-acetylpyridine | " | " | " | " | | 479 |
| 381 | acetyl-benzodioxole | " | " | " | " | | 522 |
| 382 | 2-acetylquinoxaline | " | " | " | " | | 530 |
| 383 | diphenyl-acetone | 3-methylbenzyl (CH₂) | —(CH₂)₂—O— | " | " | 169–170 | |
| 384 | " | " | —CH₂—O—CH₂— | 2,5-dimethylfuran | " | 115 dec. | |
| 385 | " | " | —CH₂—S—CH₂— | 1,3-dimethylbenzene | " | 145–146 | |
| 386 | " | " | —(CH₂)₃— | 1,3-dimethylpyrazole | " | 145–146 | |
| 387 | " | " | " | 1,3-dimethylbenzene | " | 132 | |
| 388 | 2-acetylbenzothiophene | 3-methylindole | —CH₂—O—CH₂— | " | " | | 567 |

TABLE 11-continued
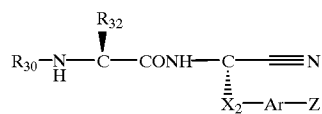
XVIII
| Example | R30 | R32 | X2 | -Ar | Z | mp. (°C.) | MS (M + 1) |
|---|---|---|---|---|---|---|---|
| 389 | 4-CH3-C6H4-C(O)- | 4-CH3O-C6H4-CH2- | " | " | " | | 516 |
| 390 | 4-Cl-C6H4-C(O)- | " | " | " | " | | 577 |
| 391 | 3,4-diCl-C6H3-C(O)- | " | " | " | " | | 571 |
| 392 | 3-Cl-C6H4-C(O)- | " | " | " | " | | 537 |
| 393 | 4-Cl-C6H4-C(O)- | cyclohexyl-CH2- | " | " | " | | 512 |
| 394 | 4-CH3-C6H4-C(O)- | indol-3-yl-CH2- | " | " | " | | 525 |
| 395 | 4-Cl-C6H4-C(O)- | " | " | " | " | | 545 |
| 396 | 3,4-diCl-C6H3-C(O)- | " | " | " | " | | 579 |

TABLE 11-continued

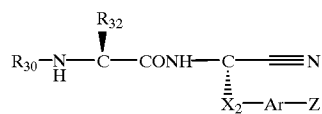

XVIII

| Example | R30 | R32 | X2 | -Ar | Z | mp. (° C.) | MS (M + 1) |
|---|---|---|---|---|---|---|---|
| 397 | 2-acetyl-benzothiophene | neopentyl (CH2C(CH3)3) | " | " | " | | 508 |
| 398 | 3,4-dichlorophenacyl | 5-methylfuran-2-ylmethyl | " | " | " | | 544.9 |
| 399 | 4-chlorophenacyl | 4-methoxybenzyl | " | " | " | | 537 |
| 400 | 4-methylphenacyl | cyclohexylmethyl | " | " | " | | 490 |
| 401 | 3,4-dichlorophenacyl | isobutyl (CH(CH3)2 CH) | " | " | " | | 492 |
| 402 | " | thiophen-2-ylmethyl | " | " | " | | 547.5 |
| 403 | 4-chlorophenacyl | indol-3-ylmethyl | " | " | " | | 543 (M-1) |
| 404 | 4-(dimethylamino)phenacyl | 3,4-dichlorobenzyl | " | " | " | | 582.8 |

TABLE 11-continued
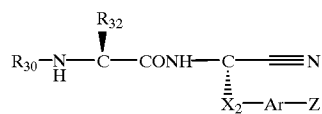
XVIII
| Example | R30 | R32 | X2 | -Ar | Z | mp. (°C.) | MS (M + 1) |
|---|---|---|---|---|---|---|---|
| 405 | 3,4-dimethylphenyl-C(O)- | " | " | " | " | | 567.2 |
| 406 | 4-methylphenyl-C(O)- | " | " | " | " | | 553.1 |
| 407 | 4-chlorophenyl-C(O)- | " | " | " | " | | 573.9 |
| 408 | 3,4-dichlorophenyl-C(O)- | " | " | " | " | | 609.6 |
| 409 | 3-chlorophenyl-C(O)- | 3-chlorobenzyl-CH2 | " | " | " | | 540 |
| 410 | 4-methylphenyl-C(O)- | " | " | " | " | | 520.03 |
| 411 | 4-chlorophenyl-C(O)- | " | " | " | " | | 540.1 |
| 412 | benzothiophen-2-yl-C(O)- | " | " | " | " | | 571 |

TABLE 11-continued

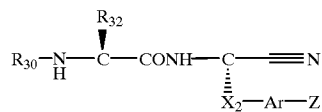

XVIII

| Example | R30 | R32 | X2 | -Ar | Z | mp. (° C.) | MS (M + 1) |
|---------|-----|-----|-----|-----|---|------------|-----------|
| 413 | 3,4-dichlorobenzoyl | " | " | " | " |  | 573.9 |
| 414 | 3,4-dimethylbenzoyl | " | " | " | " |  | 534 |
| 415 | 4-fluorobenzoyl | 3-methylbenzyl | " | " | " | 161–162 |  |
| 416 | 2,4-difluorobenzoyl | " | " | " | " | 145–146 | 590 (M⁺–1) |
| 417 | 4-chlorobenzoyl | 3-chlorobenzyl | —CH₂—C(O)—NH— | " | " |  | 553.4 |
| 418 | 2,4-difluorobenzoyl | " | " | " | 4-fluoro-2,5-dimethylphenyl |  | 126–128 |  |
| 419 | 2-fluorobenzoyl | " | " | " | 3,5-dimethylphenyl | 159–162 |  |

The compounds of Examples 302 to 419 are selective inhibitors of cathepsin B, having IC$_{50}$s for inhibition of cathepsin B, in the in vitro cathepsin B assay described above, which are typically in the range from about 5 nM to about 1000 nM. Illustrative of the invention, the IC$_{50}$ in the in vitro cathepsin B assay is about 5 nM for the compound of example 303.

In view of their properties as selective or broad based inhibitors of cathepsin L, S and/or B the Compounds of the Invention described above in Examples 154 to 419 may be used for treatment or prophylaxis of diseases or medical conditions mediated by cathepsin L, S or B; for instance as hereinbefore described.

Example 420

Preparation of 1,000 capsules each containing 25 mg of a Compound of the Invention, using the following ingredients:

| | |
|---|---|
| Compound of the Invention | 25.00 g |
| Lactose | 192.00 g |
| Modified starch | 80.00 g |
| Magnesium stearate | 3.00 g |

Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:

1. A compound of formula III

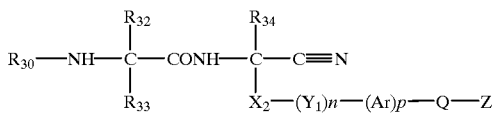

wherein $R_{30}$ is an acyl group derived from an organic carboxylic, carbamic or sulfonic acid;

$R_{32}$ and $R_{33}$ are independently hydrogen, lower alkyl, cycloalkyl, bicycloalkyl, or (aryl, biaryl, cycloalkyl or bicycloalkyl)-lower alkyl; or $R_{32}$ and $R_{33}$ together represent lower alkylene so as to form a ring together with the carbon to which they are attached;

$R_{34}$ is hydrogen or lower alkyl;

$Y_1$ is O, S, SO, $SO_2$, $N(R_6)SO_2$, N—$R_6$, $SO_2NR_6$, $CONR_6$ or $NR_6CO$;

n is zero or one;

p is zero or one;

$X_2$ is lower alkylene; or when n is zero, $X_2$ is also $C_2$–$C_7$-alkylene interrupted by O, S, SO, $SO_2$, $NR_6$, $SO_2NR_6$, $CONR_6$ or $NR_6CO$;

wherein $R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl;

Q is a direct bond, lower alkylene, $Y_1$-lower alkylene or $C_2$–$C_7$-alkylene interrupted by $Y_1$;

or a pharmaceutically acceptable salt or ester thereof.

2. A compound according to claim 1, wherein (a) p is one;

(b) $Y_1$ is O, S, SO, $SO_2$, $N(R_6)SO_2$ or N—$R_6$; and (c) $X_2$ is lower alkylene; or when n is zero, $X_2$ is also $C_2$–$C_7$-alkylene interrupted by O, S, SO, $SO_2$ or $NR_6$, or a pharmaceutically acceptable salt or ester thereof.

3. A compound of formula IV

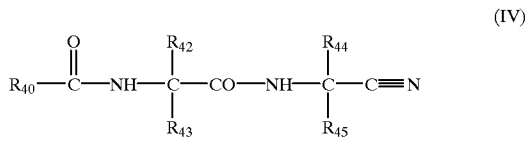

wherein $R_{40}$ is substituted phenyl or heterocyclic aryl, (mono- or di-carbocyclic or heterocyclic aryl)-lower alkyl or lower alkenyl, or heterocyclyl;

$R_{42}$ is hydrogen or lower alkyl;

$R_{43}$ is carbocyclic or heterocyclic aryl-lower alkyl;

$R_{44}$ and $R_{45}$ are independently hydrogen or lower alkyl; or $R_{44}$ and $R_{45}$ combined represent lower alkylene;

or a pharmaceutically acceptable salt or ester thereof.

4. A compound according to claim 1 the formula V'

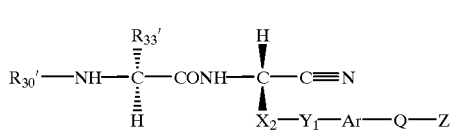

wherein the symbols are as defined in said claim, or a physiologically-acceptable and -cleavable ester or salt thereof.

5. A compound according to claim 3 of the formula V"

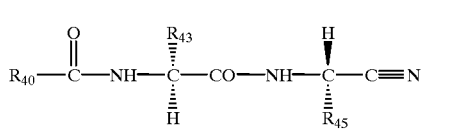

wherein the symbols are as defined in said claim, or a physiologically-acceptable and -cleavable ester or salt thereof.

6. A method of inhibiting cathepsin activity in a mammal which comprises administering to a mammal in need thereof an effective amount of a cathepsin inhibiting pharmaceutical composition comprising a compound of formula I, or a physiologically-acceptable and -cleavable ester, or a salt thereof

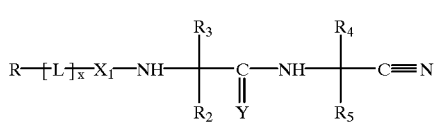

wherein:

R is optionally substituted (aryl, lower alkenyl, lower alkynyl or heterocyclyl), or substituted lower alkyl;

$R_2$ and $R_3$ are independently hydrogen, or optionally substituted; or $R_2$ and $R_3$ together represent lower alkylene, optionally interrupted by O, S or $NR_6$ so as to form a ring with the carbon atom to which they are attached; and $R_6$ is hydrogen, lower alkyl or aryl-lower alkyl; or either $R_2$ or $R_3$ are linked by lower alkylene to the adjacent nitrogen to form a ring;

$R_4$ and $R_5$ are independently H, or optionally substituted (lower alkyl or aryl-lower alkyl), —C(O)OR$_7$, or —C(O)NR$_7$R$_8$, wherein $R_7$ is optionally substituted (lower alkyl, aryl, aryl-lower alkyl, cycloalkyl, bicycloalkyl or heterocyclyl), and $R_8$ is H, or optionally substituted (lower alkyl, aryl, aryl-lower alkyl, cycloalkyl, bicycloalkyl or heterocyclyl); or $R_4$ and $R_5$ together represent lower alkylene, optionally interrupted by O, S or NR$_6$, so as to form a ring with the carbon atom to which they are attached; and $R_6$ is hydrogen, lower alkyl or aryl-lower alkyl; or $R_4$ is H or optionally substituted lower alkyl and $R_5$ is a substituent of formula —X$_2$—(Y$_1$)$_n$—(Ar)$_p$—Q—Z wherein $Y_1$ is O, S, SO, SO$_2$, N(R$_6$)SO$_2$, N—R$_6$, SO$_2$NR$_6$, CONR$_6$ or NR$_6$CO;

n is zero or one;

p is zero or one;

$X_2$ is lower alkylene; or when n is zero, $X_2$ is also $C_2$–$C_7$-alkylene interrupted by O, S, SO, SO$_2$, NR$_6$, SO$_2$NR$_6$, CONR$_6$ or NR$_6$CO; and $R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl;

Q is a direct bond, lower alkylene, Y$_1$-lower alkylene or $C_2$–$C_7$-alkylene interrupted by $Y_1$;

$X_1$ is —C(O)—, —C(S)—, —S(O)—, —S(O)$_2$—, or —P(O)(OR$_6$)— wherein $R_6$ is as defined above;

Y is oxygen or sulphur;

L is optionally substituted —Het—, —Het—CH$_2$ or —CH$_2$Het, and Het is a hetero atom selected from O, N or S; and x is zero or one;

and aryl in the above definitions represents carbocyclic or heterocyclic aryl;

in combination with a pharmaceutically acceptable carrier.

7. A compound of formula I, or a physiologically-acceptable and -cleavable ester or a salt thereof

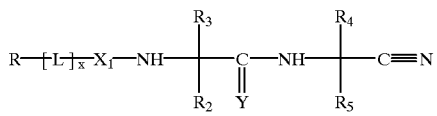

wherein:

R is optionally substituted (aryl, aryl-lower alkyl, lower alkenyl, lower alkynyl, heterocyclyl or heterocyclyl-lower alkyl);

$R_2$ and $R_3$ together represent lower alkylene, optionally interrupted by O, S or NR$_6$, so as to form a ring with the carbon atom to which they are attached, and $R_6$ is hydrogen, lower alkyl or aryl-lower alkyl;

$R_4$ and $R_5$ are independently H, or optionally substituted (lower alkyl or aryl-lower alkyl), —C(O)OR$_7$, or —C(O)NR$_7$R$_8$, wherein $R_7$ is optionally substituted (lower alkyl, aryl, aryl-lower alkyl, cycloalkyl, bicycloalkyl or heterocyclyl), and $R_8$ is H, or optionally substituted (lower alkyl, aryl, aryl-lower alkyl, cycloalkyl, bicycloalkyl or heterocyclyl); or $R_4$ and $R_5$ together represent lower alkylene, optionally interrupted by O, S or NR$_6$, so as to form a ring with the carbon atom to which they are attached, and $R_6$ is hydrogen, lower alkyl or aryl-lower alkyl; or $R_4$ is H or optionally substituted lower alkyl and $R_5$ is a substituent of formula —X$_2$—(Y$_1$)$_n$—(Ar)$_p$—Q—Z wherein $Y_1$ is O, S, SO, SO$_2$, N(R$_6$)SO$_2$, N—R$_6$, SO$_2$NR$_6$, CONR$_6$ or NR$_6$CO;

n is zero or one;

p is zero or one;

$X_2$ is lower alkylene; or when n is zero, $X_2$ is also $C_2$–$C_7$-alkylene interrupted by O, S, SO, SO$_2$, NR$_6$, SO$_2$NR$_6$, CONR$_6$ or NR$_6$CO, and $R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl;

Q is a direct bond, lower alkylene, Y$_1$-lower alkylene or $C_2$–$C_7$-alkylene interrupted by $Y_1$;

$X_1$ is —C(O)—, —C(S)—, —S(O)—, —S(O)$_2$—, or —P(O)(OR$_6$)—, and $R_6$ is as defined above;

Y is oxygen or sulphur;

L is optionally substituted —Het—, —Het—CH$_2$— or —CH$_2$—Het—, and Het is a hetero atom selected from O, N or S; and x is zero or one;

and aryl in the above definitions represents carbocyclic or heterocyclic aryl.

8. A compound according to claim 7 of formula II, or a physiologically-acceptable and -cleavable ester, or a salt thereof

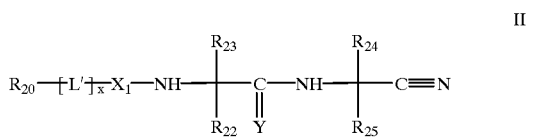

wherein:

$R_{20}$ is optionally substituted (aryl, aryl-lower alkyl, lower alkenyl, lower alkynyl, heterocyclyl, or heterocyclyl-lower alkyl);

$R_{22}$ and $R_{23}$ together with the carbon atom to which they are attached form an optionally substituted (cycloalkyl group or heterocycloalkyl group);

$R_{24}$ and $R_{25}$ are independently H, optionally substituted (lower alkyl or aryl-lower alkyl), —C(O)OR$_7$, or —C(O)NR$_7$R$_8$, and $R_7$ and $R_8$ are as defined in claim 7; or $R_{24}$ and $R_{25}$ together with the carbon atom to which they are attached form an optionally substituted (cycloalkyl group or heterocycloalkyl group);

$X_1$ is as defined in claim 7;

Y is oxygen or sulphur;

L' is optionally substituted (—Het—CH$_2$— or —CH$_2$—Het—), wherein Het is a hetero atom selected from O, N or S; and x is zero or one.

9. A compound of formula II' or a physiologically-acceptable and -cleavable ester or a salt thereof

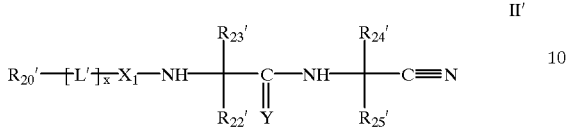

wherein:

$R_{20}'$ is optionally substituted ($C_6$–$C_{18}$ aryl or $C_4$–$C_{18}$ heteroaryl);

$R_{22}'$ and $R_{23}'$ together with the carbon atom to which they are attached form an optionally substituted ($C_3$–$C_8$ cycloalkyl group or $C_4$–$C_7$ heterocycloalkyl group);

$R_{24}'$ and $R_{25}'$ are independently H, or optionally substituted ($C_1$–$C_8$ alkyl, $C_7$–$C_{14}$ aralkyl, or $C_5$–$C_{14}$ heteroaralkyl), —C(O)OR$_6$', or —C(O)NR$_6$'R$_7$'; wherein R$_6$' is optionally substituted ($C_1$–$C_8$ alkyl, $C_7$–$C_{14}$ aralkyl, $C_3$–$C_8$ cycloalkyl, $C_4$–$C_7$ heterocycloalkyl, $C_5$–$C_{14}$ heteroaralkyl, $C_6$–$C_{14}$ aryl, or $C_4$–$C_{14}$ heteroaryl), and R$_7$' is H, or optionally substituted ($C_1$–$C_8$ alkyl, $C_7$–$C_{14}$ aralkyl, $C_3$–$C_8$ cycloalkyl, $C_4$–$C_7$ heterocycloalkyl, $C_5$–$C_{14}$ heteroaralkyl, $C_6$–$C_{14}$ aryl, or $C_4$–$C_{14}$ heteroaryl); or $R_{24}'$ and $R_{25}'$ together with the carbon atom to which they are attached form an optionally substituted ($C_3$–$C_8$ cycloalkyl group or $C_4$–$C_7$ heterocycloalkyl group);

$X_1$ is —C(O)—, —C(S)—, —S(O)—, —S(O)$_2$—, —P(O)(OR$_6$')— wherein R$_6$' is as defined above;

Y is oxygen or sulphur;

L' is optionally substituted (—Het—CH$_2$— or —CH$_2$—Het—), wherein Het is a hetero atom selected from O, N or S; and x is zero or one.

10. A method of inhibiting cathepsin activity in a mammal which comprises administering to a mammal in need thereof are effective amount of a cathepsin inhibiting pharmaceutical composition comprising a compound of formula III

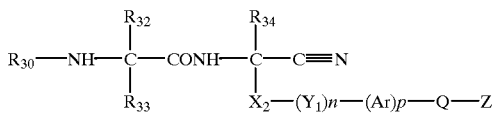

wherein $R_{30}$ is an acyl group derived from an organic carboxylic, carbonic, carbamic or sulfonic acid;

$R_{32}$ and $R_{33}$ are independently hydrogen, lower alkyl, cycloalkyl, bicycloalkyl, or (aryl, biaryl, cycloalkyl or bicycloalkyl)-lower alkyl; or $R_{32}$ and $R_{33}$ together represent lower alkylene so as to form a ring together with the carbon to which they are attached;

$R_{34}$ is hydrogen or lower alkyl;

$Y_1$ is O, S, SO, SO$_2$, N(R$_6$)SO$_2$, N—R$_6$, SO$_2$NR$_6$, CONR$_6$ or NR$_6$CO;

n is zero or one;

p is zero or one;

$X_2$ is lower alkylene; or when n is zero, $X_2$ is also $C_2$–$C_7$-alkylene interrupted by O, S, SO, SO$_2$, NR$_6$, SO$_2$NR$_6$, CONR$_6$ or NR$_6$CO;

$R_6$ is hydrogen, lower alkyl or aryl-lower alkyl;

Ar is arylene;

Z is hydroxy, acyloxy, carboxyl, esterified carboxyl, amidated carboxyl, aminosulfonyl, (lower alkyl or aryl-lower alkyl)aminosulfonyl, or (lower alkyl or aryl-lower alkyl)sulfonylaminocarbonyl; or Z is tetrazolyl, triazolyl or imidazolyl;

Q is a direct bond, lower alkylene, Y$_1$-lower alkylene or $C_2$–$C_7$-alkylene interrupted by Y$_1$;

or a pharmaceutically acceptable salt or ester thereof;

in combination with a pharmaceutically acceptable carrier.

11. A compound according to claim 8 wherein $R_{22}$ and $R_{23}$ together with the carbon to which they are attached form a $C_5$–$C_8$-cycloalkyl group.

12. A compound according to claim 11 wherein $R_{22}$ and $R_{23}$ together with the carbon to which they are attached form a $C_6$-cycloalkyl group.

13. A compound according to claim 12 wherein Y is oxygen; X$_1$ is —C(O)—; x is zero; and $R_{24}$ and $R_{25}$ are both H or CH$_3$.

14. A compound according to claim 7 wherein R is phenyl or substituted phenyl comprising 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-1-yl, 4-(imidazol-1-ylmethyl)-phen-1-yl, 4-(morpholin-1-yl)-phen-1-yl, 4-(morpholin-1-ylmethyl)-phen-1-yl, 4-(methoxyethylaminomethyl)-phen-1-yl and 4-(pyrrolidin-1-ylmethyl)-phen-1-yl, 4-(2-thiophenyl)-phen-1-yl, 4-(3-thiophenyl)-phen-1-yl, 4-(4-methylpiperazin-1-yl)-phen-1-yl, 4-(piperidinyl)phenyl or 4-(pyridinyl)-phenyl.

15. A method of selectively inhibiting cathepsin K activity in a mammal which comprises administering to a mammal in need thereof an effective amount of a compound of claim 9.

16. A method of selectively inhibiting cathepsin L and/or S activity in a mammal which comprises administering to a mammal in need thereof an effective amount of a compound of claim 3.

17. A process for the preparation of a compound of formula I as defined in claim 7, comprising (a) converting an amide of the formula VI

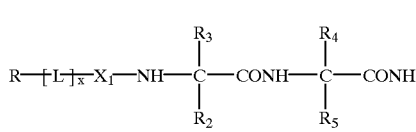

wherein R, R$_2$, R$_3$, R$_4$ and R$_5$ have meaning as previously defined in claim 7 for the compounds of formula I to a nitrile of formula I; or (b) condensing a compound of the formula VII

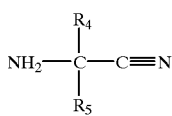

VII wherein $R_4$ and $R_5$ have meaning as defined in claim 7, with an acid of formula VIII

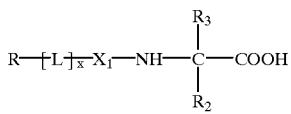

VIII wherein R, $R_2$, and $R_3$ have meaning as defined in claim 7; or with a reactive derivative thereof; or (c) condensing a compound of the formula Ia

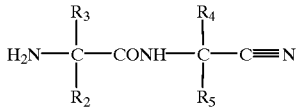

(Ia)

wherein $R_2$, $R_3$, $R_4$ and $R_5$ have meaning as defined in claim 7 with an acid corresponding to the group R—[L]$_x$—$X_1$— or with a reactive derivative thereof; and in the above processes, if required, temporarily protecting any interfering reactive groups and then isolating the resulting compound of the invention; and, if desired, converting any resulting compound into another compound of the invention; and/or if desired, converting a resulting compound into a salt or a resulting salt into the free acid or base or into another salt.

18. A method of inhibiting cathepsin activity in a mammal which comprises administering to a mammal in need thereof an effective amount of a compound of formula I as defined in claim 7.

19. A method of treating cathepsin dependent conditions in a mammal which comprises administering to a mammal in need there of effective amount of a pharmaceutical composition as defined in claim 6.

20. A method according to claim 19 of treating inflammation, osteoporosis, rheumatoid arthritis and osteoarthritis.

21. A method of treating cathepsin dependent conditions in a mammal which comprises administering to a mammal in need thereof an effective amount of a compound as defined in claim 7.

22. A cathepsin inhibiting pharmaceutical composition comprising a compound of formula I as defined in claim 7, in combination with a pharmaceutically acceptable carrier.

\* \* \* \* \*

UNITED STATES PATENT AND TRADEMARK OFFICE
CERTIFICATE OF CORRECTION

PATENT NO.    : 6,353,017 B1
DATED         : March 5, 2002
INVENTOR(S)   : Altmann et al.

It is certified that error appears in the above-identified patent and that said Letters Patent is hereby corrected as shown below:

<u>Column 154,</u>
Line 15, should read:
-- 19. A method of treating cathepsin dependent conditions in a mammal which comprises administering to a mammal in need thereof an effective amount of a pharmaceutical composition as defined in claim 6. --

Signed and Sealed this

Sixteenth Day of July, 2002

*Attest:*

*Attesting Officer*

JAMES E. ROGAN
*Director of the United States Patent and Trademark Office*